(12) United States Patent
Uhlen et al.

(10) Patent No.: US 9,416,176 B2
(45) Date of Patent: *Aug. 16, 2016

(54) RBM3 PROTEIN IN COLORECTAL CANCER PROGNOSTICS

(71) Applicant: Atlas Antibodies AB, Stockholm (SE)

(72) Inventors: Mathias Uhlen, Stocksund (SE); Fredrik Ponten, Uppsala (SE); Karin Jirstrom, Limhamn (SE)

(73) Assignee: Atlas Antibodies AB, Stockholm (SE)

( * ) Notice: Subject to any disclaimer, the term of this patent is extended or adjusted under 35 U.S.C. 154(b) by 162 days.

This patent is subject to a terminal disclaimer.

(21) Appl. No.: 14/248,398

(22) Filed: Apr. 9, 2014

(65) Prior Publication Data

US 2014/0295462 A1    Oct. 2, 2014

Related U.S. Application Data

(60) Division of application No. 13/210,816, filed on Aug. 16, 2011, now Pat. No. 8,728,739, which is a continuation-in-part of application No. PCT/EP2010/051917, filed on Feb. 16, 2010.

(60) Provisional application No. 61/169,963, filed on Apr. 16, 2009, provisional application No. 61/233,769, filed on Aug. 13, 2009, provisional application No. 61/487,341, filed on May 18, 2011.

(30) Foreign Application Priority Data

| Feb. 16, 2009 | (SE) | PCT/5E2009/000091 |
| Apr. 16, 2009 | (EP) | 09158084 |
| Aug. 13, 2009 | (EP) | 09167847 |
| Dec. 17, 2009 | (EP) | PCT/EP2009/067419 |
| May 18, 2011 | (EP) | 11166558 |

(51) Int. Cl.

| *C07K 16/00* | (2006.01) |
| *C12P 21/08* | (2006.01) |
| *C07K 16/18* | (2006.01) |
| *A61K 31/7068* | (2006.01) |
| *A61K 39/395* | (2006.01) |
| *A61K 45/06* | (2006.01) |
| *C12Q 1/68* | (2006.01) |
| *G01N 33/574* | (2006.01) |
| *C07K 14/47* | (2006.01) |
| *C07K 16/30* | (2006.01) |

(52) U.S. Cl.
CPC ............ *C07K 16/18* (2013.01); *A61K 31/7068* (2013.01); *A61K 39/39533* (2013.01); *A61K 45/06* (2013.01); *C07K 14/4748* (2013.01); *C07K 16/3038* (2013.01); *C12Q 1/6886* (2013.01); *G01N 33/57407* (2013.01); *G01N 33/57419* (2013.01); *C07K 2317/34* (2013.01); *C12Q 2600/106* (2013.01); *C12Q 2600/118* (2013.01); *C12Q 2600/158* (2013.01)

(58) Field of Classification Search
None
See application file for complete search history.

(56) References Cited

U.S. PATENT DOCUMENTS

| 8,632,984 B2 * | 1/2014 | Uhlen | C07K 14/4748 424/155.1 |
| 8,747,910 B2 * | 6/2014 | Jirstrom | C07K 14/4748 424/649 |
| 2009/0252784 A1 | 10/2009 | Houchen et al. | |

FOREIGN PATENT DOCUMENTS

| WO | WO 2007/027906 A2 | 3/2007 |
| WO | WO 2007/084485 A2 | 7/2007 |
| WO | WO 2009/102261 A1 | 8/2009 |

OTHER PUBLICATIONS

Baldi, A et al., "Identification of genes down-regulated during melanoma progression: a cDNA array study", *Exp. Dermatol.*, 2003, vol. 12, pp. 213-218.
Danno, S et al., "Decreased expression of mouse Rbm3, a cold-shock protein, in Sertoli cells of cryptorchild testis", *Am, J. Pathol.*, vol. 156, No. 5, May 2000, pp. 1685-1692.
Dresios, J et al., "Cold stress-induced protein Rbm3 binds 60S ribosomal subunits, alters microRNA levels, and enhances global protein synthesis", *Proc. Natl. Acad. Sci. USA*, vol. 102, No. 6, Feb. 8, 2005, pp. 1865-1870.
European Office Action Corresponding to European Application No. 10 704 928.0; Dated, Dec. 16, 2011; 7 pages.
European Office Action Corresponding to European Application No. 10 704 927.2; Dated, Jan. 9, 2012; 6 pages.
European Office Action Corresponding to European Application No. 09 803 750.0; Dated Feb. 13, 2012; 7 pages.
European Office Action Corresponding to European Application No. 10 705 141.9; Dated Feb. 13, 2012; 7 pages.

(Continued)

*Primary Examiner* — James Martinell
(74) *Attorney, Agent, or Firm* — Myers Bigel & Sibley, P.A.

(57) ABSTRACT

The present invention provides means, such as a method, for determining whether a mammalian subject having a colorectal cancer belongs to a first or a second group, wherein the prognosis of subjects of the first group is better than the prognosis of subjects of the second group. The method comprises the steps of: evaluating an amount of RBM3 protein or RBM3 mRNA molecule in at least part of a sample earlier obtained from the subject and determining a sample value corresponding to the evaluated amount; comparing said sample value with a predetermined reference value; and if said sample value is higher than said reference value, concluding that the subject belongs to the first group; and if said sample value is lower than or equal to said reference value, concluding that the subject belongs to the second group.

10 Claims, 23 Drawing Sheets

(56) References Cited

OTHER PUBLICATIONS

European Search Report Corresponding to European Application No. 09 158 084.5; Dated: Aug. 27, 2009; 7 pages.

International Search Report Corresponding to International Application No. PCT/EP2010/051917; Date of Mailing: Apr. 23, 2010; 17 pages.

Jogi, A et al., "Nuclear expression of the RNA-binding protein RBM3 is associated with an improved clinical outcome in breast cancer", *Modern Pathol.*, vol. 22, 2009, pp. 1564-1574.

Lleonart, ME., "A new generation of proto-oncogenes: Cold-inducible RNA binding proteins", *Biochim. Blophys. Acta*, vol. 1805, No. 1, Jan. 1, 2010, pp. 43-52.

Martinez-Arrlbas, F et al., "Positive correlation between the expression of X-chromosome RBM genes (RBMX, RBM3, rBM10) and the proapoptotic Bax gene in human breast cancer", *J. Cell. Biochem.*, vol. 97, No. 6, 2006, pp. 1275-1282.

Mourtada-Maarabouni, M et al., "The antiapoptotic RBM5/LUCA-15/H37 gene and its role in apoptosis and human cancer: Research update", *Scientific World J.*, vol. 6, pp. 1705-1712, Mar. 15, 2007.

Nilsson, P et al., "Towards a human proteome atlas: High-throughput generation of monospecific antibodies for tissue profiling", *Proteomics*, vol. 5, 2005, pp. 4327-4337.

Price, P et al., "The growth rate of metastatic non-seminomatous germ cell testicular tumours measured by marker production doubling time-II. Prognostic significance in patients treated by chemotherapy", *Eur. J. Cancer*, vol. 26, No. 4, pp. 453-457, 1990.

Richie, JP, "OCT4 staining in testicular tumors. A sensitive and specific marker for seminoma and embryonal carcinoma", *J. Urol.*, 174 (2), 2005, pp. 569-570.

Slootstra, JW et al., "Structural aspects of antibody-antigen interaction revealed through small random peptide libraries", *Mol. Diversity*, vol. 1, 1995, pp. 87-96.

Sureban, SM et al., "Translation regulatory factor RBM3 Is a proto-oncogene that prevents mitotic catastrophe", *Oncogene*, vol. 27, No. 33, Jul. 1, 2008, pp. 4544-4556.

Sutherland, LC et al., "RNA binding motif (RBM) proteins: A novel family of apoptosis modulators?" *J. Cell. Biochem.*, vol. 94, 2005, pp. 5-24.

Wellmann, S et al,, "The RNA-binding protein RBM3 Is required for cell proliferation and protects against serum deprivation-induced cell death", *Pediatric Res.*, vol. 67, No. 1, 2010, pp. 35-41.

Zeng, Y et al., "Down-regulating cold shock protein genes impairs cancer cell survival and enhances chemosensitivity", *J. Cell. Biochem.*, vol. 107, No. 1, Mar. 10, 2009, pp. 179-188.

\* cited by examiner

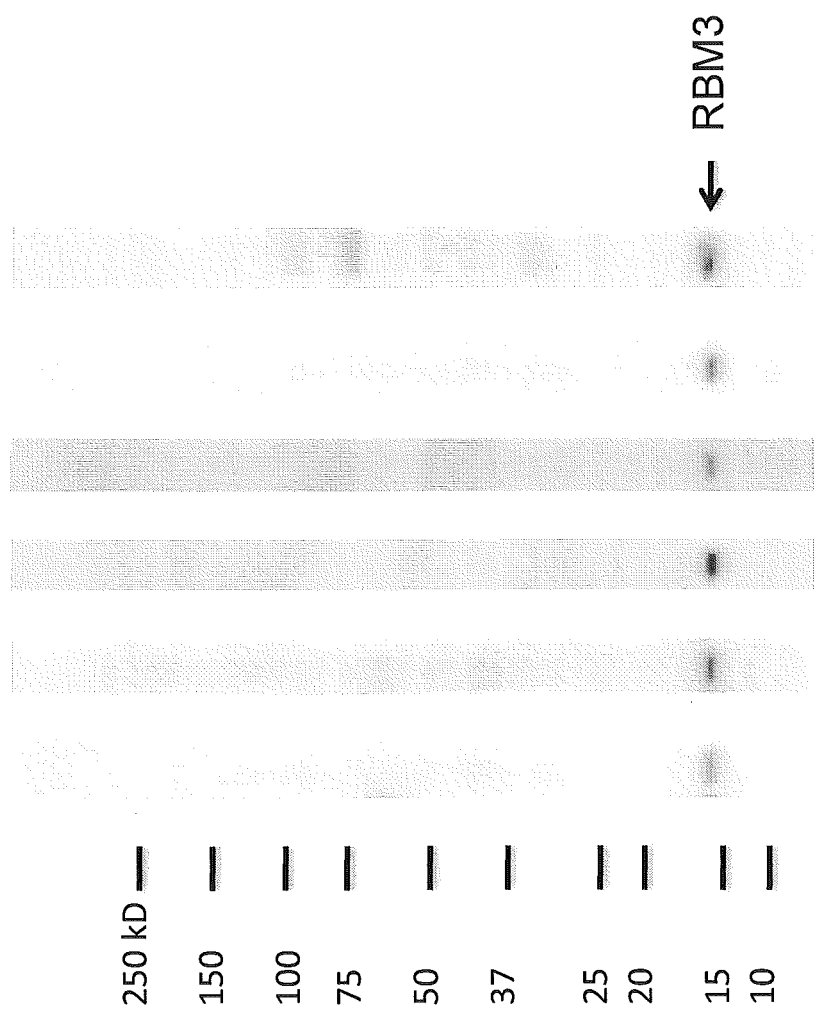

```
            RGFGFITFTNPEHASVAMRAMNGESLDGR (SEQ ID NO: 4)
          CTQRSRGFGFITFTNPEHASV            (SEQ ID NO: 23)
Peptide 6.  TQRSRGFGFITFTNP                (SEQ ID NO: 20)
Peptide 7.    GFGFITFTNPEHASV              (SEQ ID NO: 24)
Peptide 8.       TFTNPEHASVAMRAM           (SEQ ID NO: 25)
                 TFTNPEHASV                (SEQ ID NO: 26)
                 FTN                       (SEQ ID NO: 22)
```

FIGURE 23

RBM3 PROTEIN IN COLORECTAL CANCER PROGNOSTICS

This application is a Continuation-In-Part of PCT/EP2010/051917, filed Feb. 16, 2010, which claims priority to PCT/SE2009/000091, filed Feb. 16, 2009, U.S. Provisional Application No. 61/169,963, filed Apr. 16, 2009, EP09158084.5, filed Apr. 16, 2009, U.S. Provisional Application No. 61/233,769, filed Aug. 13, 2009, EP09167847.4, filed Aug. 13, 2009, and PCT/EP2009/067419, filed Dec. 17, 2009. The present application also claims priority to U.S. Provisional Application No. 61/487,341, filed May 18, 2011 and EP11166558.4, filed May 18, 2011.

FIELD OF THE INVENTION

The present invention relates to the field of colorectal cancer prognostics and colorectal cancer treatment.

BACKGROUND OF THE INVENTION

Cancer

Cancer is one of the most common causes of disease and death in the western world. In general, incidence rates increase with age for most forms of cancer. As human populations continue to live longer, due to an increase of the general health status, cancer may affect an increasing number of individuals. The cause of most common cancer types is still largely unknown, although there is an increasing body of knowledge providing a link between environmental factors (dietary, tobacco smoke, UV radiation etc) as well as genetic factors (germ line mutations in "cancer genes" such as p53, APC, BRCA1, XP etc) and the risk for development of cancer.

No definition of cancer is entirely satisfactory from a cell biological point of view, despite the fact that cancer is essentially a cellular disease and defined as a transformed cell population with net cell growth and anti-social behavior. Malignant transformation represents the transition to a malignant phenotype based on irreversible genetic alterations. Although this has not been formally proven, malignant transformation is believed to take place in one cell, from which a subsequently developed tumor originates (the "clonality of cancer" dogma). Carcinogenesis is the process by which cancer is generated and is generally accepted to include multiple events that ultimately lead to growth of a malignant tumor. This multi-step process includes several rate-limiting steps, such as addition of mutations and possibly also epigenetic events, leading to formation of cancer following stages of precancerous proliferation. The stepwise changes involve accumulation of errors (mutations) in vital regulatory pathways that determine cell division, asocial behavior and cell death. Each of these changes may provide a selective Darwinian growth advantage compared to surrounding cells, resulting in a net growth of the tumor cell population. A malignant tumor does not only necessarily consist of the transformed tumor cells themselves but also surrounding normal cells which act as a supportive stroma. This recruited cancer stroma consists of connective tissue, blood vessels and various other normal cells, e.g., inflammatory cells, which act in concert to supply the transformed tumor cells with signals necessary for continued tumor growth.

The most common forms of cancer arise in somatic cells and are predominantly of epithelial origin, e.g., prostate, breast, colon, urothelium and skin, followed by cancers originating from the hematopoietic lineage, e.g., leukemia and lymphoma, neuroectoderm, e.g., malignant gliomas, and soft tissue tumors, e.g., sarcomas.

Cancer Diagnostics and Prognostics

Microscopic evaluation of a tissue section taken from a tumor remains the golden standard for determining a diagnosis of cancer. For example, for microscopic diagnosis, biopsy material from suspected tumors is collected and examined under the microscope. To obtain a firm diagnosis, the tumor tissue is fixated in formalin, histo-processed and paraffin embedded. From the resulting paraffin block, tissue sections can be produced and stained using both histochemical, i.e., hematoxylin-eosin staining, and immunohistochemical (IHC) methods. The surgical specimen is then evaluated with pathology techniques, including gross and microscopic analysis. This analysis often forms the basis for assigning a specific diagnosis, i.e., classifying the tumor type and grading the degree of malignancy, of a tumor.

Malignant tumors can be categorized into several stages according to classification schemes specific for each cancer type. The most common classification system for solid tumors is the tumor-node-metastasis (TNM) staging system. The T stage describes the local extent of the primary tumor, i.e., how far the tumor has invaded and imposed growth into surrounding tissues, whereas the N stage and M stage describe how the tumor has developed metastases, with the N stage describing spread of tumor to lymph nodes and the M stage describing growth of tumor in other distant organs. Early stages include: T0-1, N0, M0, representing localized tumors with negative lymph nodes. More advanced stages include: T2-4, N0, M0, localized tumors with more widespread growth and 11-4, N1-3, M0, tumors that have metastasized to lymph nodes and T1-4, N1-3, M1, tumors with a metastasis detected in a distant organ. Staging of tumors is often based on several forms of examination, including surgical, radiological and histopathological analyses. In addition to staging, for most tumor types there is also a classification system to grade the level of malignancy. The grading systems rely on morphological assessment of a tumor tissue sample and are based on the microscopic features found in a given tumor. These grading systems may be based on the degree of differentiation, proliferation and atypical appearance of the tumor cells. Examples of generally employed grading systems include Gleason grading for prostatic carcinomas and the Nottingham Histological Grade (NHG) grading for breast carcinomas.

Accurate staging and grading is crucial for a correct diagnosis and may provide an instrument to predict a prognosis. The diagnostic and prognostic information for a specific tumor subsequently determines an adequate therapeutic strategy for a given cancer patient. A commonly used method, in addition to histochemical staining of tissue sections, to obtain more information regarding a tumor is immunohistochemical staining. IHC allows for the detection of protein expression patterns in tissues and cells using specific antibodies. The use of IHC in clinical diagnostics allows for the detection of immunoreactivity in different cell populations, in addition to the information regarding tissue architecture and cellular morphology that is assessed from the histochemically stained tumor tissue section. IHC can be involved in supporting the accurate diagnosis, including staging and grading, of a primary tumor as well as in the diagnostics of metastases of unknown origin. The most commonly used antibodies in clinical practice today include antibodies against cell type "specific" proteins, e.g., PSA (prostate), MelanA (melanocytes) and Thyroglobulin (thyroid gland), and antibodies recognizing intermediate filaments (epithelial, mesenchymal, glial), cluster of differentiation (CD) antigens (hematopoietic, sub-classification of lymphoid cells) and markers of malignant potential, e.g., Ki67 (proliferation), p53 (commonly mutated tumor suppressor gene) and HER-2 (growth factor receptor).

Aside from IHC, the use of in situ hybridization for detecting gene amplification and gene sequencing for mutation analysis are evolving technologies within cancer diagnostics. In addition, global analysis of transcripts, proteins or metabolites all add relevant information. However, most of these analyses still represent basic research and have yet to be evaluated and standardized for the use in clinical medicine.

Adenocarcinomas from Colon and Rectum (Colorectal Cancer)

Colorectal cancer, a malignant epithelial tumor that presents as an adenocarcinoma, is one of the most common forms of human cancer worldwide. Data from the GLOBOCAN 2002 database presented by Parkin et al show that around 1 million new cases of colorectal cancer are identified yearly (Parkin D M et al (2005) CA Cancer J Clin 55, 74-108). Further, the incidence of colorectal cancer in the world is approximately 9.4% of all cancers, and colorectal cancer constitutes the second most common cause of death in the western world. The five-year survival rate of colorectal cancer is approximately 60% in the western world but as low as 30% in Eastern Europe and India.

Early detection and surgery with excision of the tumor is currently of critical importance for a successful treatment. For localized tumors, i.e. tumors that have not evolved into a metastasizing disease, surgical intervention with radical resection of the tumor and surrounding bowel and tissues is performed. Colorectal tumors are categorized into several stages according to Dukes' stages A-D or more recently according to the TNM classification. Early stage tumors (Dukes' stages A and B) are generally associated with a relatively favorable outcome, while later stage tumors, presenting with metastasis (Dukes' stage C and D) have poor survival rates. Unfortunately, colorectal cancer has often grown to a considerable size before detection and thus metastases are not uncommon. The tumor typically metastasizes to regional lymph nodes, but distant metastasis to the liver and lung are also common.

Symptoms depend on where in the distal gastrointestinal tract the tumor is located, and include bowel distress, diarrhea, constipation, pain and anemia (secondary to bleeding from the tumor into the bowel). Current diagnostics are based on patient history, clinical and endoscopic examination (rectoscopy and colonoscopy), optionally followed by radiological mapping to determine extensiveness of tumor growth. In conjunction with endoscopic examination, tissue biopsies are performed from dubious lesions.

In differential diagnostics, cytokeratin 20 (CK20), an intermediate filament marker abundant in the glandular cells of the GI-tract, is commonly used to diagnose primary tumors in the GI-tract including colorectal cancer. The CK20 marker is not ideal as several other adenocarcinomas also can be positive for CK20 antibodies, whereas not all colorectal cancers are positive. Prognostic information is mainly obtained from tumor staging classification as there are no accepted grading systems or protein markers that provide additional prognostic data. Today there are no available markers that can distinguish tumors of low malignancy grade and low risk for developing into a metastasizing disease from highly malignant tumors with a reduced chance of survival. Thus, there is a great need for molecular markers that can be used to predict patient outcome and to guide patient management including therapeutic intervention.

Endpoint Analysis

Endpoint analysis for trials with adjuvant treatments for cancer gives important information on how the patients respond to a certain therapy. Overall survival (OS) has long been considered the standard primary endpoint. OS takes into account time to death, irrespective of cause, e.g. if the death is due to cancer or not. Loss to follow-up is censored and regional recurrence, distant metastases, second primary colorectal cancers, and second other primary cancers are ignored.

Today, an increasing number of effective treatments available in many types of cancer have resulted in the need for surrogate endpoints to allow for a better evaluation of the effect of adjuvant treatments. Thus, the much longer follow-up required to demonstrate that adjuvant treatments improve OS is often complemented with other clinical endpoints that gives an earlier indication on how successful the treatment is.

In the present disclosure, patient cohorts are evaluated by OS analysis, however a surrogate endpoint is also considered, namely disease-free survival (DFS). Analysis of DFS includes time to any event related to the same cancer, i.e. all cancer recurrences and deaths from the same cancer are events.

SUMMARY

The present disclosure can be summarized in the following itemized embodiments:

1. Method for determining whether a mammalian subject having a colorectal cancer belongs to a first or a second group, wherein the prognosis of subjects of the first group is better than the prognosis of subjects of the second group, comprising the steps of:
   a) evaluating an amount of RBM3 protein or RBM3 mRNA in at least part of a sample earlier obtained from the subject and determining a sample value corresponding to the evaluated amount;
   b) comparing said sample value with a predetermined reference value; and
   if said sample value is higher than said reference value,
   c1) concluding that the subject belongs to the first group; and if said sample value is lower than or equal to said reference value,
   c2) concluding that the subject belongs to the second group.

2. Method for determining whether a prognosis for a mammalian subject having a colorectal cancer is better than a reference prognosis, comprising the steps of:
   a) evaluating the amount of RBM3 protein or RBM3 mRNA present in at least part of a sample earlier obtained from the subject, and determining a sample value corresponding to said evaluated amount;
   b) comparing the sample value obtained in step b) with a reference value associated with said reference prognosis; and, if said sample value is higher than said reference value,
   c) concluding that the prognosis for said subject is better than said reference prognosis.

3. Method for determining whether a prognosis for a mammalian subject having a colorectal cancer is worse than or equal to a reference prognosis, comprising the steps of:
   a) evaluating the amount of RBM3 protein or RBM3 mRNA present in at least part of a sample earlier obtained from the subject, and determining a sample value corresponding to said evaluated amount;

b) comparing the sample value obtained in step b) with a reference value associated with said reference prognosis; and, if said sample value is lower than or equal to said reference value, c) concluding that the prognosis for said subject is worse than or equal to said reference prognosis.

4. Method for determining whether a subject having a colorectal cancer is not in need of treatment with a colorectal treatment regimen, comprising the steps of:

a) evaluating the amount of RBM3 protein or RBM3 mRNA present in at least part of a sample earlier obtained from the subject, and determining a sample value corresponding to said evaluated amount;

b) comparing the sample value obtained in step b) with a reference value; and, if said sample value is higher than said reference value, c) concluding that said subject is not in need of the treatment with the colorectal cancer treatment regimen.

5. Non-treatment strategy method for a subject having a colorectal cancer, comprising:

a) evaluating the amount of RBM3 protein or RBM3 mRNA present in at least part of a sample earlier obtained from the subject, and determining a sample value corresponding to said evaluated amount;

b) comparing the sample value obtained in step b) with a reference value; and,
if said sample value is higher than said reference value, c) refraining from treating said subject with a colorectal cancer treatment regimen.

6. Method of treatment of a subject having a colorectal cancer, comprising:

a) evaluating the amount of RBM3 protein or RBM3 mRNA present in at least part of a sample from the subject, and determining a sample value corresponding to said evaluated amount;

b) comparing the sample value obtained in step b) with a reference value; and, if said sample value is equal to or lower than said reference value, c) treating said subject with a colorectal cancer treatment regimen.

7. Method according to any one of items 4-6, wherein said colorectal cancer treatment regimen is neo-adjuvant therapy and/or adjuvant therapy.

8. Method according to item 7, in which said neo-adjuvant therapy is radiation therapy and said adjuvant therapy is selected from colorectal cancer chemotherapies, colorectal cancer immunotherapies, radiation therapy and combinations thereof.

9. Method according to item 7 or 8, wherein said colorectal cancer is in Dukes' stage B and said colorectal cancer treatment regimen is an adjuvant systemic treatment with a chemotherapeutic agent.

10. Method according to item 7 or 8, wherein said colorectal cancer is in Dukes' stage C and said colorectal cancer treatment is an adjuvant combination therapy comprising:
a first chemotherapeutic agent and
a second chemotherapeutic agent or an immunotherapeutic agent.

11. Method according to any one of the preceding items, wherein said colorectal cancer is located in the sigmoideum.

12. Method according to any one of items 1-3, wherein said prognosis is a probability of survival, such as overall survival or disease free survival, and said reference prognosis is a reference probability of survival, such as overall survival or disease free survival, wherein both survivals are the same type of survival.

13. Method according to item 12, wherein the probability of survival is a probability of five-year, ten-year or 15-year survival.

14. Method according to any one of items 1-9 and 11-13, wherein said colorectal cancer is in Dukes' stage A or B.

15. Method according to any one of items 1-8 and 10-13, wherein said colorectal cancer is in Dukes' stage C or D.

16. Method according to any one of the preceding items, wherein said colorectal cancer is colorectal carcinoma.

17. Method according to any one of the preceding items, wherein said sample is a body fluid sample, stool sample or cytology sample.

18. Method according to item 17, wherein said body fluid sample is selected from the group consisting of blood, plasma, serum, cerebral fluid, urine, semen and exudate.

19. Method according to any one of the preceding items, wherein said sample comprises cells, such as tumor cells or stromal cells, from said subject.

20. Method according to any one of items 1-16, wherein said sample is a tissue sample.

21. Method according to item 20, wherein said tissue sample comprises tumor cells or stromal cells.

22. Method according to item 21, wherein said tissue sample is derived from colon or rectum.

23. Method according to item 22, wherein said tissue sample is derived from sigmoid colon.

24. Method according to any one of items 19-23, wherein the evaluation of step a) is limited to the nuclei and/or cytoplasms of cells of said sample.

25. Method according to item 24, wherein the evaluation of step a) is limited to the nuclei and/or cytoplasms of tumor cells of said sample.

26. Method according to any one of the preceding items, wherein said subject is a human.

27. Method according to any one of the preceding items, wherein said subject is male or female.

28. Method according to any one of the preceding items, wherein said reference value is a value corresponding to a predetermined amount of RBM3 protein or RBM3 mRNA in a reference sample.

29. Method according to any preceding item, wherein the sample value of step a) is determined as being either 1, corresponding to detectable RBM3 protein or RBM3 mRNA in the sample, or 0, corresponding to no detectable RBM3 protein or RBM3 mRNA in the sample.

30. Method according to any preceding item, wherein the reference value of step b) corresponds to a reference sample having no detectable RBM3 protein.

31. Method according to any preceding item, wherein the reference value of step b) is 0.

32. Method according to any one of the preceding items, wherein said reference value is a nuclear fraction, a nuclear intensity, or a function of a nuclear fraction and a nuclear intensity.

33. Method according to item 32, wherein said reference value is a nuclear fraction of 50-90% RBM3 protein positive cells.

34. Method according to item 32, wherein said reference value is a nuclear fraction of 0-10% RBM3 protein positive cells.

35. Method according to item 32, wherein said reference value is a moderate nuclear intensity.

36. Method according to item 32, wherein said reference value is an absent nuclear intensity.

37. Method according to any one of items 1-31, wherein said reference value is a cytoplasmic fraction, a cytoplasmic intensity, or a function of a cytoplasmic fraction and a cytoplasmic intensity.

38. Method according to item 37, wherein said reference value is a cytoplasmic fraction of 50-90% RBM3 protein positive cells.

39. Method according to item 37, wherein said reference value is a cytoplasmic fraction of 0-10% RBM3 protein positive cells.

40. Method according to item 37, wherein said reference value is a moderate cytoplasmic intensity.

41. Method according to item 37, wherein said reference value is an absent cytoplasmic intensity.

42. Method according to any one of the preceding items, wherein the amino acid sequence of the RBM3 protein comprises or consists of a sequence selected from:
   i) SEQ ID NO:1; and
   ii) a sequence which is at least 85% identical to SEQ ID NO:1.

43. Method according to any one of the preceding items, wherein the amino acid sequence of the RBM3 protein comprises or consists of a sequence selected from:
   i) SEQ ID NO:2; and
   ii) a sequence which is at least 85% identical to SEQ ID NO:2.

44. Method according to any one of the preceding items, wherein step a) comprises:
   aI) applying to said sample a quantifiable affinity ligand capable of selective interaction with the RBM3 protein to be evaluated, said application being performed under conditions that enable binding of the affinity ligand to RBM3 protein present in the sample; and
   aII) quantifying the affinity ligand bound to said sample to evaluate said amount.

45. Method according to any one of items 1-43, wherein step a) comprises:
   a1) applying to said sample a quantifiable affinity ligand capable of selective interaction with the RBM3 protein to be quantified, said application being performed under conditions that enable binding of the affinity ligand to RBM3 protein present in the sample;
   a2) removing non-bound affinity ligand; and
   a3) quantifying affinity ligand remaining in association with the sample to evaluate said amount.

46. Method according to item 44 or 45, wherein the quantifiable affinity ligand is selected from the group consisting of antibodies, fragments thereof and derivatives thereof.

47. Method according to item 46, wherein said quantifiable affinity ligand is obtainable by a process comprising a step of immunizing an animal with a peptide whose amino acid sequence consists of a sequence SEQ ID NO:1.

48. Method according to item 46, wherein said quantifiable affinity ligand is obtainable by a process comprising a step of immunizing an animal with a peptide whose amino acid sequence consists of a sequence selected from SEQ ID NO:4 and SEQ ID NO:5.

49. Method according to item 46, wherein said quantifiable affinity ligand is obtainable by a process comprising a step of immunizing an animal with an RBM3 fragment which consists of 20 amino acids or less, such as 15 amino acids or less, and comprises a sequence selected from SEQ ID NO:6-19.

50. Method according to item 46, wherein said quantifiable affinity ligand is obtainable by a process comprising a step of immunizing an animal with an RBM3 fragment which consists of 20 amino acids or less, such as 15 amino acids or less, and comprises a sequence selected from SEQ ID NO:8, 16 and 17.

51. Method according to item 44 or 45, wherein said quantifiable affinity ligand is an oligonucleotide molecule.

52. Method according to item 44 or 45, wherein the quantifiable affinity ligand is a protein ligand derived from a scaffold selected from the group consisting of staphylococcal protein A and domains thereof, lipocalins, ankyrin repeat domains, cellulose binding domains, γ crystallines, green fluorescent protein, human cytotoxic T lymphocyte-associated antigen 4, protease inhibitors, PDZ domains, peptide aptamers, staphylococcal nuclease, tendamistats, fibronectin type III domain and zinc fingers.

53. Method according to any one of items 44-52, wherein said quantifiable affinity ligand is capable of selective interaction with a peptide whose amino acid sequence consists of a sequence SEQ ID NO:1.

54. Method according to any one of items 44-53, wherein said quantifiable affinity ligand is capable of selective interaction with a peptide whose amino acid sequence consists of a sequence selected from SEQ ID NO:4 and SEQ ID NO:5.

55. Method according to any one of items 44-53, wherein said quantifiable affinity ligand is capable of selective interaction with an RBM3 fragment which consists of 20 amino acids or less, such as 15 amino acids or less, and comprises an amino acid sequence selected from SEQ ID NO:6-19.

56. Method according to any one of items 44-53, wherein said quantifiable affinity ligand is capable of selective interaction with an RBM3 fragment which consists of 20 amino acids or less, such as 15 amino acids or less, and comprises a sequence selected from SEQ ID NO:8, 16 and 17.

57. Method according to any one of items 44-56, wherein the quantifiable affinity ligand comprises a label selected from the group consisting of fluorescent dyes and metals, chromophoric dyes, chemiluminescent compounds and bioluminescent proteins, enzymes, radioisotopes, particles and quantum dots.

58. Method according to any one of items 44-57, in which said quantifiable affinity ligand is detected using a secondary affinity ligand capable of recognizing the quantifiable affinity ligand.

59. Method according to item 58, in which said secondary affinity ligand capable of recognizing the quantifiable affinity ligand comprises a label selected from the group consisting of fluorescent dyes and metals, chromophoric dyes, chemiluminescent compounds and bioluminescent proteins, enzymes, radioisotopes, particles and quantum dots.

60. Kit for carrying out the method according to any one of the preceding items, which comprises
   a) a quantifiable affinity ligand capable of selective interaction with an RBM3 protein; and
   b) reagents necessary for quantifying the amount of said quantifiable affinity ligand.

61. Kit according to item 60, in which said quantifiable affinity ligand is selected from the group consisting of antibodies, fragments thereof and derivatives thereof.

62. Kit according to item 61, in which said quantifiable affinity ligand is obtainable by a process comprising a step of immunizing an animal with a protein whose amino acid sequence consists of the sequence SEQ ID NO:1.

63. Kit according to item 61, in which said quantifiable affinity ligand is obtainable by a process comprising a step of immunizing an animal with a protein whose amino acid sequence consists of a sequence selected from SEQ ID NO:4 and SEQ ID NO:5.

64. Kit according to item 61, in which said quantifiable affinity ligand is obtainable by a process comprising a step of immunizing an animal with an RBM3 fragment which consists of 20 amino acids or less, such as 15 amino acids or less, and comprises an amino acid sequence selected from SEQ ID NO:6-19.

65. Kit according to item 61, in which said quantifiable affinity ligand is obtainable by a process comprising a step of immunizing an animal with an RBM3 fragment which consists of 20 amino acids or less, such as 15 amino acids or less, and comprises an amino acid sequence selected from SEQ ID NO:8, 16 and 17.

66. Kit according to item 60, in which said quantifiable affinity ligand is a protein ligand derived from a scaffold selected from the group consisting of staphylococcal protein A and domains thereof, lipocalins, ankyrin repeat domains, cellulose binding domains, γ crystallines, green fluorescent protein, human cytotoxic T lymphocyte-associated antigen 4, protease inhibitors, PDZ domains, peptide aptamers, staphylococcal nuclease, tendamistats, fibronectin type III domain and zinc fingers.

67. Kit according to any of one of items 60, in which said quantifiable affinity ligand is an oligonucleotide molecule.

68. Kit according to any one of items 60-67, in which said quantifiable affinity ligand is capable of selective interaction with an RBM3 protein comprising, or consisting of, a sequence selected from:
i) SEQ ID NO:1; and
ii) a sequence which is at least 85% identical to SEQ ID NO:1.

69. Kit according to any one of items 60-67, in which said quantifiable affinity ligand is capable of selective interaction with an RBM3 protein comprising, or consisting of, a sequence selected from:
i) SEQ ID NO:2; and
ii) a sequence which is at least 85% identical to SEQ ID NO:2.

70. Kit according to any one of items 60-69, in which said quantifiable affinity ligand is capable of selective interaction with an RBM3 protein comprising a sequence selected from SEQ ID NO:4 and SEQ ID NO:5.

71. Kit according to any one of items 60-69, in which said quantifiable affinity ligand is capable of selective interaction with an RBM3 protein consisting of a sequence selected from SEQ ID NO:4 and SEQ ID NO:5.

72. Kit according to any one of items 60-69, in which said quantifiable affinity ligand is capable of selective interaction with an RBM3 fragment which consists of 20 amino acids or less, such as 15 amino acids or less, and comprises an amino acid sequence selected from SEQ ID NO:6-19.

73. Kit according to any one of items 60-69, in which said quantifiable affinity ligand is capable of selective interaction with an RBM3 fragment which consists of 20 amino acids or less, such as 15 amino acids or less, and comprises an amino acid sequence selected from SEQ ID NO:8, 16 and 17.

74. Kit according to any one of items 60-73, in which said quantifiable affinity ligand comprises a label selected from the group consisting of fluorescent dyes and metals, chromophoric dyes, chemiluminescent compounds and bioluminescent proteins, enzymes, radioisotopes, particles and quantum dots.

75. Kit according to any one of items 60-74, in which said reagents necessary for quantifying said amount of said quantifiable affinity ligand comprise a secondary affinity ligand capable of recognizing said quantifiable affinity ligand.

76. Kit according to item 75, in which said secondary affinity ligand comprises a label selected from the group consisting of fluorescent dyes or metals, chromophoric dyes, chemiluminescent compounds and bioluminescent proteins, enzymes, radioisotopes, particles and quantum dots.

77. Kit according to any one of items 60-76, further comprising at least one reference sample for provision of a reference value.

78. Kit according to item 77, in which at least one reference sample is a tissue sample comprising no detectable RBM3 protein.

79. Kit according to item 77 or 78, in which at least one reference sample comprises RBM3 protein.

80. Kit according to any one of items 77-79, in which at least one reference sample comprises an amount of RBM3 protein corresponding to a cytoplasmic fraction of 50-90%.

81. Kit according to any one of items 77-79, in which at least one reference sample comprises an amount of RBM3 protein corresponding to a cytoplasmic fraction of 0-10%.

82. Kit according to any one of items 77-79, in which at least one reference sample comprises an amount of RBM3 protein corresponding to a moderate cytoplasmic intensity.

83. Kit according to any one of items 77-79, in which at least one reference sample comprises an amount of RBM3 protein corresponding to an absent cytoplasmic intensity.

84. Kit according to any one of items 77-83, in which at least one reference sample comprises an amount of RBM3 protein or RBM3 mRNA corresponding to a value being higher than said reference value.

85. Kit according to item 84, in which at least one reference sample comprises an amount of RBM3 protein corresponding to a strong cytoplasmic intensity.

86. Kit according to item 84 or 85, in which at least one reference sample comprises an amount of RBM3 protein corresponding to a cytoplasmic fraction of 75% or higher.

87. Kit according to any one of items 77-86 comprising:
a first reference sample comprising an amount of RBM3 protein or RBM3 mRNA corresponding to a value (positive reference value) being higher than a reference value; and a second reference sample comprising an amount of RBM3 protein or RBM3 mRNA corresponding to a value (negative reference value) being lower than or equal to said reference value.

88. Kit according to any one of items 77-87, in which said reference sample(s) comprise(s) cell lines.

89. RBM3 protein fragment which consists of 50 amino acids or less and comprises an amino acid sequence selected from SEQ ID NO:4-19.

90. RBM3 protein fragment according to item 89, which consists of 29 amino acids or less.

91. RBM3 protein fragment according to item 89 or 90, which consists of 20 amino acids or less and comprises an amino acid sequence selected from SEQ ID NO:6-19.

92. RBM3 protein fragment according to item 91, which consists of 20 amino acids or less and comprises an amino acid sequence selected from SEQ ID NO:8, 16 and 17.

93. RBM3 protein fragment according to item 91 or 92, which consists of 15 amino acids or less.

94. Use in vitro of an RBM3 protein or RBM3 mRNA molecule as a prognostic marker.

95. Use according to item 94, wherein said prognostic marker is a prognostic marker for a cancer.

96. Use according to item 95, wherein said cancer is a colorectal cancer.

97. Use according to item 96, wherein said protein is provided in a sample from a subject having a colorectal cancer.

98. Use according to item 97, wherein said sample is a colorectal tumor tissue sample.

99. Use according to any one of items 96-98, wherein said prognostic marker is a marker for a relatively good prognosis for colorectal cancer.

100. Use in vitro of an RBM3 protein, or an antigenically active fragment thereof, for the selection or purification of a prognostic agent for establishing a prognosis for a mammalian subject having a colorectal cancer.

101. Use of an RBM3 protein, or an antigenically active fragment thereof, for the production of a prognostic agent for establishing a prognosis for a mammalian subject having a colorectal cancer.

102. Use according to item 100 or 101, wherein said prognostic agent is an affinity ligand capable of selective interaction with the RBM3 protein or the antigenically active fragment thereof.

103. Use according any one of items 94-102, wherein the amino acid sequence of the RBM3 protein comprises or consists of a sequence selected from:
 i) SEQ ID NO:1; and
 ii) a sequence which is at least 85% identical to SEQ ID NO:1.

104. Use according any one of items 94-102, wherein the amino acid sequence of the RBM3 protein comprises or consists of a sequence selected from:
 i) SEQ ID NO:2; and
 ii) a sequence which is at least 85% identical to SEQ ID NO:2.

105. Use of an antigenically active fragment according to any one of items 100-102, wherein the fragment is a fragment according to anyone of items 89-93.

106. Affinity ligand capable of selective interaction with an RBM3 protein.

107. Affinity ligand according to item 106, which is an antibody or a fragment or a derivative thereof.

108. Affinity ligand, which is obtainable by a process comprising a step of immunizing an animal with a peptide whose amino acid sequence consists of a sequence SEQ ID NO:1.

109. Affinity ligand, which is obtainable by a process comprising a step of immunizing an animal with a peptide whose amino acid sequence consists of sequence SEQ ID NO:4 or 5 or a RBM3 protein fragment which consists of 20 amino acids or less, such as 15 amino acids or less, and comprises an amino acid sequence selected from SEQ ID NO:6-19.

110. Affinity ligand according to item 109, which is obtainable by a process comprising a step of immunizing an animal with a peptide whose amino acid sequence consists of SEQ ID NO:5 or a RBM3 protein fragment which consists of 20 amino acids or less, such as 15 amino acids or less, and comprises a sequence selected from SEQ ID NO:8, 16 and 17.

111. Affinity ligand, which is capable of selective interaction with a peptide whose amino acid sequence consists of a sequence SEQ ID NO:1.

112. Affinity ligand capable of selective interaction with a peptide whose amino acid sequence consists of SEQ ID NO:4 or 5 oran RBM3 fragment which consists of 20 amino acids or less, such as 15 amino acids or less, and comprises an amino acid sequence selected from SEQ ID NO:6-19.

113. Affinity ligand capable of selective interaction with a peptide whose amino acid sequence consists of SEQ ID NO:5 oran RBM3 fragment which consists of 20 amino acids or less, such as 15 amino acids or less, and comprises an amino acid sequence selected from SEQ ID NO:8, 16 and 17.

114. Affinity ligand according to any one of items 106-113 for use in vivo for establishing a prognosis for a mammalian subject having a colorectal cancer.

115. Use invitro of an affinity ligand according to any one of items 106-113 as a prognostic agent.

116. Use according to item 115 as a prognostic agent for colorectal cancer.

117. Use according to item 115 or 116, wherein said prognostic agent is an affinity ligand capable of selective interaction with the RBM3 protein, or an antigenically active fragment thereof.

118. Use of an affinity ligand according to any one of items 106-113 in the manufacture of a prognostic agent for in vivo establishment of a prognosis for a mammalian subject having a colorectal cancer.

119. Use of an affinity ligand according to any one of items 106-113 for establishing a prognosis for a mammalian subject having a colorectal cancer.

BRIEF DESCRIPTION OF THE FIGURES

FIG. 1A shows overall survival (OS) in all patients, estimated five-year survival is 55% for all patients in this cohort. FIG. 1B shows disease free survival (DFS) in all patients, estimated five-year survival is 64% for all patients in this cohort.

In FIG. 3A a low RBM3 level equals NF<2%, represented by a solid line and a high RBM3 level equals NF≥2%, represented by a dotted line. In FIG. 3B a low RBM3 level equals NF≤75%, represented by a solid line and a high RBM3 level equals NF>75%, represented by a dotted line.

In FIG. 5A a solid line represents a low RBM3 level (NF<2%), and a dotted line represents a high RBM3 level (NF≥2%). In FIG. 5B a solid line represents a low RBM3 level (NF≤75%), and a dotted line represents a high RBM3 level (NF>75%).

FIG. 6A shows OS. FIG. 6B shows DFS.

In FIG. 7A a low RBM3 level equals CI=0, represented by a solid line and a high RBM3 level equals CI>0, represented by a dotted line. In FIG. 7B a low RBM3 level equals CI<2, represented by a solid line and a high RBM3 level equals CI=2, represented by a dotted line.

In FIG. 8A a low RBM3 level equals CI=0, represented by a solid line and a high RBM3 level equals CI>0, represented by a dotted line. In FIG. 8B a low RBM3 level equals CI<2, represented by a solid line and a high RBM3 level equals CI=2, represented by a dotted line.

In FIG. 9A a low RBM3 level equals NF<2%, represented by a solid line and a high RBM3 level equals NF≥2%, represented by a dotted line. In FIG. 9B a low RBM3 level equals NF≤75%, represented by a solid line and a high RBM3 level equals NF>75%, represented by a dotted line.

FIG. 10A shows OS. FIG. 10B shows DFS.

In FIG. 12A a low RBM3 level equals NF<2%, represented by a solid line and a high RBM3 level equals NF≥2%, represented by a dotted line. In FIG. 12B a low RBM3 level equals NF≤75%, represented by a solid line and a high RBM3 level equals NF>75%, represented by a dotted line.

FIG. 13A shows OS. FIG. 13B shows DFS.

In FIG. 15A all subjects were split into four groups based on NF status, i.e. <2%, 2-25%, >25-75% or >75%. In FIG. 15B RBM3 expression was dichotomized into a high and a low category, where a solid line represents a low RBM3 level (NF<75%), and a dotted line represents a high RBM3 level (NF≥75%).

In FIG. 16A all subjects were split into four groups based on NF status, i.e. <2%, 2-25%, >25-75% or >75%. In FIG. 16B RBM3 expression was dichotomized into a high and a low category, where a solid line represents a low RBM3 level (NF<75%), and a dotted line represents a high RBM3 level (NF≥75%).

FIG. 17A shows OS. FIG. 17B shows DFS.

FIG. 18A shows OS. FIG. 18B shows DFS.

In FIG. 19A, a solid line represents a low RBM3 level (CI<2), and a dotted line represents a high RBM3 level (CI=2). In FIG. 19B, a solid line represents a low RBM3 level (CI=0 2), and a dotted line represents a high RBM3 level (CI>0).

In FIG. 20A subjects were split into four groups based on NF status, i.e. <2%, 2-25%, >25-75% or >75%. In FIG. 20B tissue cores were dichotomized by high and low RBM3 expression. A solid line represents a low RBM3 level (NF<3), and a dotted line represents a high RBM3 level (NF=3). In FIG. 20C tissue cores were dichotomized by high and low RBM3 expression. A solid line represents a low RBM3 level (NF=0), and a dotted line represents a high RBM3 level (NF>0).

In FIG. 21A a solid line represents a low cytoplasmic RBM3 level (CI=0), and a dotted line represents a high cytoplasmic RBM3 level (CI>0). In FIG. 21B a solid line represents a low nucleic RBM3 level (NI=0), and a dotted line represents a high nucleic RBM3 level (NI>0).

FIG. 22 shows Western blot results for, from left to right, 7F5, 10F1, 12A10, 12C9, 14D9 and anti-RBM3. Thus, lanes 1 through 5 show the monoclonal antibodies while lane 6 shows the polyclonal anti-RBM3 antibody.

FIG. 23 shows alignment of SEQ ID NO:4 as well as the peptides used for epitope mapping of the monoclonal antibodies.

DETAILED DESCRIPTION

Figure 1A:
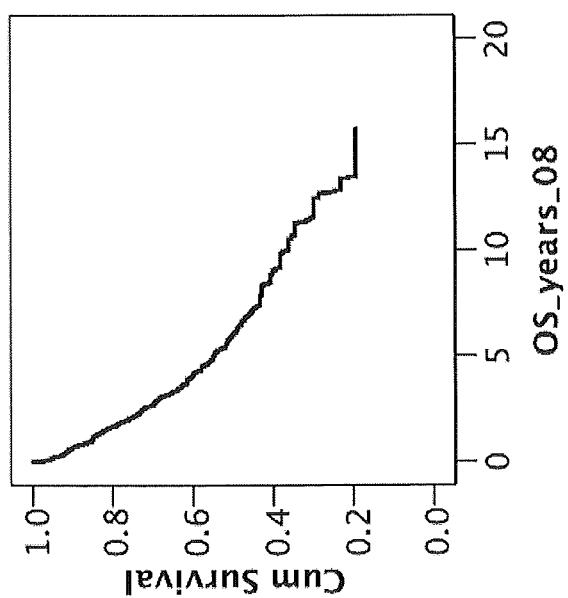
FIGS. 1A-1B show the results of a survival analysis of 274 subjects diagnosed with cancer of the sigmoid colon.

Thus, as a first configuration of the first aspect of the present disclosure, there is provided a method for determining whether a prognosis for a mammalian subject having a colorectal cancer is better than a reference prognosis, comprising the steps of:
   a) evaluating the amount of RBM3 protein or RBM3 mRNA present in at least part of a sample earlier obtained from the subject, and determining a sample value corresponding to said evaluated amount;
   b) comparing the sample value obtained in step b) with a reference value associated with said reference prognosis;
   and, if said sample value is higher than said reference value,
   c) concluding that the prognosis for said subject is better than said reference prognosis.

Further, as a second configuration of the first aspect, there is provided a method for determining whether a prognosis for a mammalian subject having a colorectal cancer is worse than or equal to a reference prognosis, comprising the steps of:
   a) evaluating the amount of RBM3 protein or RBM3 mRNA present in at least part of a sample earlier obtained from the subject, and determining a sample value corresponding to said evaluated amount;

b) comparing the sample value obtained in step a) with a reference value associated with said reference prognosis; and, if said sample value is lower than or equal to said reference value, c) concluding that the prognosis for said subject is worse than or equal to said reference prognosis.

The first and second embodiment may also be combined. Thus, according to the first aspect there is also provided a method for determining a prognosis for a mammalian subject having a colorectal cancer, comprising the steps of:

a) evaluating the amount of RBM3 protein or RBM3 mRNA present in at least part of a sample earlier obtained from the subject, and determining a sample value corresponding to said evaluated amount;

d) comparing the sample value obtained in step a) with a reference value associated with a reference prognosis; and, if said sample value is higher than said reference value, c1) concluding that the prognosis for said subject is better than said reference prognosis; and/or
if said sample value is lower than or equal to said reference value, c2) concluding that the prognosis for said subject is worse than or equal to said reference prognosis.

However closely related and covered by the same concept, c1) and c2) provide two alternative conclusions.

The inventive concept of the present disclosure may also form the basis for a decision to refrain from a certain treatment regimen.

For example, as shown in the attached FIGS. 2-13B and 15A-21B, the prognoses for subjects showing high RBM3 protein levels are generally better than those for subjects showing low RBM3 protein levels. Provided with the teachings of the present disclosure, a physician may consider the prognosis of an RBM3 high subject as being so favorable that one adjuvant treatment regimen is avoided and another less aggressive adjuvant treatment regimen is selected instead. For example, a monotherapy may be selected instead of a combination therapy. Further, the decision may be to refrain from any adjuvant therapy. The present disclosure may thus relieve subjects from over-treatment.

Thus, as a third configuration of the first aspect, there is provided a method for determining whether a subject having a colorectal cancer is not in need of a treatment with a colorectal cancer treatment regimen, comprising the steps of:

a) evaluating the amount of RBM3 protein or RBM3 mRNA present in at least part of a sample earlier obtained from the subject, and determining a sample value corresponding to said evaluated amount;

b) comparing the sample value obtained in step b) with a reference value; and, if said sample value is higher than said reference value, c) concluding that said subject is not in need of the treatment with the colorectal cancer treatment regimen.

Also, as a fourth configuration of the first aspect, there is provided a non-treatment strategy method for a subject having a colorectal cancer, comprising:

a) evaluating the amount of RBM3 protein or RBM3 mRNA present in at least part of a sample earlier obtained from the subject, and determining a sample value corresponding to said evaluated amount;

b) comparing the sample value obtained in step b) with a reference value; and, if said sample value is higher than said reference value, c) refraining from treating said subject with a colorectal cancer treatment regimen.

The colorectal treatment regimen of the third or fourth treatment configuration of the first aspect may for example be an adjuvant systemic treatment with a specific therapeutic agent or combination of therapeutic agents, which agent or agents may be selected from chemotherapeutic agents and immunotherapeutic agents.

For example, the refraining of step c) of the fourth configuration may be a refraining from treatment during at least one week from the completion of steps a)-b), such as at least one month from the completion of steps a)-b), such as at least three months from the completion of steps a)-b), such as at least six months from the completion of steps a)-b), such as at least one year from the completion of steps a)-b), such as at least two years from the completion of steps a)-b).

Alternatively, the refraining of step c) may be a refraining from treatment until the next time the method is performed or until recurrence of a colorectal cancer tumor.

As a fifth configuration of the first aspect, there is provided a method for determining whether a mammalian subject having a colorectal cancer belongs to a first or a second group, wherein the prognosis of subjects of the first group is better than the prognosis of subjects of the second group, comprising the steps of:

a) evaluating an amount of RBM3 protein or RBM3 mRNA in at least part of a sample earlier obtained from the subject and determining a sample value corresponding to the evaluated amount;

b) comparing said sample value with a predetermined reference value; and
if said sample value is higher than said reference value, c1) concluding that the subject belongs to the first group; and if said sample value is lower than or equal to said reference value, c2) concluding that the subject belongs to the second group.

In the method of the fifth configuration of the first aspect, it is determined whether a colorectal cancer subject belongs to a first or a second group, wherein subjects of the first group generally have a better prognosis than subjects of the second group. The division of colorectal cancer subjects into the two groups is determined by comparing samples values from the subjects with a reference value. In the present disclosure it is shown that various reference values may be employed to discriminate between subjects that generally survived for a comparatively long period (represented by the upper curve) and subjects that generally survived for a comparatively short period (represented by the lower curve) (see the figures). The reference value is thus the determinant for the size of the respective groups; the higher the reference value, the fewer the subjects in the first group and the lower the likelihood that a tested subject belongs to the first group. As the prognosis generally increases as the sample value increases, a relatively high reference value may in some instances be selected to identify subjects with a particularly good prognosis. Guided by the present disclosure, the person skilled in the art may select relevant reference values without undue burden. This is further discussed below.

The first and the second group may consist exclusively of subjects having colorectal cancers of the same or similar stage as the tested subject. Further, the groups may consist only of subjects having the same or similar age, race, sex, genetic characteristics and/or medical status or history, such as colorectal cancer history.

According to an alternative configuration of the first aspect, there is provided a method for establishing a prognosis for a mammalian subject having a colorectal cancer:

a) evaluating the amount of RBM3 protein or RBM3 mRNA present in at least part of a sample from the subject, and determining a sample value corresponding to the evaluated amount; and b) correlating the sample value of step b) to the prognosis for the subject.

In the context of the present disclosure, "establishing a prognosis" refers to establishing a specific prognosis or a prognosis interval.

In an embodiment of the alternative configuration, the sample may be an earlier obtained sample.

The correlating of step b) refers to any way of associating survival data to the obtained sample value so as to establish a prognosis for the subject.

The present invention based on RBM3 levels as a colorectal cancer status indicator has a number of benefits. In general, identification of the aggressiveness of a colorectal cancer is of vital importance as it helps a physician selecting an appropriate treatment strategy. For example, if a particularly aggressive form of a cancer is identified, a painful or in any other sense unpleasant treatment which normally is avoided may anyway be considered. Further, if less aggressive forms can be identified, over-treatment may be avoided. As a further example, the RBM3, as a marker for which a certain level of expression is correlated with a certain pattern of disease progression, has a great potential for example in a panel for making predictions or prognoses or for the selection of a treatment regimen.

Sureban S M et al discusses the role of RBM3 protein in human cancer and concludes that the protein is significantly upregulated in tumors and exhibits a stage-dependent increase in colorectal cancer (Sureban S M et al (2008) Oncogene 27, 4544-4566). Consequently, RBM3 expression is associated with unfavorable colorectal cancer characteristics in the article, which is mainly based on in vitro data, and such findings are in contrast with the teachings of the present disclosure.

In the present disclosure, different RBM3 protein values (sample values) corresponding to various prognoses are presented. Typically, a low sample value is associated with a poorer prognosis than a high sample value. In the method of the first configuration of the first aspect, the sample value is compared to a reference value, and if the sample value is equal to or lower than the reference value, it is concluded that the prognosis for the subject is equal to, or worse than, a reference prognosis associated with the reference value.

Consequently, the above method may be adapted to a reference value. In such case, starting from a sample value which under the circumstances is considered to be relevant, a reference value which is equal to the sample value may be selected. Subsequently, a reference prognosis associated with that reference value may be established. Guided by the present disclosure, the person skilled in the art understands how to establish a reference prognosis which corresponds to a given reference value. For example, the relation between sample values and survival data in a relevant group of cancer patients may be examined in line with what is described in Examples, Section 4, below. The procedure described therein may be adapted to a given reference value. Then, a prognosis corresponding to the given reference value may be selected as the reference prognosis.

Also, the above method may be adapted to a given reference prognosis. In such case, starting from a reference prognosis which under the circumstances is considered to be relevant, for example for selecting an appropriate therapy, a corresponding reference value may be established. Guided by the present disclosure, the person skilled in the art understands how to establish a reference value which corresponds to a given reference prognosis. For example, the relation between sample values and survival data in a group of cancer patients may be examined as in Examples, Section 4, below, but the procedure described therein may be adapted to establish reference values corresponding to a given reference prognosis. For example, different reference values may be tested until one which correlates with the given reference prognosis is found.

Accordingly, in embodiments of the methods of the above aspect, the reference prognosis may be based on a previously established prognosis, e.g., obtained by an examination of a relevant population of subjects. Such reference population may be selected to match the tested subject's age, sex, race, colorectal cancer stage and/or medical status and history. Further, a prognosis may be adapted to a background risk in the general population, a statistical prognosis/risk or an assumption based on an examination of the subject. Such examination may also comprise the subject's age, sex, race, colorectal cancer stage and/or medical status and history. Thus, a physician may for example adapt the reference prognosis to the subject's colorectal cancer history, the stage of the tumor, the morphology of the tumor, the location of the tumor, the presence and spread of metastases and/or further cancer characteristics.

In general, when deciding on a suitable treatment strategy for a patient having colorectal cancer, the physician responsible for the treatment may take several parameters into account, such as the result of an immunohistochemical evaluation, patient age, hormone receptor status, general condition and medical history, such as colorectal cancer history. To be guided in such decision, the physician may perform an RBM3 test, or order an RBM3 test performed, according to the first aspect. Further, the physician may assign to someone else, such as a lab worker, to perform step a), and optionally step b), while performing step c), and optionally b), himself.

The inventive concept of the present disclosure may also form the basis for applying various treatment regimes.

For example, as shown in the attached FIGS. 2-13B and 15A-21B, the prognoses for subjects showing low RBM3 protein levels are generally worse than those for subjects showing high RBM3 protein levels. Provided the teachings of the present disclosure, a physician may thus consider the prognosis of an RBM3 low subject as being so poor that a certain adjuvant treatment regimen is appropriate. The present disclosure may thus provide for accurate treatment of a previously undertreated group.

As a first configuration of a second aspect of the present disclosure, there is thus provided a method of treatment of a subject having a colorectal cancer, comprising:

a) evaluating the amount of RBM3 protein or RBM3 mRNA present in at least part of a sample from the subject, and determining a sample value corresponding to said evaluated amount;

b) comparing the sample value obtained in step b) with a reference value; and, if said sample value is equal to or lower than said reference value, c) treating said subject with a colorectal cancer treatment regimen.

According to one embodiment, the method may comprise the additional step:

d) and if said sample value is higher than said reference value, refraining from treating said subject with the colorectal cancer treatment regimen.

A subject may have a colorectal cancer in such an advanced stage that an adjuvant therapy would normally be considered superfluous and unnecessary painful. However, in such case, a physician may anyway decide to apply the adjuvant therapy if the subject in question has an increased probability of prolonged survival due to a high RBM3 protein or RBM3 mRNA value.

Thus, as a second configuration of the second aspect, there is provided a method of treatment of a subject having a colorectal cancer of an advanced stage, such as Dukes' stage D, comprising:
- a) evaluating the amount of RBM3 protein or RBM3 mRNA present in at least part of a sample from the subject, and determining a sample value corresponding to said evaluated amount;
- b) comparing the sample value obtained in step b) with a reference value; and, if said sample value is higher than said reference value,
- c) treating said subject with a colorectal cancer treatment regimen for prolonged survival.

Further, if said sample value is lower than or equal to said reference value, the subject may be treated with palliative treatment only.

In one embodiment of the methods of the second aspect, the reference value of step b) may be associated with a reference prognosis and said treatment regimen of step c) may be adapted to a prognosis which is worse than or equal to the reference prognosis. In such an embodiment of the first configuration of the second aspect, the method may comprise the additional step: d) and if said sample value is higher than said reference value, treating said subject with a treatment regimen adapted to a prognosis which is better than the reference prognosis, for which the appropriate treatment regimen may be no treatment.

The method of treatment may be limited to the decision-making and treatment. Thus, as an alternative configuration of the second aspect, there is provided a method of treatment of a subject having a colorectal cancer, comprising:
- α) comparing a sample value corresponding to a level of RBM3 protein or RBM3 mRNA in a sample from the subject with a reference value; and, if said sample value is equal to or lower than said reference value,
- β) treating said subject with an adjuvant colorectal cancer treatment regimen.

Numerous ways of obtaining a sample value corresponding to a level of RBM3 protein or RBM3 mRNA in a sample from a subject are described in the present disclosure.

The physician responsible for the treatment according to the second aspect may assign to someone else, such as a lab worker, to perform step a), and optionally step b), while performing step C), and optionally b), himself.

Regarding step a) of the methods of the present disclosure, an increase in the amount of RBM3 protein or RBM3 mRNA typically results in an increase in the sample value, and not the other way around. However, in some embodiments, the evaluated amount may correspond to any of a predetermined number of discrete sample values. In such embodiments, a first amount and a second, increased, amount may correspond to the same sample value. In any case, an increase in the amount of RBM3 protein or RBM3 mRNA will not result in a decrease in the sample value in the context of the present disclosure.

However inconvenient, but in an equivalent fashion, the evaluated amounts may be inversely related to sample values if the qualification between step b) and c) is inverted. For example, the qualification between step b) and c) is inverted if the phrase "if the sample value is lower than or equal to the reference value" is replaced with "if the sample value is higher than or equal to the reference value".

In the context of the present disclosure, "prognosis" refers to the prediction of the course or outcome of a disease and its treatment. For example, prognosis may also refer to a determination of chance of survival or recovery from a disease, as well as to a prediction of the expected survival time of a subject. A prognosis may specifically involve establishing the likelihood for survival of a subject during a period of time into the future, such as three years, five years, ten years or any other period of time. A prognosis may further be represented by a single value or a range of values.

Further, in the context of the methods of the present disclosure, "earlier obtained" refers to obtained before the method is performed. Consequently, if a sample earlier obtained from a subject used in a method, the method does not involve obtaining the sample from the subject, i.e., the sample was previously obtained from the subject in a step separate from the method.

Further, in the context of the present disclosure, "a mammalian subject having a colorectal cancer" refers to a mammalian subject having a primary or secondary colorectal tumor or a mammalian subject which has had a tumor removed from the colon and/or rectum, wherein the removal of the tumor refers to killing or removing the tumor by any appropriate type of surgery or therapy. In the method and use aspects of the present disclosure, "a mammalian subject having a colorectal cancer" also includes the cases wherein the mammalian subject is suspected of having a colorectal at the time of the performance of the use or method and the colorectal cancer diagnosis is established later.

Further, in the context of the present disclosure, the "reference value" refers to a predetermined value found to be relevant for making decisions or drawing conclusions regarding the prognosis or a suitable treatment strategy for the subject.

Also, in the context of the present disclosure, a reference value being "associated" with a reference prognosis refers to the reference value being assigned a corresponding reference prognosis, based on empirical data and/or clinically relevant assumptions. For example, the reference value may be the average RBM3 protein or RBM3 mRNA value in a relevant group of subjects and the reference prognosis may be an average survival in the same group. Further, the reference value does not have to be assigned to a reference prognosis directly derived from prognosis data of a group of subjects exhibiting the reference value. The reference prognosis may for example correspond to the prognosis for subjects exhibiting the reference value or lower. That is, if the reference value is 1 on a scale from 0 to 2, the reference prognosis may be the prognosis of the subjects exhibiting the values 0 or 1. Consequently, the reference prognosis may also be adapted to the nature of the available data. As further discussed above, the reference prognosis may be further adapted to other parameters as well.

Step a) of the methods of the above aspects involve evaluating the amount of RBM3 protein or RBM3 mRNA present in at least part of the sample, and determining a sample value corresponding to the amount. The "at least part of the sample" refers to a relevant part or relevant parts of the sample for establishing the prognosis or drawing conclusions regarding suitable treatments. The person skilled in the art understands which part or parts that are relevant under the circumstances present when performing the method. For example, if evaluating a sample comprising cells, the skilled person may only consider the tumor cells, or only the cytoplasms or nuclei of tumor cells, of the sample.

Further, in step a) an amount is evaluated and a sample value corresponding to the amount is determined. Consequently, an exact measurement of the amount of RBM3 protein or RBM3 mRNA is not required for obtaining the sample value. For example, the amount of RBM3 protein or RBM3 mRNA may be evaluated by visual inspection of a stained tissue sample and the sample value may then be categorized as a e.g. high or low based on the evaluated amount.

The person skilled in the art understands how to perform such evaluation and determination. Further, the present disclosure provides guidance for such evaluation and determination.

The treatment regimen of the first and second aspect may for example be an adjuvant and/or a neo-adjuvant therapy. The neo-adjuvant therapy may for example be radiation therapy, especially in cases of rectal cancer. Appropriate adjuvant therapies are primarily chemotherapies and immunotherapies. Further, the adjuvant treatment may be chemotherapy and/or immunotherapy in combination with radiation therapy.

The general strategy is that a more comprehensive treatment is applied if a subject is found to be RBM3 low than if the subject is found to be RBM3 high.

For example, if the subject has a Dukes' stage B colorectal cancer, the adjuvant treatment regimen may be chemotherapy. That means that according to some of the above methods, a chemotherapeutic agent is administered to the subject if the subject is RBM3 low. However, if the subject is RBM3 high, the treatment with the chemotherapeutic agent may be considered unnecessary, and therefore, is not administered to the subject.

As another example, if the subject has a Dukes' stage C colorectal cancer, the treatment regimen may be a combination of two or more chemotherapeutic agents. That means that according to some of the above methods, the combination is administered to the subject if the subject is RBM3 low. However, if the subject is RBM3 high, the combination may be considered unnecessary, and therefore, not applied to the subject. In the latter case, treatment with one therapeutic agent may be considered necessary.

Non-limiting examples of chemotherapeutic agents are 5-fluorouracil, capecitabine, Xeloda®, irinotecan and oxaliplatin. 5-fluorouracil, Capecitabine and Xeloda® are typically given alone as monotherapy or in combination with other agents, while irinotecan and oxaliplatin are usually given in combination with other agents. Non-limiting examples of immunotherapeutic agents are bevacizumab and cetuximab.

In embodiments of the first and second aspect, the prognosis may be a probability of survival and said reference prognosis may be a reference probability of survival provided that both survivals are the same type of survival. As explained in the background section, there are several ways to measure "survival". The survivals of the first and second aspects may for example be overall survivals or disease free survivals. Further, the "survival" may be measured over different periods, such as five, ten or 15 years. Accordingly, the survivals may be five-year, ten-year or 15-year survivals.

In embodiments of the methods of the above aspects, the subject may have colorectal cancer in different forms and/or stages.

Figure 9B:
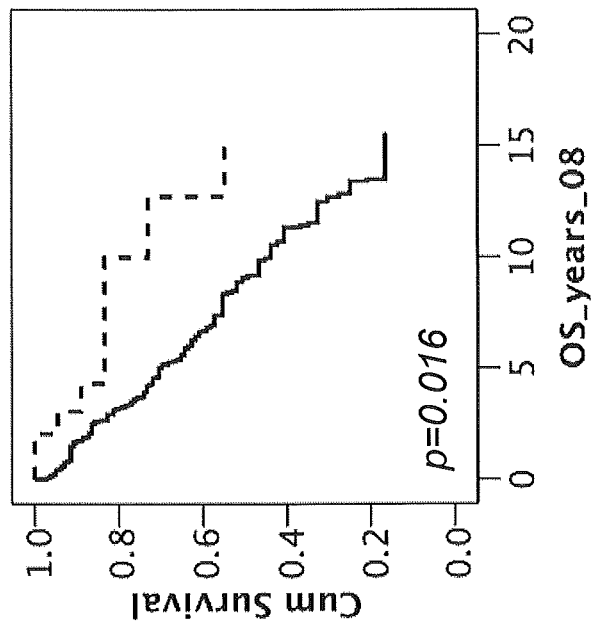
FIGS. 9A-9B show the results of OS analysis for the 158 subjects diagnosed with Dukes stage A or B based on nuclear fraction (NF) levels of RBM3. RBM3 expression was dichotomized into high and low categories in two ways.
Figure 9A:
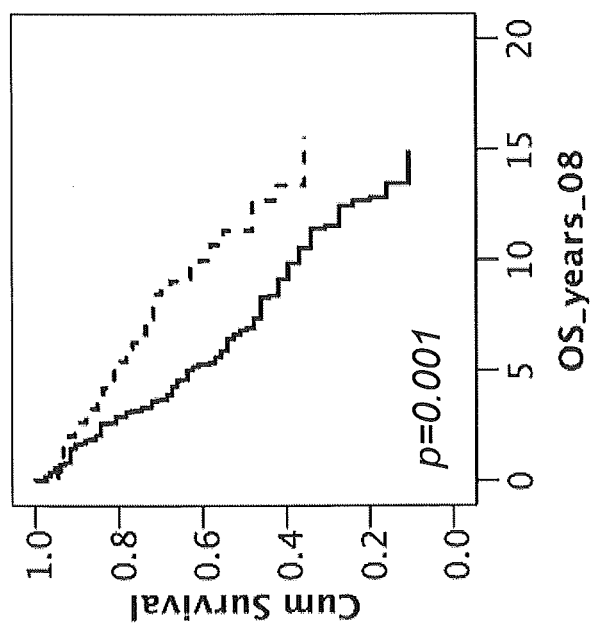
Figure 10B:
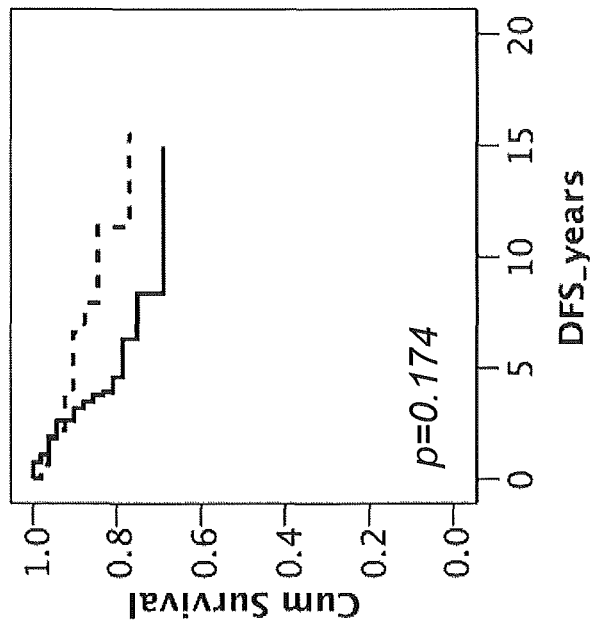
FIGS. 10A-10B show the results of survival analysis for the 124 subjects diagnosed with Dukes stage B based on nuclear fraction (NF) levels of RBM3. Tissue cores were dichotomized by high and low RBM3 expression. A solid line represents a low RBM3 level (NF<2%), and a dotted line represents a high RBM3 level (NF≥2%).
Figure 10A:
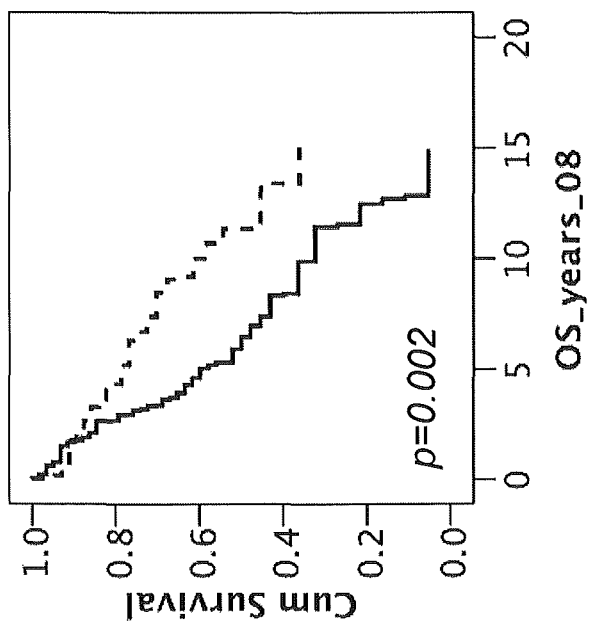
Figure 11:
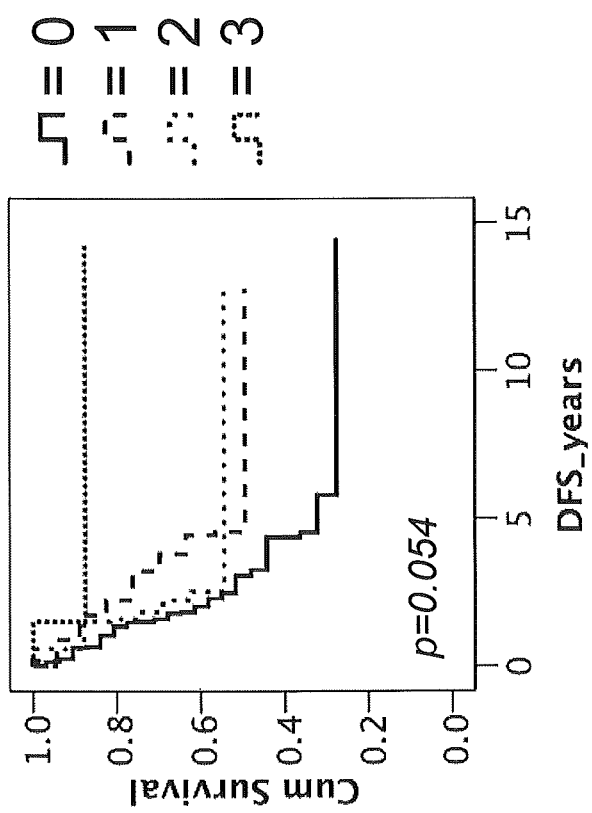
FIG. 11 shows the impact on DFS if splitting the 75 subjects diagnosed with Dukes stage C into groups based on nuclear fraction (NF) staining. The subjects were split into four groups based on NF status, i.e. <2%, 2-25%, >25-75% or >75%.

In some embodiments of these aspects, the colorectal cancer in question is a node-negative colorectal cancer, i.e. colorectal cancer that has not progressed to the lymph node metastasizing stage. In other similar embodiments, the colorectal cancer in question is in either Dukes' stage A or B. In yet other embodiments, the colorectal cancer in question is colorectal adenoma or colorectal carcinoma. In these embodiments, determining that the subject exhibits low RBM3 expression may be of great value for the prognosis of future progression of the disease and thus form the basis for an informed decision with regard to future disease management. Within a group of subjects afflicted with such a comparatively early stage of disease, subjects with low RBM3 expression probably are at a comparatively high risk of developing a more aggressive disease. Low RBM3 expression among subjects having node-negative colorectal cancer or Dukes' stage A or B colorectal cancer may therefore indicate that these subjects should be monitored more closely and/or treated differently than subjects that do not exhibit low RBM3 expression. The methods according to the invention therefore offers the possibility of a greater chance for survival over a certain period of time and/or longer survival time for such subjects, owing to the additional prognostic information given by the RBM3 protein or RBM3 mRNA marker. Further, as shown in FIGS. 9A-9B, high RBM3 protein levels are associated with a particularly good prognosis among subjects having Dukes' stage A or B colorectal cancers. The methods of the first aspect may therefore be used for identifying the subjects having Dukes' stage A or B colorectal cancers that are not in need of any adjuvant treatment.

Subjects having a Dukes' stage A colorectal cancer are traditionally not treated with adjuvant chemotherapy. However, guided by the teachings of the present disclosure, a physician may decide to give such a subject exhibiting low, or absent, RBM3 expression an adjuvant treatment anyway.

Consequently, in embodiments of the methods of the above aspects, the colorectal cancer is in Dukes' stage A. In an alternative or complementary embodiment, said colorectal cancer is in T1-2, N0 and M0 according to the TNM staging system described above.

Regarding subjects having a Dukes' stage B cancers, it may be particularly difficult to determine whether to apply an adjuvant therapy or not. Consequently, a Dukes' stage B subject in particular may be revealed from treatment after a favorable prognosis has been determined by means of a RBM3 measurement. Accordingly, in some embodiments, the colorectal cancer of the methods of the above aspects may be in Dukes' stage B.

Subjects having Dukes' stage C colorectal cancers are normally treated with adjuvant treatment. If such a subject is found to have a relatively poor prognosis, a combined adjuvant treatment may be considered more appropriate than a single treatment, even though the combined treatment causes more side-effects and is costlier.

Accordingly, in some embodiments, the colorectal cancer of the methods of the above aspects may be a metastasizing colorectal cancer.

In similar embodiments, the colorectal cancer in question may be in Dukes' stage C or D, preferably C.

In embodiments of the methods of the above aspects, the sample may be a body fluid sample. For example, the body fluid sample may be selected from the group consisting of blood, plasma, serum, cerebral fluid, urine, semen, lymph and exudate. Alternatively, the sample may be a cytology sample or a stool sample.

The level of RBM3 expression may preferably be measured intracellularly. Thus, the body fluid, cytology or stool sample may for example comprise cells, such as tumor cells.

In further embodiments of the methods of the above aspects, the sample may be a tissue sample, such as a colorectal tissue sample, e.g. a sample derived from the colon or rectum. Tissue samples facilitate RBM3 protein expression analysis by means of immunohistochemistry.

The results of Examples, Section 4, are based on examination on tissue samples from the sigmoid colon. Accordingly, in embodiments of the methods of the above aspects the sample may be a tissue sample derived from the sigmoid colon.

However, the inventors have also observed a correlation between RBM3 expression and prognosis in a cohort based primarily on samples from cancer of the left colon and rectal cancer.

The inventors have found that RBM3 is expressed both in tumor tissue and stroma. Accordingly, the tissue may comprise tumor cells or stromal cells, from said subject.

Further, the inventors have noted that both nuclear and cytoplasmic expression of RBM3 protein is relevant for determining prognoses or selecting treatments (see for example FIGS. 2-6B, 9A-12B, 15A-18B and 21B regarding nuclear expression and FIGS. 7A-8B, 13A-13B, 19A-19B and 21A regarding cytoplasmic expression). Thus, the evaluation of step a) may be limited to the nuclei and/or cytoplasms of cells, such as tumor cells or stromal cells, of said sample. Consequently, when a tissue sample is examined, only the nuclei or cytoplasms of tumor cells may be taken into consideration. Such examination may for example be aided by immunohistochemical staining.

The tissue samples in Examples, Section 4, are from male and female humans. Accordingly, the subject of the methods of the above aspects may be a human, and further, the subject of the methods of the above aspects may be male or female.

The inventors have found that subjects who suffer from colorectal cancer and show essentially no RBM3 protein expression generally have a particularly poor prognosis (see FIGS. 2, 3A, 4, 5A, 6A-6B, 7A, 8A, 9A, 10A-10B, 11, 12A, 13A-13B, 19B, 20C and 21). Consequently, the "cut-off value" determining whether the subject is RBM3 high or RBM3 low may be zero.

Thus, in embodiments of the methods of the above aspects, the sample value of step b) may be either 1, corresponding to detectable RBM3 protein in the sample, or 0, corresponding to no detectable RBM3 protein in the sample. Consequently, in such embodiments, the evaluation of the sample is digital: RBM3 protein is considered to be either present or not. In the context of the present disclosure, "no detectable RBM3 protein" refers to an amount of RBM3 protein that is so small that it is not, during normal operational circumstances, detectable by a person or an apparatus performing the relevant step of the method according to any one of the above aspects. The "normal operational circumstances" refer to the laboratory methods and techniques a person skilled in the art would find appropriate for performing the methods of the present disclosure.

Accordingly, in embodiments of the methods of the present disclosure, the reference value of step b) may be 0. And it follows that, in further embodiments of the methods of the present disclosure, the reference value of step b) may correspond to a reference sample having no detectable RBM3 protein (see below).

A sample value of RBM3 protein or RBM3 mRNA being higher than the reference value, or a subject from which such sample value is obtained, is sometimes referred to herein as being "RBM3 high". Further, a sample value of RBM3 protein or RBM3 mRNA being lower than, or equal to, the reference value, or a subject from which such sample value is obtained, is sometimes referred to herein as being "RBM3 low".

In the context of the present disclosure, the terms "sample value" and "reference value" are to be interpreted broadly. The quantification of RBM3 protein or RBM3 mRNA to obtain these values may be done via automatic means, via a scoring system based on visual or microscopic inspection of samples, or via combinations thereof. However, it is also possible for a skilled person, such as a person skilled in the art of histopathology, to determine the sample and reference values merely by inspection, e.g., of tissue slides that have been stained for RBM3 protein expression. The determination of the sample value being higher than the reference value may thus correspond to the determination, upon visual or microscopic inspection, that a sample tissue slide is more densely stained and/or exhibit a larger fraction of stained cells than is the case for a reference tissue slide. The sample value may also be compared to a reference value given by a literal reference, such as a reference value described in wording or by a reference picture. Consequently, the sample and/or reference values may in some cases be mental values that the skilled person determines upon inspection and comparison.

For example, the skilled person may categorize a sample as being RBM3 protein high or low, wherein the sample is categorized as high if it contains more RBM3 protein than a previously inspected reference sample and low if it contains less or equally much. Such evaluation may be assisted by staining the sample, and, if necessary, a reference sample, with a staining solution comprising e.g., antibodies selective for RBM3 protein.

A reference value, found to be relevant for establishing prognosis or making treatment decisions regarding colorectal cancer subjects, for use as comparison with the sample value from the subject, may be provided in various ways. With the knowledge of the teachings of the present disclosure, the skilled artisan can, without undue burden, provide relevant reference values for performing the methods of the present disclosure.

The person performing the methods of the above aspects may, for example, adapt the reference value to desired information. For example, the reference value may be adapted to yield the most significant prognostic information, e.g., the largest separation between the RBM3 high survival curve and the RBM3 low survival curve. Alternatively, the reference value may be selected such that a group having particularly good prognoses or a particularly poor prognosis is singled out. An absent cytoplasmic intensity (FIGS. 8A, 13A-13B, 19B, 21A), an absent nuclear intensity (FIGS. 6A-6B, 21B) and a nuclear fraction of <2% (FIGS. 2, 3A, 4, 5A, 9A, 10A-10B, 11, 12A, 20C) are examples of reference values that may be used for singling out groups having particularly poor prognoses, while a weak/moderate cytoplasmic intensity (FIGS. 7B, 19A), a weak/moderate nuclear intensity (FIGS. 18A-18B) and a nuclear fraction of 75% (FIGS. 2, 3B, 4, 5B, 9B, 11, 12B, 15B, 16B, 20B) are examples of reference values that may be used for singling out groups having a particularly good prognosis.

In embodiments of the methods of the above aspects, the reference value may correspond to the amount of RBM3 protein or RBM3 mRNA expression in a healthy tissue, such as healthy colorectal tissue, or stroma tissue of the subject of the method. As another example, the reference value may be provided by the amount of RBM3 protein or RBM3 mRNA expression measured in a standard sample of normal tissue from another, comparable subject. As another example, the reference value may be provided by the amount of RBM3 protein or RBM3 mRNA expression measured in a reference sample comprising or being derived from tumor cells, such as a reference sample of tumor tissue, e.g., colorectal cancer tissue. The amount of protein expression of the reference sample may preferably be previously established. Consequently, the reference value may be provided by the amount of RBM3 measured in a reference sample comprising (or being derived from) cells expressing a predetermined amount of RBM3.

Further, the reference value may for example be provided by the amount of RBM3 expression measured in a reference sample comprising cell lines, such as cancer cell lines, expressing a predetermined, or controlled, amount of RBM3. The person skilled in the art understands how to provide such cell lines, for example guided by the disclosure of Rhodes et al. (2006) *The biomedical scientist*, p 515-520.

Consequently, in embodiments of the methods of the present disclosure, the reference value may be a predetermined value corresponding to the amount of RBM3 protein or RBM3 mRNA expression in a reference sample.

However, as discussed further below, the amount of RBM3 protein in the reference sample does not have to directly correspond to the reference value. The reference sample may also provide an amount of RBM3 protein that helps a person performing the method to assess various reference values. For example, the reference sample(s) may help in creating a mental image of the reference value by providing a "positive" reference value and/or a "negative" reference value.

One alternative for the quantification of RBM3 protein expression in a sample, such as the sample earlier obtained from the subject or the reference sample, is the determination of the fraction of cells in the sample that exhibit RBM3 protein expression over a certain level. The fraction may for example be: a "cellular fraction", wherein the RBM3 protein expression of the whole cells is taken into account; a "cytoplasmic fraction", wherein the RBM3 protein expression of only the cytoplasms of the cells is taken into account; or a "nuclear fraction", wherein the RBM3 protein expression of only the nuclei of the cells is taken into account. The nuclear or cytoplasmic fraction may for example be classified as <2%, 2-25%, >25-75% or >75% immunoreactive cells of the relevant cell population. The "cytoplasmic fraction" corresponds to the percentage of relevant cells in a sample that exhibits a positive staining in the cytoplasm, wherein a medium or distinct and strong immunoreactivity in the cytoplasm is considered positive and no or faint immunoreactivity in the cytoplasm is considered negative. The "nuclear fraction" corresponds to the percentage of relevant cells in a sample that exhibits a positive staining in the nucleus, wherein a medium or distinct and strong immunoreactivity in the nucleus is considered positive and no or faint immunoreactivity in the nucleus is considered negative. The person skilled in the art of pathology understands which cells that are relevant under the conditions present when performing the method and may determine a cytoplasmic or nuclear fraction based on his general knowledge and the teachings of the present disclosure. The relevant cells may for example be tumor cells. Further, the skilled artisan understands how to perform corresponding measurements employing the "cellular fraction".

Another alternative for the quantification of RBM3 protein expression in a sample, such as the sample earlier obtained from the subject or the reference sample, is the determination of the overall staining intensity of the sample. The intensity may for example be: a "cellular intensity", wherein the RBM3 protein expression of the whole cells is taken into account; a "cytoplasmic intensity", wherein the RBM3 protein expression of only the cytoplasms of the cells is taken into account, or a "nuclear intensity", wherein the RBM3 protein expression of only the nuclei of the cells is taken into account. Cytoplasmic and nuclear intensity is subjectively evaluated in accordance with standards used in clinical histopathological diagnostics. Outcome of a cytoplasmic intensity determination may be classified as: absent=no overall immunoreactivity in the cytoplasms of relevant cells of the sample, weak=faint overall immunoreactivity in the cytoplasms of relevant cells of the sample, moderate=medium overall immunoreactivity in the cytoplasms of relevant cells of the sample, or strong=distinct and strong overall immunoreactivity in the cytoplasms of relevant cells of the sample. Outcome of a nuclear intensity determination may be classified as: absent=no overall immunoreactivity in the nuclei of relevant cells of the sample, weak=faint overall immunoreactivity in the nuclei of relevant cells of the sample, moderate=medium overall immunoreactivity in the nuclei of relevant cells of the sample, or strong=distinct and strong overall immunoreactivity in the nuclei of relevant cells of the sample. In some embodiments, the weak and moderate values may be combined into a weak/moderate value (see also Examples, section 4). The person skilled in the art understands which cells that are relevant under the conditions present when performing the method and may determine a nuclear or cytoplasmic intensity based on his general knowledge and the teachings of the present disclosure. The relevant cells may for example be tumor cells. Further, the skilled artisan understands how to perform corresponding measurements employing the "cellular intensity".

The inventors have found that both cytoplasmic and nuclear expression of RBM3 protein is relevant for establishing prognoses.

Thus, in embodiments of the methods of the above aspects, the reference value may be a cytoplasmic fraction, a cytoplasmic intensity or a combination thereof. Accordingly, the sample value may be a cytoplasmic fraction, a cytoplasmic intensity or a combination thereof.

And in further embodiments of the methods of the above aspects, the reference value may be a nuclear fraction, a nuclear intensity or a combination thereof. Accordingly, the sample value may be a nuclear fraction, a nuclear intensity or a combination thereof.

As seen in the figures, in particular FIGS. 2, 4, 11, 15A, 16A and 20A, almost any cytoplasmic fraction, cytoplasmic intensity, nuclear fraction or nuclear intensity may function as a relevant reference value for determining whether the prognosis for survival is relatively good or relatively poor.

Thus, in embodiments of the methods of the above aspects, the criterion for the conclusion in step c) is that the sample value is higher than a nuclear or cytoplasmic fraction of 0%, 1%, 2%, 5%, 10%, 15%, 20%, 25%, 30%, 35%, 40%, 50%, 60%, 70%, 75%, 80%, 90% or 95%.

In alternative or complementing embodiments of the methods of the above aspects, the reference value of step b) is a nuclear or cytoplasmic fraction of 95% or lower, such as 90% or lower, such as 85% or lower, such as 80% or lower, such as 75% or lower, such as 70% or lower, such as 65% or lower, such as 60% or lower, such as 55% or lower, such as 50% or lower, such as 45% or lower, such as 40% or lower, such as 35% or lower, such as 30% or lower, such as 25% or lower, such as 20% or lower, such as 15% or lower, such as 10% or lower, such as 5% or lower, such as 2% or lower, such as 1% or lower, such as 0%.

Further, in embodiments of the methods of the above aspects, the criterion for the conclusion in step c) may be a sample value, which is higher than absent cytoplasmic or nuclear intensity, such as higher than weak cytoplasmic or nuclear intensity, such as higher than moderate cytoplasmic or nuclear intensity. In alternative or complementing embodiments of the methods of the above aspects, the reference value of step b) may be a moderate cytoplasmic or nuclear intensity of RBM3 protein expression or lower, such as a weak cytoplasmic or nuclear intensity of RBM3 protein expression or lower, such as an absent cytoplasmic or nuclear intensity.

A higher reference value may be particularly relevant when the object is to determine whether the tested subject has a particularly good prognosis or is not in need of an adjuvant treatment. For example, a higher reference value may be used for selecting subjects for a "non-treatment strategy". Accordingly, in embodiments of the methods of the above aspects, the reference value may be a nuclear fraction or a cellular fraction of 40-90% RBM3 protein positive cells, such as 50-90% RBM3 protein positive cells, such as 60-90% RBM3 protein positive cells, such as 65-85% RBM3 protein positive cells. In further embodiments of the methods of the above aspects and for the same reasons, the reference value may be a weak/moderate or moderate cytoplasmic or nuclear intensity of.

A lower reference value may be particularly relevant when the object is to determine whether the tested subject has a particularly poor prognosis or is in need of a comparatively aggressive treatment. For example, a lower reference may be used for identifying subjects being in need of a combined adjuvant treatment causing severe side-effects. Accordingly, in embodiments of the methods of the above aspects, the reference value may be a nuclear fraction or a cytoplasmic fraction of 0-25% RBM3 protein positive cells, such as 0-15% RBM3 protein positive cells, such as 0-10% RBM3 protein positive cells, such as 0-5% RBM3 protein positive cells, such as 0-2% RBM3 protein positive cells. In further embodiments of the methods of the above aspects and for the same reasons, the reference value may be an absent cytoplasmic or nuclear intensity.

Thus, the reference value may be any type of intensity or fraction. However, the inventors have found that if the reference value is selected from a nuclear fraction, a nuclear intensity and a cytoplasmic intensity, particularly relevant for conclusions regarding prognoses may be drawn (see the figures).

Alternatively, in embodiments of the methods of the above aspects, the reference value may be a combination of a fraction value and an intensity value.

Also, in embodiments of the methods of the above aspects, the reference value may be a function of a fraction value and an intensity value. For example, such a function may be a staining score. The "staining score" is calculated as described in Examples, Section 4 and table 1 below. For example, the reference value may be a staining score of 2 or lower, such as 1 or lower, such as 0.

The person skilled in the art realizes that another reference value which is an intensity value or a fraction value also fall within the scope of the present invention. Likewise, the person skilled in the art realizes that other combinations of fractions and intensities also fall within the scope of the pre'sent invention. Consequently, the reference value may involve two, and possibly even more, criteria.

In general, the selection of a intensity value and/or a fraction value as the reference value may depend on the staining procedure, e.g., on the employed anti-RBM3 antibody and on the staining reagents.

Guided by the present disclosure, a person skilled in the art, e.g., a pathologist understands how to perform the evaluation yielding a fraction, such as a cellular, cytoplasmic or nuclear fraction, or an intensity, such as a cellular, cytoplasmic or nuclear intensity. For example, the skilled artisan may use a reference sample comprising a predetermined amount of RBM3 protein for establishing the appearance of a certain fraction or intensity.

However, a reference sample may not only be used for the provision of the actual reference value, but also for the provision of an example of a sample with an amount of RBM3 protein that is higher than the amount corresponding to the reference value. As an example, in histochemical staining, such as in immunohistochemical staining, the skilled artisan may use a reference sample for establishing the appearance of a stained sample having a high amount of RBM3 protein, e.g., a positive reference. Subsequently, the skilled artisan may assess the appearances of samples having lower amounts of RBM3 protein, such as the appearance of a sample with an amount of RBM3 protein corresponding to the reference value. In other words, the skilled artisan may use a reference sample to create a mental image of a reference value corresponding to an amount of RBM3 protein which is lower than that of the reference sample. Alternatively, or as a complement, in such assessments, the skilled artisan may use another reference sample having a low amount of RBM3 protein, or lacking detectable RBM3 protein, for establishing the appearance of such sample, e.g., as a "negative reference".

For example, if a reference value of 10% nuclear fraction is used, two reference samples may be employed: a first reference sample having no detectable RBM3 protein, and thus corresponding to a nuclear fraction of 0, which is lower than the reference value; and a second reference sample having an amount of RBM3 protein corresponding to a nuclear fraction of 75% or higher, which is higher than the reference value.

Consequently, in the evaluation, the skilled artisan may use a reference sample for establishing the appearance of a sample with a high amount of RBM3 protein. Such reference sample may be a sample comprising tissue expressing a high amount of RBM3 protein, such as a sample comprising colorectal tumor tissue having a pre-established high expression of RBM3 protein.

Accordingly, the reference sample may provide an example of a strong cytoplasmic intensity (CI). With the knowledge of the appearance of a sample with strong CI, the skilled artisan may then divide samples into the CI categories absent, weak, moderate and strong. This division may be further assisted by a reference sample lacking detectable RBM3 protein (negative reference), i.e., a reference sample providing an absent cytoplasmic intensity. Also, the reference sample may provide an example of a sample with a nuclear fraction (NF) higher than 75%. With the knowledge of the appearance of a sample with more than 75% positive cells, the skilled artisan may then evaluate the NF of other samples having e.g., a lower percentage of positive cells. This division may be further assisted by a reference sample essentially lacking RBM3 protein (negative reference), i.e., a reference sample providing a low NF (e.g., <5%, such as <2%), or a NF of 0.

As mentioned above, cell lines expressing a controlled amount of RBM3 protein may be used as the reference, in particular as a positive reference.

One or more pictures may also be provided as the "reference sample". For example, such a picture may show an example of a tumor tissue slide stained with a certain antibody during certain conditions exhibiting a certain cellular intensity and/or fraction. The above discussion about the "reference sample" applies mutatis mutandis to pictures.

Further, the skilled person should recognize that the usefulness of the methods according to the above aspects is not limited to the quantification of any particular variant of the RBM3 protein present in the subject in question, as long as the protein is encoded by the relevant gene and presents the relevant pattern of expression. As a non-limiting example, the RBM3 protein may comprise, or consists of, a sequence selected from:

i) SEQ ID NO:1; and ii) a sequence which is at least 85% identical to SEQ ID NO:1.

In some embodiments, sequence ii) above is at least 90% identical, at least 91% identical, at least 92% identical, at least 93% identical, at least 94% identical, at least 95% identical, at least 96% identical, at least 97% identical, at least 98% identical or at least 99% identical to SEQ ID NO:1.

As another non-limiting example, the RBM3 protein may comprise, or consists of, a sequence selected from:

i) SEQ ID NO:2; and ii) a sequence which is at least 85% identical to SEQ ID NO:2.

In some embodiments, sequence ii) above is at least 90% identical, at least 91% identical, at least 92% identical, at least 93% identical, at least 94% identical, at least 95% identical, at least 96% identical, at least 97% identical, at least 98% identical or at least 99% identical to SEQ ID NO:2.

The term "% identical", as used in the context of the present disclosure, is calculated as follows. The query sequence is aligned to the target sequence using the CLUSTAL W algorithm (Thompson, J. D., Higgins, D. G. and Gibson, T. J., Nucleic Acids Research, 22: 4673-4680 (1994)). The amino acid residues at each position are compared, and the percentage of positions in the query sequence that have identical correspondences in the target sequence is reported as % identical. Also, the target sequence determines the number of positions that are compared. Consequently, in the context of the present disclosure, a query sequence that is shorter than the target sequence can never be 100% identical to the target sequence. For example, a query sequence of 85 amino acids may at the most be 85% identical to a target sequence of 100 amino acids.

In some embodiments, the methods of the above aspects may comprise a further step preceding step a), which further step comprises:

obtaining biological material from the subject, excising or selecting a relevant part of the biological material to obtain said sample and optionally arranging the sample on a solid phase to facilitate the evaluation of step a). For example, such further step may comprise obtaining tissue material from the colon or rectum of said subject, optionally fixating the tissue material in paraffin or formalin, histo-processing the tissue material to obtain a section which constitute said sample and mounting said sample on a transparent slide, such as a glass slide, for microscopy.

In embodiments of the methods of the aspects above, the RBM3 protein may be detected and/or quantified through the application to the sample of a detectable and/or quantifiable affinity ligand, which is capable of selective interaction with the RBM3 protein. The application of the affinity ligand is performed under conditions that enable binding of the affinity ligand to any RBM3 protein in the sample.

To concretize, in embodiments of the methods of the aspects above, step a) may comprise:

a1) applying to said sample a quantifiable affinity ligand capable of selective interaction with the RBM3 protein to be evaluated, said application being performed under conditions that enable binding of said affinity ligand to RBM3 protein present in said sample;

a2) removing non-bound affinity ligand; and a3) quantifying the affinity ligand remaining in association with said sample to evaluate said amount.

"Affinity ligand remaining in association with the sample" refers to affinity ligand which was not removed in step a2), e.g., the affinity ligand bound to the sample. Here, the binding may for example be the interaction between antibody and antigen.

However, in some embodiments, the removal of non-bound affinity ligand according to a2), e.g. the washing, is not always necessary. Thus, in some embodiments of the methods of the aspects above, step a) may comprise:

aI) applying to said sample a quantifiable affinity ligand capable of selective interaction with the RBM3 protein to be evaluated, said application being performed under conditions that enable binding of said affinity ligand to RBM3 protein present in said sample;

aII) quantifying the affinity bound to said sample to evaluate said amount.

In the context of the present disclosure, "specific" or "selective" interaction of e.g., an affinity ligand with its target or antigen means that the interaction is such that a distinction between specific and non-specific, or between selective and non-selective, interaction becomes meaningful. The interaction between two proteins is sometimes measured by the dissociation constant. The dissociation constant describes the strength of binding (or affinity) between two molecules. Typically the dissociation constant between an antibody and its antigen is from $10^{-7}$ to $10^{-11}$ M. However, high specificity/selectivity does not necessarily require high affinity. Molecules with low affinity (in the molar range) for its counterpart have been shown to be as selective/specific as molecules with much higher affinity. In the case of the present disclosure, a specific or selective interaction refers to the extent to which a particular method can be used to determine the presence and/or amount of a specific protein, the target protein, under given conditions in the presence of other proteins in a tissue sample or fluid sample of a naturally occurring or processed biological fluid. In other words, specificity or selectivity is the capacity to distinguish between related proteins. Specific and selective are sometimes used interchangeably in the present description. For example, the specificity or selectivity of an antibody may be determined as in Examples, Section 2, below, wherein analysis is performed using a protein array set-up, a suspension bead array and a multiplexed competition assay, respectively. Specificity and selectivity determinations are also described in Nilsson P et al. (2005) Proteomics 5:4327-4337.

It is regarded as within the capabilities of those of ordinary skill in the art to select or manufacture the proper affinity ligand and to select the proper format and conditions for detection and/or quantification. Nevertheless, examples of affinity ligands that may prove useful, as well as examples of formats and conditions for detection and/or quantification, are given below for the sake of illustration.

Thus, in embodiments of the present disclosure, the affinity ligand may be selected from the group consisting of antibodies, fragments thereof and derivatives thereof, i.e., affinity ligands based on an immunoglobulin scaffold. The antibodies and the fragments or derivatives thereof may be isolated and/or mono-specific. Antibodies comprise monoclonal and polyclonal antibodies of any origin, including murine, rabbit, human and other antibodies, as well as chimeric antibodies comprising sequences from different species, such as partly humanized antibodies, e.g., partly humanized mouse antibodies. Polyclonal antibodies are produced by immunization of animals with the antigen of choice. Monoclonal antibodies of defined specificity can be produced using the hybridoma technology developed by Köhler and Milstein (Köhler G and Milstein C (1976) Eur. J. Immunol. 6:511-519). The antibody fragments and derivatives of the present disclosure are capable of selective interaction with the same antigen (e.g.

RBM3 protein) as the antibody they are fragments or derivatives of. Antibody fragments and derivatives comprise Fab fragments, consisting of the first constant domain of the heavy chain (CH1), the constant domain of the light chain (CL), the variable domain of the heavy chain (VH) and the variable domain of the light chain (VL) of an intact immunoglobulin protein; Fv fragments, consisting of the two variable antibody domains VH and VL (Skerra A and Pluckthun A (1988) Science 240:1038-1041); single chain Fv fragments (scFv), consisting of the two VH and VL domains linked together by a flexible peptide linker (Bird R E and Walker B W (1991) Trends Biotechnol. 9:132-137); Bence Jones dimers (Stevens F J et al. (1991) Biochemistry 30:6803-6805); camelid heavy-chain dimers (Hamers-Casterman C et al. (1993) Nature 363:446-448) and single variable domains (Cai X and Garen A (1996) Proc. Natl. Acad. Sci. U.S.A. 93:6280-6285; Masat L et al. (1994) Proc. Natl. Acad. Sci. U.S.A. 91:893-896), and single domain scaffolds like e.g., the New Antigen Receptor (NAR) from the nurse shark (Dooley H et al. (2003) Mol. Immunol. 40:25-33) and minibodies based on a variable heavy domain (Skerra A and Plückthun A (1988) Science 240:1038-1041).

SEQ ID NO:1 was designed for immunizations, e.g., designed to lack transmembrane regions to ensure efficient expression in *E. coli*, and to lack any signal peptide, since those are cleaved off in the mature protein. Consequently, an antibody or fragment or derivative thereof according to the present disclosure may for example be one that is obtainable by a process comprising a step of immunizing an animal, such as a rabbit, with a protein whose amino acid sequence comprises, preferably consists of, the sequence SEQ ID NO:1. For example, the immunization process may comprise primary immunization with the protein in Freund's complete adjuvant. Also, the immunization process may further comprise boosting at least two times, in intervals of 2-6 weeks, with the protein in Freund's incomplete adjuvant. Processes for the production of antibodies or fragments or derivatives thereof against a given target are known in the art.

Further, an antibody or fragment or derivative thereof according to the present disclosure may be obtainable by a process comprising a step of immunizing an animal with a peptide whose amino acid sequence consists of a sequence selected from SEQ ID NO:4 and SEQ ID NO:5. Also, the antibody or fragment may be obtainable by a process comprising a step of immunizing an animal with an RBM3 fragment which consists of 20 amino acids or less, such as 15 amino acids or less, and comprises a sequence selected from SEQ ID NO:6-19. For a further discussion about SEQ ID NO:4-19, see below.

In the context of the present disclosure, a "mono-specific antibody" is one of a population of polyclonal antibodies which has been affinity purified on its own antigen, thereby separating such mono-specific antibodies from other antiserum proteins and non-specific antibodies. This affinity purification results in antibodies that bind selectively to its antigen. In the case of the present disclosure, the polyclonal antisera are purified by a two-step immunoaffinity based protocol to obtain mono-specific antibodies selective for the target protein. Antibodies directed against generic affinity tags of antigen fragments are removed in a primary depletion step, using the immobilized tag protein as the capturing agent. Following the first depletion step, the serum is loaded on a second affinity column with the antigen as capturing agent, in order to enrich for antibodies specific for the antigen (see also Nilsson P et al. (2005) Proteomics 5:4327-4337).

Polyclonal and monoclonal antibodies, as well as their fragments and derivatives, represent the traditional choice of affinity ligands in applications requiring selective biomolecular recognition, such as in the detection and/or quantification of RBM3 protein according to the method aspects above. However, those of skill in the art know that, due to the increasing demand of high throughput generation of selective binding ligands and low cost production systems, new biomolecular diversity technologies have been developed during the last decade. This has enabled a generation of novel types of affinity ligands of both immunoglobulin as well as non-immunoglobulin origin that have proven equally useful as binding ligands in biomolecular recognition applications and can be used instead of, or together with, immunoglobulins.

The biomolecular diversity needed for selection of affinity ligands may be generated by combinatorial engineering of one of a plurality of possible scaffold molecules, and specific and/or selective affinity ligands are then selected using a suitable selection platform. The scaffold molecule may be of immunoglobulin protein origin (Bradbury A R and Marks J D (2004) J. Immunol. Meths. 290:29-49), of non-immunoglobulin protein origin (Nygren PÅ and Skerra A (2004) J. Immunol. Meths. 290:3-28), or of an oligonucleotide origin (Gold L at al. (1995) Annu. Rev. Biochem. 64:763-797).

A large number of non-immunoglobulin protein scaffolds have been used as supporting structures in development of novel binding proteins. Non-limiting examples of such structures, useful for generating affinity ligands against RBM3 protein for use according to the present disclosure, are staphylococcal protein A and domains thereof and derivatives of these domains, such as protein Z (Nord K et al. (1997) Nat. Biotechnol. 15:772-777); lipocalins (Beste G et al. (1999) Proc. Natl. Acad. Sci. U.S.A. 96:1898-1903); ankyrin repeat domains (Binz H K et al. (2003) J. Mol. Biol. 332:489-503); cellulose binding domains (CBD) (Smith G P et al. (1998) J. Mol. Biol. 277:317-332; Lehtio J et al. (2000) Proteins 41:316-322); γ crystallines (Fiedler U and Rudolph R, WO01/04144); green fluorescent protein (GFP) (Peelle B et al. (2001) Chem. Biol. 8:521-534); human cytotoxic T lymphocyte-associated antigen 4 (CTLA-4) (Hufton S E et al. (2000) FEBS Lett. 475:225-231; Irving R A et al. (2001) J. Immunol. Meth. 248:31-45); protease inhibitors, such as Knottin proteins (Wentzel A et al. (2001) J. Bacteriol. 183:7273-7284; Baggio R et al. (2002) J. Mol. Recognit. 15:126-134) and Kunitz domains (Roberts B L et al. (1992) Gene 121:9-15; Dennis M S and Lazarus R A (1994) J. Biol. Chem. 269:22137-22144); PDZ domains (Schneider S et al. (1999) Nat. Biotechnol. 17:170-175); peptide aptamers, such as thioredoxin (Lu Z et al. (1995) Biotechnology 13:366-372; Klevenz B et al. (2002) Cell. Mol. Life Sci. 59:1993-1998); staphylococcal nuclease (Norman T C et al. (1999) Science 285:591-595); tendamistats (McConell S J and Hoess R H (1995) J. Mol. Biol. 250:460-479; Li R et al. (2003) Protein Eng. 16:65-72); trinectins based on the fibronectin type III domain (Koide A et al. (1998) J. Mol. Biol. 284:1141-1151; Xu L et al. (2002) Chem. Biol. 9:933-942); and zinc fingers (Bianchi E et al. (1995) J. Mol. Biol. 247:154-160; Klug A (1999) J. Mol. Biol. 293:215-218; Segal D J et al. (2003) Biochemistry 42:2137-2148).

The above-mentioned examples of non-immunoglobulin protein scaffolds include scaffold proteins presenting a single randomized loop used for the generation of novel binding specificities, protein scaffolds with a rigid secondary structure where side chains protruding from the protein surface are randomized for the generation of novel binding specificities, and scaffolds exhibiting a non-contiguous hyper-variable loop region used for the generation of novel binding specificities.

In addition to non-immunoglobulin proteins, oligonucleotides may also be used as affinity ligands. Single stranded nucleic acids, called aptamers or decoys, fold into well-defined three-dimensional structures and bind to their target with high affinity and specificity. (Ellington A D and Szostak J W (1990) Nature 346:818-822; Brody E N and Gold L (2000) J. Biotechnol. 74:5-13; Mayer G and Jenne A (2004) BioDrugs 18:351-359). The oligonucleotide ligands can be either RNA or DNA and can bind to a wide range of target molecule classes.

For selection of the desired affinity ligand from a pool of variants of any of the scaffold structures mentioned above, a number of selection platforms are available for the isolation of a specific novel ligand against a target protein of choice. Selection platforms include, but are not limited to, phage display (Smith G P (1985) Science 228:1315-1317), ribosome display (Hanes J and Plikkthun A (1997) Proc. Natl. Acad. Sci. U.S.A. 94:4937-4942), yeast two-hybrid system (Fields S and Song 0 (1989) Nature 340:245-246), yeast display (Gai S A and Wittrup K D (2007) Curr Opin Struct Biol 17:467-473), mRNA display (Roberts R W and Szostak J W (1997) Proc. Natl. Acad. Sci. U.S.A. 94:12297-12302), bacterial display (Daugherty P S (2007) Curr Opin Struct Biol 17:474-480, Kronqvist N et al. (2008) Protein Eng Des Sel 1-9, Harvey B R et al. (2004) PNAS 101(25):913-9198), microbead display (Nord 0 et al. (2003) J Biotechnol 106:1-13, WO01/05808), SELEX (System Evolution of Ligands by Exponential Enrichment) (Tuerk C and Gold L (1990) Science 249:505-510) and protein fragment complementation assays (PCA) (Remy I and Michnick S W (1999) Proc. Natl. Acad. Sci. U.S.A. 96:5394-5399).

Thus, in embodiments of the present disclosure, the affinity ligand may be a non-immunoglobulin affinity ligand derived from any of the protein scaffolds listed above, or an oligonucleotide molecule.

The RBM3 protein fragment SEQ ID NO:1 was designed to consist of a unique sequence with low homology with other human proteins and to minimize cross reactivity of generated affinity reagents. Consequently, in embodiments of the present disclosure, the affinity ligand may be capable of selective interaction with a polypeptide consisting of the sequence SEQ ID NO:1.

Further, as described below under Examples, Section 5, two epitope regions (SEQ ID NO:4 and SEQ ID NO:5) have been identified within SEQ ID NO:1. The relevance of SEQ ID NO:4 is for example confirmed in Examples, Sections 9 and 12. The relevance of SEQ ID NO:5 is for example confirmed in Examples, Section 7. Thus, in some embodiments, the affinity ligand of the present disclosure is capable of selective interaction with a peptide consisting of an amino acid sequence selected from SEQ ID NO:4 and SEQ ID NO:5.

As an example, antibodies capable of selective interaction with SEQ ID NO:4 and SEQ ID NO:5 may be obtained by immunizing an animal with an antigen consisting of the amino acid sequence SEQ ID NO:1 followed by affinity purification of the antisera using peptides consisting of the amino acid sequences SEQ ID NO:4 and SEQ ID NO:5, respectively.

Further, as described above under Examples, Section 6, another four epitope regions (SEQ ID NO:6-9) have been identified. Thus, in some embodiments, the affinity ligand of the present disclosure is capable of selective interaction with an RBM3 fragment which consists of 20 amino acids or less, such as 15 amino acids or less, and comprises a sequence selected from SEQ ID NO:6-9.

Also, as described above under Examples, Section 7, another ten epitope regions (SEQ ID NO:10-19) have been identified. Thus, in some embodiments, the affinity ligand of the present disclosure is capable of selective interaction with an RBM3 fragment which consists of 20 amino acids or less, such as 15 amino acids or less, and comprises a sequence selected from SEQ ID NO:10-19.

Figure 14:
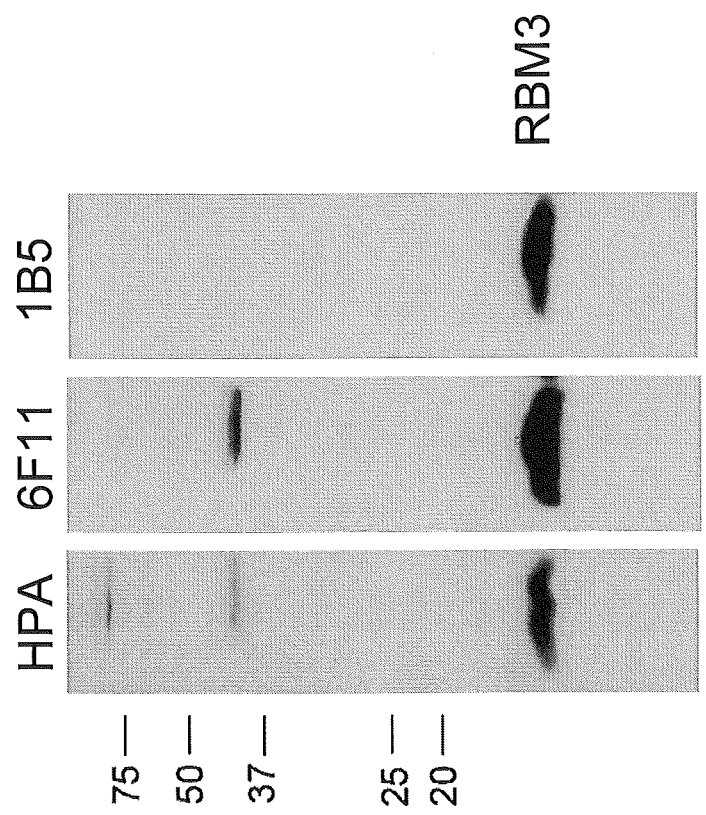
FIG. 14 shows Western blot results for Anti-RBM3, 1B5 and 6F11.

Antibodies having selectivity for a single epitope region (such as monoclonal antibodies) may provide for increased reproducibility in detection analyses as compared to antibodies generated against a longer peptide sequence (such as a PrEST or a full-length protein). The antibodies selective for a single epitope region may also provide for distinct and strong staining in immunohistochemical analyses. These benefits, independently or jointly, may be valuable when establishing prognoses and making decisions regarding treatments according to the present disclosure. In FIG. 14, a benefit (increased selectivity) of monoclonal antibodies according to the present disclosure as compared to a polyclonal antibody is illustrated.

The monoclonal antibodies 6F11 and 1B5 are considered to be particularly beneficial. In FIG. 14, 6F11 and 1B5 are both shown to be more selective than a polyclonal anti-RBM3 antibody. Further, 1B5 is shown to be more selective than 6F11. 1B5 is also employed in Examples, Section 4 below.

SEQ ID NO:17, to which 1B5 is shown to bind in Examples, Section 7, is within SEQ ID NO:5. In preferred embodiments of the present disclosure, the affinity ligand is thus capable of selective interaction with an RBM3 fragment which consists of SEQ ID NO:5, and in particularly preferred embodiments of the present disclosure, the affinity ligand is capable of selective interaction with an RBM3 fragment which consists of 20 amino acids or less, such as 15 amino acids or less, and comprises the sequence SEQ ID NO:17.

6F11 is shown to bind to SEQ ID NO:8 and SEQ ID NO:16. In other preferred embodiments of the present disclosure, the affinity ligand is thus capable of selective interaction with an RBM3 fragment which consists of 20 amino acids or less, such as 15 amino acids or less, and comprises a sequence selected from SEQ ID NO:8 and 16. Note that SEQ ID NO:8 and 16 are overlapping and that such a fragment may comprise the sequences of both SEQ ID NO:8 and 16.

The detection and/or quantification of the affinity ligand capable of selective interaction with the RBM3 protein may be accomplished in any way known to the skilled person for detection and/or quantification of binding reagents in assays based on biological interactions. Accordingly, any affinity ligand described above may be used to quantitatively and/or qualitatively detect the presence of the RBM3 protein. These "primary" affinity ligands may be labeled themselves with various markers or may in turn be detected by secondary, labeled affinity ligands to allow detection, visualization and/or quantification. This can be accomplished using any one or more of a multitude of labels, which can be conjugated to the affinity ligand capable of interaction with RBM3 protein or to any secondary affinity ligand, using any one or more of a multitude of techniques known to the skilled person, and not as such involving any undue experimentation.

Non-limiting examples of labels that can be conjugated to primary and/or secondary affinity ligands include fluorescent dyes or metals (e.g., fluorescein, rhodamine, phycoerythrin, fluorescamine), chromophoric dyes (e.g., rhodopsin), chemiluminescent compounds (e.g., luminal, imidazole) and bioluminescent proteins (e.g., luciferin, luciferase), haptens (e.g., biotin). A variety of other useful fluorescers and chromophores are described in Stryer L (1968) Science 162:526-533 and Brand L and Gohlke J R (1972) Annu. Rev. Biochem.

41:843-868. Affinity ligands can also be labeled with enzymes (e.g., horseradish peroxidase, alkaline phosphatase, beta-lactamase), radioisotopes (e.g., $^3$H, $^{14}$C, $^{32}$P, $^{35}$S or $^{125}$I) and particles (e.g., gold). In the context of the present disclosure, "particles" refer to particles, such as metal particles, suitable for labeling of molecules. Further, the affinity ligands may also be labeled with fluorescent semiconductor nanocrystals (quantum dots). Quantum dots have superior quantum yield and are more photostable compared to organic fluorophores and are therefore more easily detected (Chan et al. (2002) *Curr Opi Biotech*. 13: 40-46). The different types of labels can be conjugated to an affinity ligand using various chemistries, e.g., the amine reaction or the thiol reaction. However, other reactive groups than amines and thiols can be used, e.g., aldehydes, carboxylic acids and glutamine.

The method aspects above may be put to use in any of several known formats and set-ups, of which a non-limiting selection is discussed below.

In a set-up based on histology, the detection, localization and/or quantification of a labeled affinity ligand bound to its RBM3 protein target may involve visualizing techniques, such as light microscopy or immunofluorescence microscopy. Other methods may involve the detection via flow cytometry or luminometry.

A biological sample, such as a tumor tissue sample (biopsy), for example from colorectal tissue, which has been removed from the subject may be used for detection and/or quantification of RBM3 protein or RBM3 mRNA. The biological sample, such as the biopsy, may be an earlier obtained sample. If using an earlier obtained sample in a method, no steps of the method are practiced on the human or animal body. The affinity ligand may be applied to the biological sample for detection and/or quantification of RBM3 protein. This procedure enables not only detection of RBM3 protein, but may in addition show the distribution and relative level of expression thereof.

The method of visualization of labels on the affinity ligand may include, but is not restricted to, fluorometric, luminometric and/or enzymatic techniques. Fluorescence is detected and/or quantified by exposing fluorescent labels to light of a specific wavelength and thereafter detecting and/or quantifying the emitted light in a specific wavelength region. The presence of a luminescently tagged affinity ligand may be detected and/or quantified by luminescence developed during a chemical reaction. Detection of an enzymatic reaction is due to a color shift in the sample arising from chemical reaction. Those of skill in the art are aware that a variety of different protocols can be modified in order for proper detection and/or quantification.

In embodiments of the methods of the above aspects, a biological sample may be immobilized onto a solid phase support or carrier, such as nitrocellulose or any other solid support matrix capable of immobilizing RBM3 protein present in the biological sample applied to it. Some well-known solid state support materials useful in the present invention include glass, carbohydrate (e.g., Sepharose), nylon, plastic, wool, polystyrene, polyethene, polypropylene, dextran, amylase, films, resins, cellulose, polyacrylamide, agarose, alumina, gabbros and magnetite. After immobilization of the biological sample, primary affinity ligand specific to RBM3 protein may be applied, e.g., as described in Examples, Sections 4, of the present disclosure. If the primary affinity ligand is not labeled in itself, the supporting matrix may be washed with one or more appropriate buffers known in the art, followed by exposure to a secondary labeled affinity ligand and washed once again with buffers to remove unbound affinity ligands. Thereafter, selective affinity ligands may be detected and/or quantified with conventional methods. The binding properties for an affinity ligand may vary from one solid state support to the other, but those skilled in the art should be able to determine operative and optimal assay conditions for each determination by routine experimentation.

Consequently, in embodiments of the methods of the above aspects, the quantifiable affinity ligand of a1) or aI) may be detected using a secondary affinity ligand capable of recognizing the quantifiable affinity ligand. The quantification of a3) or aII) may thus be carried out by means of a secondary affinity ligand with affinity for the quantifiable affinity ligand. As an example, the secondary affinity ligand may be an antibody or a fragment or a derivative thereof.

As an example, one available method for detection and/or quantification of the RBM3 protein is by linking the affinity ligand to an enzyme that can then later be detected and/or quantified in an enzyme immunoassay (such as an EIA or ELISA). Such techniques are well established, and their realization does not present any undue difficulties to the skilled person. In such methods, the biological sample is brought into contact with a solid material or with a solid material conjugated to an affinity ligand against the RBM3 protein, which is then detected and/or quantified with an enzymatically labeled secondary affinity ligand. Following this, an appropriate substrate is brought to react in appropriate buffers with the enzymatic label to produce a chemical moiety, which for example is detected and/or quantified using a spectrophotometer, fluorometer, luminometer or by visual means.

As stated above, primary and any secondary affinity ligands can be labeled with radioisotopes to enable detection and/or quantification. Non-limiting examples of appropriate radiolabels in the present disclosure are $^3$H, $^{14}$C, $^{35}$S or $^{125}$I. The specific activity of the labeled affinity ligand is dependent upon the half-life of the radiolabel, isotopic purity, and how the label has been incorporated into the affinity ligand. Affinity ligands are preferably labeled using well-known techniques (Wensel T G and Meares C F (1983) in: *Radioimmunoimaging and Radioimmunotherapy* (Burchiel S W and Rhodes B A eds.) Elsevier, New York, pp 185-196). A thus radiolabeled affinity ligand can be used to visualize RBM3 protein by detection of radioactivity in vivo or in vitro. Radionuclear scanning with e.g., gamma camera, magnetic resonance spectroscopy or emission tomography function for detection in vivo and in vitro, while gamma/beta counters, scintillation counters and radiographies are also used in vitro.

In the Examples below, the protein expression of the RBM3 gene is detected and found to correlate with the outcome of colorectal cancer. However, the present disclosure also encompasses the mRNA expression of the RBM3 gene as the inventors have found the RBM3 mRNA level and the RBM3 protein level to co-vary in other types of cancer tissue in which RBM3 is also of prognostic significance.

Methods for detecting and quantifying biomarkers on the mRNA level are well known within the art.

According to one such method, total cellular RNA is purified from cells by homogenization in the presence of nucleic acid extraction buffer, followed by centrifugation. Nucleic acids are then precipitated, in order to remove DNA by treatment with DNase and precipitation. The RNA molecules are then separated by gel electrophoresis on agarose gels according to standard techniques, and transferred to nitrocellulose filters by, e.g., the so-called "Northern" blotting technique. The RNA is then immobilized on the filters by heating. Detection and quantification of specific RNA is accomplished using appropriately labeled DNA or RNA probes complementary to the RNA in question. See, for example, Molecular Cloning: A Laboratory Manual (Sambrook J. et al., (1989) 2nd edition, Cold Spring Harbor Laboratory Press). Methods for the preparation of labeled DNA and RNA probes, and the conditions for hybridization thereof to target nucleotide sequences, are described in Molecular Cloning: A Laboratory Manual (Sambrook J. et al., (1989) 2nd edition, Cold Spring Harbor Laboratory Press). For example, the nucleic acid probe may be labeled with, e.g., a radionuclide such as $^3H$, $^{32}P$, $^{33}P$, $^{14}C$, or $^{35}S$; a heavy metal; or a ligand capable of functioning as a specific binding pair member for a labeled ligand (e.g., biotin, avidin, or an antibody), a fluorescent molecule, a chemiluminescent molecule, an enzyme, or the like.

Probes may be labeled to high specific activity by either the nick translation method (Rigby et al., (1977) J. Mol Biol, 113: 237-251), or by the random priming method (Fienberg, (1983) Anal. Biochem., 132: 6-13). The latter can be a method for synthesizing $^{32}P$-labeled probes of high specific activity from RNA templates. For example, by replacing preexisting nucleotides with highly radioactive nucleotides according to the nick translation method, it is possible to prepare $^{32}P$-labeled nucleic acid probes with a specific activity well in excess of 10 cpm/microgram. Autoradiographic detection of hybridization then can be performed by exposing hybridized filters to photographic film. Densitometric scanning of the photographic films exposed by the hybridized filters provides an accurate measurement of biomarker levels. Using another approach, biomarker levels can be quantified by computerized imaging systems, such as the Molecular Dynamics 400-B 2D Phosphorimager (Amersham Biosciences, Piscataway, N.J., USA).

Where radionuclide labeling of DNA or RNA probes is not practical, the random-primer method can be used to incorporate an analogue, for example, the dTTP analogue 5-(N—(N-biotinyl-epsilon-aminocaproyl)-3-aminoallyl)deoxyuridine triphosphate, into the probe molecule. The biotinylated probe oligonucleotide can be detected by reaction with biotin-binding proteins, such as avidin, streptavidin, and antibodies (e.g., anti-biotin antibodies) coupled to fluorescent dyes or enzymes that produce color reactions.

In addition to Northern and other RNA blotting hybridization techniques, determining the levels of RNA transcript may be accomplished using the technique of in situ hybridization. This technique requires fewer cells than the Northern blotting technique, and involves depositing whole cells onto a microscope cover slip and probing the nucleic acid content of the cell with a solution containing radioactive or otherwise labeled nucleic acid (e.g., cDNA or RNA) probes. This technique is particularly well-suited for analyzing tissue biopsy samples from subjects.

The relative number of RNA transcripts in cells can also be determined by reverse transcription of RNA transcripts, followed by amplification of the reverse-transcribed transcripts by polymerase chain reaction (RT-PCR). The levels of RNA transcripts can be quantified in comparison with an internal standard, for example, the level of mRNA from a standard gene present in the same sample. The person skilled in the art is capable of selecting suitable genes for use as an internal standard. The methods for quantitative RT-PCR and variations thereof are within the skill in the art.

Any suitable primers can be used for the quantitative RT-PCR. Preferably, the primers are specific to RBM3 It is within the skill in the art to generate primers specific to RBM3 (e.g. starting from SEQ ID NO:3). Primers can be of any suitable length, but are preferably between 19 and 23 (e.g., 19, 20, 21, 22, or 23) nucleotides. Ideally, amplicon length should be 50 to 150 (up to 250 may be necessary but then optimization of the thermal cycling protocol and reaction components may be necessary) bases for optimal PCR efficiency. Designing primers that generate a very long amplicon may lead to poor amplification efficiency. Information about primer design and optimal amplicon size may for example be found at www.ambion.com.

In some instances, it may be desirable to use microchip technology to detect biomarker expression. The microchip can be fabricated by techniques known in the art. For example, probe oligonucleotides of an appropriate length, e.g., 40 nucleotides, are 5'-amine modified at position C6 and printed using commercially available microarray systems, e.g., the GENEMACHINE OmniGrid 100 Microarrayer and Amersham CODELINK activated slides. Labeled cDNA oligomer corresponding to the target RNAs is prepared by reverse transcribing the target RNA with labeled primer. Following first strand synthesis, the RNA/DNA hybrids are denatured to degrade the RNA templates. The labeled target cDNAs thus prepared are then hybridized to the microarray chip under hybridizing conditions, e.g., 6 times SSPE/30% formamide at 25° C. for 18 hours, followed by washing in 0.75 times TNT at 37° C. for 40 minutes. At positions on the array, where the immobilized probe DNA recognizes a complementary target cDNA in the sample, hybridization occurs. The labeled target cDNA marks the exact position on the array where binding occurs, thereby allowing automatic detection and quantification. The output consists of a list of hybridization events, which indicate the relative abundance of specific cDNA sequences, and therefore the relative abundance of the corresponding complementary biomarker, in the subject sample. According to one embodiment, the labeled cDNA oligomer is a biotin-labeled cDNA prepared from a biotin-labeled primer. The microarray is then processed by direct detection of the biotin-containing transcripts using, e.g., Streptavidin-Alexa647 conjugate, and scanned utilizing conventional scanning methods. Image intensities of each spot on the array are proportional to the abundance of the corresponding biomarker in the subject sample.

The use of the array has one or more advantages for mRNA expression detection. First, the global expression of several to thousands of genes can be identified in a single sample at one time. Second, through careful design of the oligonucleotide probes, the expression of both mature and precursor molecules can be identified. Third, in comparison with Northern blot analysis, the chip requires a small amount of RNA.

The RBM3 mRNA (as well as the RBM3 protein) may for example be extracted from formalin-fixed, paraffin-embedded tumor tissue. Accordingly, the sample of the methods of the present disclosure may be formalin-fixed and/or paraffin-embedded colorectal tumor tissue.

The inventors have realized that the RBM3 mRNA analysis of the present disclosure may be incorporated in an oncotypeDX® assay, such as the oncotypeDX® colon cancer assay, which is designed to predict the risk of recurrence and support individualized treatment planning and employs RT-PCR to analyze the expression of several genes.

As explained herein, RBM3 is a relevant biomarker for colorectal cancer subjects. Thus, as a configuration of the present disclosure, there is provided a method in which, in one or more sample(s) from a subject having or suspected of having a colorectal cancer, the levels of expression of the RBM3 gene and one or more of the following genes is analyzed:

KI-67, C-MYC, MYBL2, FAP, BGN, INHBA, GADD45B, ATP5E, PGK1, GPX1, UBB and VDAC2.

All these genes are included in the gene panel of the oncotypeDX® colon cancer assay.

As another configuration of the present disclosure, there is provided a method in which, in one or more sample(s) from a subject having or suspected of having a colorectal cancer, the levels of expression of the RBM3 gene and one or more of the following genes is analyzed:

Multiple C2 domainstransmembrane 1 (MCTP1), Laminin alpha 3 (LAMAS), Cathepsin C (CTSC), Pyridine nucleotide-disulphideoxioreductase domain 1 (PYROX D1), ER degradation enhancer mannosidase alpha-like 1 (EDEM1), Interleukin-2 receptor beta (IL2RB), Zinc finger protein 697 (ZNF697), Solute carrier family 6 member 11 (SLC6A11), Interleukin-2 receptor alpha IL2RA, Cytoplasmic FMR1 interacting protein 2 (CYFIP2), Pim-3 oncogene (PIM3), Leukemia inhibitory factor (LIF), Mannose-6-phosphate receptor binding protein 1/Perilipin 3 (PLIN3), hydroxy-delta-5-steroid dehydrogenase 3 beta- and steroid delta-isomerase 1 (HSD3B1), zinc finger BED-type containing 4 (ZBED4), peroxisome proliferator-activated receptor alpha (PPARA), threonine synthase-like 2 (*S. cerevisiae*) (THNSL2) and CA438802.

Most, if not all, of these genes are included in the ColoPrint® test.

In some embodiments, the expression of at least two of the above genes is analyzed together with RBM3.

Further embodiments of the configuration are evident to the skilled person from the present disclosure.

As a third aspect of the present disclosure, there is provided a kit for carrying out a method according to the above aspects, which comprises:

a) a quantifiable affinity ligand capable of selective interaction with an RBM3 protein; and b) reagents necessary for quantifying the amount of said quantifiable affinity ligand.

Various components of the kit according to the third aspect may be selected and specified as described above in connection with the method aspects of the present disclosure.

Thus, the kit according to the present disclosure comprises an affinity ligand against an RBM3 protein, as well as other means that help to quantify the specific and/or selective affinity ligand after it has bound specifically and/or selectively to the RBM3 protein. For example, the kit may contain a secondary affinity ligand for detecting and/or quantifying a complex formed by the RBM3 protein and the affinity ligand capable of selective interaction with the RBM3 protein. The kit may also contain various auxiliary substances other than affinity ligands, to enable the kit to be used easily and efficiently. Examples of auxiliary substances include solvents for dissolving or reconstituting lyophilized protein components of the kit, wash buffers, substrates for measuring enzyme activity in cases where an enzyme is used as a label, target retrieval solution to enhance the accessibility to antigens in cases where paraffin or formalin-fixed tissue samples are used, and substances such as reaction arresters, e.g., endogenous enzyme block solution to decrease the background staining and/or counterstaining solution to increase staining contrast, that are commonly used in immunoassay reagent kits.

In embodiments of the kit aspect, the affinity ligand may be selected as described above in connection with the method aspects.

Further, in accordance with what is described above in connection with the method aspects, the detectable affinity ligand may in embodiments of the kit aspect comprise a label selected from the group consisting of fluorescent dyes and metals, chromophoric dyes, chemiluminescent compounds and bioluminescent proteins, enzymes, radioisotopes, particles and quantum dots. Alternatively, the reagents necessary for quantifying the amount of the affinity ligand comprise a secondary affinity ligand capable of recognizing the quantifiable affinity ligand. As an example, the secondary affinity ligand capable of recognizing the quantifiable affinity ligand comprises a label selected from the group consisting of fluorescent dyes or metals, chromophoric dyes, chemiluminescent compounds and bioluminescent proteins, enzymes, radioisotopes, particles and quantum dots.

The kit according to the kit aspect may also advantageously comprise a reference sample for provision of, or yielding, the reference value to be used for comparison with the sample value. For example, the reference sample may comprise a predetermined amount of RBM3 protein. Such a reference sample may for example be constituted by a tissue sample containing the predetermined amount of RBM3 protein. The tissue reference sample may then be used by the person of skill in the art in the determination of the RBM3 expression status in the sample being studied, by manual, such as ocular, or automated comparison of expression levels in the reference tissue sample and the subject sample. As another example, the reference sample may comprise cell lines, such as cancer cell lines, expressing a predetermined, or controlled, amount of RBM3 protein. The person skilled in the art understands how to provide such cell lines, for example guided by the disclosure of Rhodes et al. (2006) The biomedical scientist, p 515-520. As an example, the cell lines may be formalin fixed. Also, such formalin fixed cell lines may be paraffin embedded.

The wording "reference sample for provision of the reference value" is to be interpreted broadly in the context of the present disclosure. The reference sample may comprise an amount of RBM3 protein actually corresponding to the reference value, but it may also comprise an amount of RBM3 protein corresponding to a value being higher than the reference value. In the latter case, the "high" value may be used by a person performing the method as an upper reference (positive reference) for assessing, e.g., the appearance of, a reference value which is lower than the "high" value. The person skilled in the art of immunohistochemistry understands how to do such an assessment. Further, as an alternative or a complementing example, the skilled person may use another reference sample comprising a low amount of RBM3 protein for provision of a "low" value in such an assessment, e.g., as a negative reference. This is further discussed above in connection with the method aspects.

Consequently, in embodiments of the kit aspect, the reference sample may comprise an amount of RBM3 protein corresponding to the reference value. As an example, the reference sample may comprise an amount of RBM3 protein corresponding to a nuclear or cytoplasmic fraction of 95% or lower, such as 90% or lower, such as 85% or lower, such as 80% or lower, such as 75% or lower, such as 70% or lower, such as 65% or lower, such as 60% or lower, such as 55% or lower, such as 50% or lower, such as 45% or lower, such as 40% or lower, such as 35% or lower, such as 30% or lower, such as 25% or lower, such as 20% or lower, such as 15% or lower, such as 10% or lower, such as 5% or lower, such as 2% or lower, such as 1% or lower, such as 0%.

Alternatively, or as a complement, the reference sample may comprise an amount of RBM3 protein corresponding to a moderate nuclear or cytoplasmic intensity expression or lower, such as a weak nuclear or cytoplasmic intensity of RBM3 protein expression or lower, such as an absent nuclear or cytoplasmic intensity.

As mentioned above, a higher reference value may be particularly relevant when the object is to determine whether the tested subject has a particularly good prognosis or is not in need of an adjuvant treatment. Accordingly, the reference sample may comprise an amount of RBM3 protein corresponding to a nuclear or cytoplasmic fraction of 40-90%, such as 50-90%, such as 60-90%, such as 65-85%. In further embodiments, the reference sample may comprise an amount of RBM3 protein corresponding to a weak/moderate or moderate nuclear or cytoplasmic intensity. As also mentioned above, a lower reference value may be particularly relevant when the object is to determine whether the tested subject has a particularly poor prognosis or is in need of an aggressive adjuvant treatment. Accordingly, the reference sample may comprise an amount of RBM3 protein corresponding to a nuclear or cytoplasmic fraction of 0-25%, such as 0-15%, such as 0-10%, such as 0-5%, such as 0-2%. In further embodiments, the reference sample may comprise an amount of RBM3 protein corresponding to an absent nuclear or cytoplasmic intensity. Further, the reference sample may comprise an amount of RBM3 protein corresponding to a staining score of 0, 1 or 2 (see table 1).

The provision of fraction values and intensity values is discussed above in connection with the method aspects.

Further, in alternative or complementing embodiments of the kit aspect, the kit may comprise a reference sample comprising an amount of RBM3 protein corresponding to a value being higher than the reference value. In these embodiments, the reference sample may for example comprise an amount of RBM3 protein corresponding to a nuclear or cytoplasmic fraction of 75% or higher and/or a strong nuclear or cytoplasmic intensity.

In other alternative or complementing embodiments of the kit aspect, the kit may comprise a reference sample comprising an amount of RBM3 protein corresponding to a value being lower than or equal to the reference value, e.g., an absent nuclear or cytoplasmic intensity and/or a nuclear or cytoplasmic fraction of <2% RBM3 protein positive cells, such as 0% RBM3 protein positive cells.

The kit may thus comprise: a reference sample comprising an amount of RBM3 protein corresponding to a predetermined reference value; a reference sample comprising an amount of RBM3 protein corresponding to a value being higher than a predetermined reference value; and/or a reference sample comprising an amount of RBM3 protein corresponding to a value being lower than or equal to a predetermined reference value.

Consequently, embodiments of the kit may comprise: a first reference sample comprising an amount of RBM3 protein being higher than a predetermined reference value; and a second reference sample comprising an amount of RBM3 protein being lower than or equal to the predetermined reference value.

In embodiments of the kit aspect, the reference sample may be a tissue sample, such as a tissue sample adapted to ocular or microscopic evaluation. As an example, the tissue reference sample may be fixated in paraffin or buffered formalin and/or histo-processed to sections (e.g., µm-thin sections) that are mounted on microscopic glass-slides. The tissue reference sample may be further adapted to staining with affinity ligands, such as antibodies, against an RBM3 protein.

Consequently, in embodiments of the kit aspect, the reference sample may be adapted to directly, or indirectly, provide any relevant reference value, such as any one of the reference values discussed above.

Further embodiments of the reference sample of the kit aspect are discussed above in connection with the reference values and reference samples of the method aspects.

RBM3 may also be detected on the mRNA level. Such detection may for example be an in situ mRNA analysis or a quantitative RT-PCR mRNA analysis. Further, the mRNA of a sample may be copied into cDNA to increase stability prior to detection.

Thus, as a configuration of the third aspect, there is provided a kit comprising at least one probe or primer for detection and/or quantification of RBM3mRNA or RBM3cDNA.

As described herein, a more refined treatment prediction may be obtained if the levels of both RBM3 and another relevant biomarker. Thus, in an embodiment, the kit of the configuration of the third aspect may further comprise:

a probe or primer for detection and/or quantification of the mRNA or cDNA of one or more of KI-67, C-MYC, MYBL2, FAP, BGN, INHBA, GADD45B, ATP5E, PGK1, GPX1, UBB and VDAC2.

In another embodiment, the kit of the configuration of the third aspect may further comprise:

a probe or primer for detection and/or quantification of the mRNA or cDNA of one or more of MCTP1, LAMA3, CTSC, PYROX D1, EDEM1, IL2RB, ZNF697, SLC6A11, IL2RA, CYFIP2, PIM3, LIF, PLIN3, HSD3B1, ZBED4, PPARA, THNSL2 and CA438802.

A probe or primer according to the configuration of the third aspect may for example be a single or double stranded oligonucleotide that is complementary to a part of the mRNA or cDNA in question. The RBM3 cDNA is represented by SEQ ID NO:3. If the probe is double stranded, it is denatured prior to detection/hybridization to become single stranded, e.g. by means of heating.

The length of the probe(s) or primer(s) may for example be at least 5, such as at least 10, such as at least 15, such as at least 20, such as at least 25, such as at least 30, such as at least 50, such as at least 75, such as at least 100, such as at least 150 consecutive nucleotides.

A primer is normally shorter than a probe.

The kit may comprise further auxiliary products. Examples of such products are described above in connection with the discussion about mRNA analysis. Thus, the kit of the configuration of the third aspect may for example comprise one or more auxiliary products selected from the group consisting of a pre-treatment solution (for preparing the sample), a proteolytic enzyme such as pepsin, a second probe (to be used as a reference), a buffer such as a wash buffer and a fluorescence mounting medium (if fluorescent labels are used). The probes of the configuration of the third aspect may be labeled or conjugated to other chemical moieties. This is also exemplified above in connection with the discussion about mRNA analysis.

Further, the probes of the configuration of the third aspect may for example be arranged on a solid phase, optionally together with probes for one of the other targets. Examples of such other probes are those capable of detecting the mRNA of KI-67, C-MYC, MYBL2, FAP, BGN, INHBA, GADD45B, ATP5E, PGK1, GPX1, UBB and VDAC2. Further examples of such other probes are those capable of detecting the mRNA of MCTP1, LAMA3, CTSC, PYROX D1, EDEM1, IL2RB, ZNF697, SLC6A11, IL2RA, CYFIP2, PIM3, LIF, PLIN3, HSD3B1, ZBED4, PPARA, THNSL2 and CA438802. The analysis of RBM3 may for example be included in a ColoPrint® test. Accordingly, the RBM3 probe may be arranged on a solid phase together with probe(s) for one or more of the other genes of the ColoPrint® test.

Following the findings presented above, the inventors have realized several uses for the RBM3 protein or a fragment thereof or the RBM3 mRNA molecule.

Thus, as a first configuration of a fourth aspect of the present disclosure, there is provided a use of an RBM3 protein or an RBM3 mRNA molecule as a prognostic marker for a mammalian subject having a colorectal cancer. The RBM3 protein or mRNA molecule may for example be provided in a sample.

In a similar manner, there is provided a use of an RBM3 protein or an RBM3 protein molecule as a marker of a relatively good prognosis for a mammalian subject having a colorectal cancer. The RBM3 protein or mRNA molecule may for example be provided in a sample.

In the context of the present disclosure, "prognostic marker" refers to something material which presence indicates a prognosis. The marker may thus be a biomarker, such as a human protein.

As a second configuration of the fourth aspect, there is provided a use of a RBM3 protein, or an antigenically active fragment thereof, for the production, selection or purification of a prognostic agent for a mammalian subject having a colorectal cancer.

In the context of the present disclosure, "prognostic agent" refers to an agent having at least one property being valuable in an establishment of a prognosis, e.g., a prognosis for a mammalian subject having a colorectal cancer. For example, the prognostic agent may be capable of selective interaction with the prognostic marker.

The prognostic agent may be an affinity ligand capable of selective interaction with the RBM3 protein, or an antigenically active fragment thereof. Examples of such affinity ligands are discussed above in connection with the method aspects.

Guided by the teachings of the present disclosure, the person skilled in the art understands how to use RBM3 protein in the production, selection or purification of the prognostic agent. For example, the use may comprise affinity purification on a solid support onto which the RBM3 protein has been immobilized. The solid support may for example be arranged in a column. Further, the use may comprise selection of affinity ligands having specificity for the RBM3 protein using a solid support onto which the polypeptide has been immobilized. Such solid support may be well plates (such as 96 well plates), magnetic beads, agarose beads or sepharose beads. Further, the use may comprise analysis of affinity ligands on a soluble matrix, for example using a dextran matrix, or use in a surface plasmon resonance instrument, such as a Biacore™ instrument, wherein the analysis may for example comprise monitoring the affinity for the immobilized RBM3 protein of a number of potential affinity ligands.

Also, for the production of the prognostic agent, the RBM3 protein or an antigenically active fragment thereof may be used in an immunization of an animal.

Such use may be involved in a method comprising the steps:
i) immunizing an animal using the RBM3 protein or antigenically an active fragment thereof as the antigen;
ii) obtaining serum comprising the prognostic agent from the immunized animal; and, optionally,
iii) isolating the prognostic agent from the serum.
Alternatively the steps following the first step may be:
ii') obtaining cells from the immunized animal, which cells comprise DNA encoding the prognostic agent,
iii') fusing the cells with myeloma cells to obtain at least one clone, and
iv') obtaining the prognostic agent expressed by the clone.

In embodiments of the fourth aspect, the amino acid sequence of the RBM3 protein may comprise or consist of a sequence selected from:
i) SEQ ID NO:1; and
ii) a sequence which is at least 85% identical to SEQ ID NO:1.

In some embodiments, sequence ii) is at least 90% identical, at least 91% identical, at least 92% identical, at least 93% identical, at least 94% identical, at least 95% identical, at least 96% identical, at least 97% identical, at least 98% identical or at least 99% identical to SEQ ID NO:1.

Further, in embodiments of the fourth aspect the amino acid sequence of the RBM3 protein may comprise or consist of a sequence selected from:
i) SEQ ID NO:2; and
ii) a sequence which is at least 85% identical to SEQ ID NO:2.

In some embodiments, sequence ii) is at least 90% identical, at least 91% identical, at least 92% identical, at least 93% identical, at least 94% identical, at least 95% identical, at least 96% identical, at least 97% identical, at least 98% identical or at least 99% identical to SEQ ID NO:2.

Still further, in embodiments of the fourth aspect the amino acid sequence of the RBM3 protein or may comprise a sequence selected from SEQ ID NO:4-19.

In some embodiments, the RBM3 protein or the antigenically active fragment thereof of the fourth aspect consists of no more than 150 amino acids, such as no more than 140 amino acids, such as no more than 135 amino acids, such as no more than 50 amino acids, such as no more than 29 amino acids.

In further embodiments of the fourth aspect, the fragment consists of 20 amino acids or less, such as 15 amino acids or less, and comprises a sequence selected from SEQ ID NO:6-19. As evident from the above discussion about the affinity ligands of the present disclosure, fragments comprising SEQ ID NO:8, 16 or 17 may be considered particularly relevant.

As a fifth aspect of the present disclosure, there is provided an affinity ligand capable of selective interaction with an RBM3 protein.

Different embodiments of such an affinity ligand are discussed above in connection with the method aspects.

The affinity ligand may be used for in vivo diagnosis, such as in vivo imaging.

Thus, as a first configuration of the fifth aspect, there is provided an affinity ligand capable of selective interaction with an RBM3 protein, for in vivo use as a prognostic agent in a mammalian subject having a colorectal cancer.

Accordingly, in an embodiment, the affinity ligand may be for use in an in vivo method for establishing a prognosis for a mammalian subject having a colorectal cancer or determining whether such subject should undergo a certain treatment regimen. In such embodiments the affinity ligand may for example be labeled for enabling imaging, i.e. labeled with a detectable label. Appropriate labels for labeling affinity ligands such as antibodies are well known to the skilled person. The in vivo method for establishing a prognosis may for example reveal RBM3 protein expression in a tumor in vivo, which in turn may form the basis of a treatment decision. Various in vivo methods, labels and detection techniques that may be used in the context of this embodiment are further discussed above.

In a similar configuration of the fifth aspect, there is provided an affinity ligand, capable of selective interaction with an RBM3 protein, for in vivo evaluation an amount of RBM3 protein in a subject having a colorectal cancer. For example, the level of RBM3 expression in the colorectal tumor may be evaluated.

As a sixth aspect of the present disclosure, there is provided a use of an affinity ligand according to the fifth aspect as prognostic agent for a mammalian subject having a colorectal cancer. Consequently, the affinity ligand may be used for establishing a prognosis for a colorectal cancer subject. Such use may for example be performed in vitro, e.g., involving the determination of the amount of RBM3 in at least part of a sample earlier obtained from the subject.

EXAMPLES

Generation of Mono-Specific Antibodies Against RBM3 and Use Thereof to Detect RBM3 in Normal and Cancerous Samples Polyclonal Antibodies 1. Generation of Antigen
a) Materials and Methods A suitable fragment of the target protein encoded by the EnsEMBL Gene ID ENSG00000102317 was selected using bioinformatic tools with the human genome sequence as template (Lindskog M et al (2005) Biotechniques 38:723-727, EnsEMBL, www.ensembl.org). The fragment was used as template for the production of a 134 amino acid long fragment corresponding to amino acids 18-151 (SEQ ID NO:1) of the RBM3 protein (SEQ ID NO:2; EnsEMBL entry no. ENSP00000365946).

A fragment of the RBM3 gene transcript containing nucleotides 281-682, of EnsEMBL entry number ENST00000376755 (SEQ ID NO:3), was isolated by a Superscript™ One-Step RT-PCR amplification kit with Platinum® Taq (Invitrogen) and a human total RNA pool panel as template (Human Total RNA, BD Biosciences Clontech). Flanking restriction sites NotI and AscI were introduced into the fragment through the PCR amplification primers, to allow in-frame cloning into the expression vector (forward primer: GACGAGCAGGCACTGGAAG (SEQ ID NO:27), reverse primer: GTAATTTCCTCCTGAGTAGC (SEQ ID NO:28). Then, the downstream primer was biotinylated to allow solid-phase cloning as previously described, and the resulting biotinylated PCR product was immobilized onto Dynabeads M280 Streptavidin (Dynal Biotech) (Larsson M et al (2000) J. Biotechnol. 80:143-157). The fragment was released from the solid support by NotI-AscI digestion (New England Biolabs), ligated into the pAff8c vector (Larsson M et al, supra) in frame with a dual affinity tag consisting of a hexa-histidyl tag for immobilized metal ion chromatography (IMAC) purification and an immunopotentiating albumin binding protein (ABP) from streptococcal protein G (Sjölander A et al (1997) J. Immunol. Methods 201:115-123; Ståhl S et al (1999) Encyclopedia of Bioprocess Technology: Fermentation, Biocatalysis and Bioseparation (Fleckinger M C and Drew S W, eds) John Wiley and Sons Inc., New York, pp 49-63), and transformed into E. coli BL21(DE3) cells (Novagen). The sequences of the clones were verified by dye-terminator cycle sequencing of plasmid DNA amplified using TempliPhi DNA sequencing amplification kit (GE Healthcare, Uppsala, Sweden) according to the manufacturer's recommendations.

BL21(DE3) cells harboring the expression vector were inoculated in 100 ml 30 g/l tryptic soy broth (Merck KGaA) supplemented with 5 g/l yeast extract (Merck KGaA) and 50 mg/l kanamycin (Sigma-Aldrich) by addition of 1 ml of an overnight culture in the same culture medium. The cell culture was incubated in a 1 liter shake flask at 37° C. and 150 rpm until the optical density at 600 nm reached 0.5-1.5. Protein expression was then induced by addition of isopropyl-β-D-thiogalactopyranoside (Apollo Scientific) to a final concentration of 1 mM, and the incubation was continued overnight at 25° C. and 150 rpm. The cells were harvested by centrifugation at 2400 g, and the pellet was re-suspended in 5 ml lysis buffer (7 M guanidine hydrochloride, 47 mM $Na_2HPO_4$, 2.65 mM $NaH_2PO_4$, 10 mM Tris-HCl, 100 mM NaCl, 20 mM β-mercaptoethanol; pH=8.0) and incubated for 2 hours at 37° C. and 150 rpm. After centrifugation at 35300 g, the supernatant containing the denatured and solubilized protein was collected.

The $His_6$-tagged fusion protein was purified by immobilized metal ion affinity chromatography (IMAC) on columns with 1 ml Talon® metal ($Co^{2+}$) affinity resin (BD Biosciences Clontech) using an automated protein purification procedure (Steen J et al (2006) Protein Expr. Purif. 46:173-178) on an ASPEC XL4™ (Gilson). The resin was equilibrated with 20 ml denaturing washing buffer (6 M guanidine hydrochloride, 46.6 mM $Na_2HPO_4$, 3.4 mM $NaH_2PO_4$, 300 mM NaCl, pH 8.0-8.2). Clarified cell lysates were then added to the column. Thereafter, the resin was washed with a minimum of 31.5 ml washing buffer prior to elution in 2.5 ml elution buffer (6 M urea, 50 mM $NaH_2PO_4$, 100 mM NaCl, 30 mM acetic acid, 70 mM Na-acetate, pH 5.0). The eluted material was fractioned in three pools of 500, 700 and 1300 μl. The 700 μl fraction, containing the antigen, and the pooled 500 and 1300 μl fractions were stored for further use.

The antigen fraction was diluted to a final concentration of 1 M urea with phosphate buffered saline (PBS; 1.9 mM $NaH_2PO_4$, 8.1 mM $Na_2HPO_4$, 154 mM NaCl) followed by a concentration step to increase the protein concentration using Vivapore 10/20 ml concentrator with molecular weight cut off at 7500 Da (Vivascience AG). The protein concentration was determined using a bicinchoninic acid (BCA) micro assay protocol (Pierce) with a bovine serum albumin standard according to the manufacturer's recommendations. The protein quality was analyzed on a Bioanalyzer instrument using the Protein 50 or 200 assay (Agilent Technologies).

b) Results

A gene fragment corresponding to nucleotides 281-682 of the full-lengths transcript of RBM3 (SEQ ID NO:3) was successfully isolated by RT-PCR from a human RNA pool using primers specific. The fragment codes for amino acids 18 to 151 of the target protein RBM3 (SEQ ID NO:2). The 134 amino acid fragment (SEQ ID NO:1) of the target protein (SEQ ID NO:2) was designed to lack transmembrane regions to ensure efficient expression in E. coli, and to lack any signal peptide, since those are cleaved off in the mature protein. In addition, the protein fragment was designed to consist of a unique sequence with low homology with other human proteins, to minimize cross reactivity of generated affinity reagents, and to be of a suitable size to allow the formation of conformational epitopes and still allow efficient cloning and expression in bacterial systems.

A clone encoding the correct amino acid sequence was identified, and, upon expression in E. coli, a single protein of the correct size was produced and subsequently purified using immobilized metal ion chromatography. After dilution of the eluted sample to a final concentration of 1 M urea and concentration of the sample to 1 ml, the concentration of the protein fragment was determined to be 10.4 mg/ml and was 96.0% pure according to purity analysis.

2. Generation of Antibodies
a) Materials and Methods

The purified RBM3 fragment as obtained above was used as antigen to immunize a rabbit in accordance with the national guidelines (Swedish permit no. A 84-02). The rabbit was immunized intramuscularly with 200 μg of antigen in Freund's complete adjuvant as the primary immunization, and boosted three times in four week intervals with 100 μg antigen in Freund's incomplete adjuvant.

Antiserum from the immunized animal was purified by a three-step immunoaffinity based protocol (Agaton C et al (2004) J. Chromatogr. A 1043:33-40; Nilsson P et al (2005) Proteomics 5:4327-4337). In the first step, 7 ml of total antiserum was buffered with 10×PBS to a final concentration of 1×PBS (1.9 mM $NaH_2PO_4$, 8.1 mM $Na_2HPO_4$, 154 mM NaCl), filtered using a 0.45 µm pore-size filter (Acrodisc®, Life Science) and applied to an affinity column containing 5 ml N-hydroxysuccinimide-activated Sepharose™ 4 Fast Flow (GE Healthcare) coupled to the dual affinity tag protein $His_6$-ABP (a hexahistidyl tag and an albumin binding protein tag) expressed from the pAff8c vector and purified in the same way as described above for the antigen protein fragment. In the second step, the flow-through, depleted of antibodies against the dual affinity tag $His_6$-ABP, was loaded at a flow rate of 0.5 ml/min on a 1 ml Hi-Trap NHS-activated HP column (GE Healthcare) coupled with the RBM3 protein fragment used as antigen for immunization (SEQ ID NO:1). The $His_6$-ABP protein and the protein fragment antigen were coupled to the NHS activated matrix as recommended by the manufacturer. Unbound material was washed away with 1×PBST (1×PBS, 0.1% Tween20, pH 7.25), and captured antibodies were eluted using a low pH glycine buffer (0.2 M glycine, 1 mM EGTA, pH 2.5). The eluted antibody fraction was collected automatically, and loaded onto two 5 ml HiTrap™ desalting columns (GE Healthcare) connected in series for efficient buffer exchange in the third step. The second and third purification steps were run on the ÄKTAxpress™ platform (GE Healthcare). The antigen selective (mono-specific) antibodies (msAbs) were eluted with PBS buffer, supplemented with glycerol and $NaN_3$ to final concentrations of 40% and 0.02%, respectively, for long term storage at −20° C. (Nilsson P et al (2005) Proteomics 5:4327-4337).

The specificity and selectivity of the affinity purified antibody fraction were analyzed by binding analysis against the antigen itself and against 94 other human protein fragments in a protein array set-up (Nilsson P et al (2005) Proteomics 5:4327-4337). The protein fragments were diluted to 40 µg/ml in 0.1 M urea and 1×PBS (pH 7.4) and 50 µl of each were transferred to the wells of a 96-well spotting plate. The protein fragments were spotted in duplicate and immobilized onto epoxy slides (SuperEpoxy, TeleChem) using a pin-and-ring arrayer (Affymetrix 427). The slide was washed in 1×PBS (5 min) and the surface was then blocked (SuperBlock®, Pierce) for 30 minutes. An adhesive 16-well silicone mask (Schleicher & Schuell) was applied to the glass before the mono-specific antibodies were added (diluted 1:2000 in 1×PBST to appr. 50 ng/ml) and incubated on a shaker for 60 min. Affinity tag-specific IgY antibodies were co-incubated with the mono-specific antibodies in order to quantify the amount of protein in each spot. The slide was washed with 1×PBST and 1×PBS twice for 10 min each. Secondary antibodies (goat anti-rabbit antibody conjugated with Alexa 647 and goat anti-chicken antibody conjugated with Alexa 555, Molecular Probes) were diluted 1:60000 to 30 ng/ml in 1×PBST and incubated for 60 min. After the same washing procedure, as for the first incubation, the slide was spun dry and scanned (G2565BA array scanner, Agilent), thereafter images were quantified using image analysis software (GenePix 5.1, Axon Instruments).

In addition, the specificity and selectivity of the affinity-purified antibody were analyzed by Western blot. Western blot was performed by separation of total protein extracts from selected human cell lines on pre-cast 10-20% SDS-PAGE gradient gels (Bio-Rad Laboratories) under reducing conditions, followed by electro-transfer to PVDF membranes (Bio-Rad Laboratories) according to the manufacturer's recommendations. The membranes were blocked (5% dry milk, 1×TBST; 0.1 M Tris-HCl, 0.5 M NaCl, 0.1% Tween20) for 1 h at room temperature, incubated with the primary affinity purified antibody (diluted 1:500 in blocking buffer) and washed in TBST. The secondary HRP-conjugated antibody (swine anti-rabbit immunoglobulin/HRP, DakoCytomation) was diluted 1:3000 in blocking buffer and chemiluminescence detection was carried out using a Chemidoc™ CCD camera (Bio-Rad Laboratories) and SuperSignal® West Dura Extended Duration substrate (Pierce), according to the manufacturer's protocol.

b) Results

The quality of polyclonal antibody preparations has proven to be dependent on the degree of stringency in the antibody purifications, and it has previously been shown that depletion of antibodies directed against epitopes not originated from the target protein is necessary to avoid cross-reactivity to other proteins and background binding (Agaton C et al (2004) J. Chromatogr. A 1043:33-40). Thus, a protein microarray analysis was performed to ensure that mono-specific polyclonal antibodies of high specificity had been generated by depletion of antibodies directed against the $His_6$-tag as well as of antibodies against the ABP-tag.

To quantify the amount of protein in each spot of the protein array, a two-color dye labeling system was used, with a combination of primary and secondary antibodies. Tag-specific IgY antibodies generated in hen were detected with a secondary goat anti-hen antibody labeled with Alexa 555 fluorescent dye. The specific binding of the rabbit msAb to its antigen on the array was detected with a fluorescently Alexa 647 labeled goat anti-rabbit antibody. Each protein fragment was spotted in duplicates. The protein array analysis shows that the affinity purified mono-specific antibody against RBM3 is highly selective to the correct protein fragment and has a very low background to all other protein fragments analyzed on the array.

The result of the Western blot analysis shows that the antibody specifically detects a single band of approximately 16 kDa in two breast tumor cell lines, T47D and MCF-7. The theoretical molecular weight of RBM3 is 16 kDa (as calculated from the RBM3 amino acid sequence SEQ ID NO:2), corresponding well to the result obtained.

Monoclonal Antibodies

3. Generation of Monoclonal Antibodies.

a) Materials and Methods

The purified fragment (SEQ ID NO:1) obtained in Section 1 was used as antigen for production of monoclonal antibodies. Antigen was sent to AbSea Biotechnology Ltd (Beijing, China) and briefly, the antigen was injected subcutaneously into BALB/c mice (4-6 weeks old, female) at three week intervals. The antigen was mixed with complete Freund's adjuvant for the first injection and incomplete Freund's adjuvant for the following injections. Three days before fusion, the mouse was last challenged with antigen intravenously. Hybridomas were generated by fusion of mouse splenocytes with the Sp2/0 myeloma cell line. By screening several cell lines using ELISA, cells that secreted antibodies specific for the antigen (SEQ ID NO:1) were identified and delivered to Atlas Antibodies AB for further characterization. Cell lines that showed positive results in ELISA, Western blot (WB) and immunohistochemistry (IHC) were selected for subcloning, performed by AbSea Biotechnology Ltd.

In addition, the immunohistochemical staining patterns of the monoclonal antibodies were compared to that of the polyclonal anti-RBM3 antibody generated in Section 2. This polyclonal antibody is sometimes referred to herein as "anti-RBM3".

b) Results

Cell-lines were screened by ELISA (at AbSea) to identify lines that produce monoclonal antibodies (mAbs) that recognize the antigen (SEQ ID NO:1), but not the affinity tag His-ABP. Eight cell-lines showed specific binding to the antigen SEQ ID NO:1 in ELISA and were selected for further testing. For each of the selected eight clones 150-300 µl supernatant was collected, azide was added, and the supernatants were delivered to Atlas Antibodies AB on wet ice. The supernatants were stored at +4° C. upon arrival according to the instructions from AbSea. Further testing of the cell lines resulted in the identification of three interesting cell lines, clones 1B5, 6F11 and 7G3 that gave positive results in both Western blot and IHC analysis. These clones were selected for subcloning and expansion, performed by AbSea Biotechnology Ltd.

Tissue Micro Array (TMA) Analysis

4. Colon Carcinoma TMA (Sigmoid Cohort)

a) Material and Methods

Archival formalin-fixed paraffin-embedded tissue from 305 patients (148 women and 157 men) surgically treated for sigmoid cancer between 1993 and 2003 was collected from the Department of Pathology, Malmö University Hospital, Sweden. The median age of patients was 74 (39-97) years. 47 tumors were Dukes' stage A, 129 Dukes' stage B, 84 Dukes' stage C and 45 with Dukes' stage D. Information regarding the date of death was obtained from the regional cause-of-death registries for all patients. Ethical permission was obtained from the Local Ethics Committee.

All 305 cases were histopathologically re-evaluated on slides stained with hematoxylin and eosin. TMA:s were then constructed by sampling 2×1.0 mm cores per case from areas representative of sigmoid colon carcinoma.

Automated immunohistochemistry was performed as previously described (Kampf C et al (2004) Clin. Proteomics 1:285-300). In brief, the glass slides were incubated for 45 min in 60° C., de-paraffinized in xylene (2×15 min) and hydrated in graded alcohols. For antigen retrieval, slides were immersed in TRS (Target Retrieval Solution, pH 6.0, Dako, Copenhagen, Denmark) and boiled for 4 min at 125° C. in a Decloaking Chamber® (Biocare Medical). Slides were placed in the Autostainer® (Dako) and endogenous peroxidase was initially blocked with $H_2O_2$ (Dako). The slides were incubated for 30 min at room temperature with the primary RBM3 antibody obtained as in Examples, Section 2, followed by incubation for 30 min at room temperature with goat anti-rabbit peroxidase conjugated Envision®. Between all steps, slides were rinsed in wash buffer (Dako). Finally, diaminobenzidine (Dako) was used as chromogen and Harris hematoxylin (Sigma-Aldrich) was used for counterstaining. The slides were mounted with Pertex® (Histolab).

All samples of immunohistochemically stained tissue were manually evaluated under the microscope and annotated by a certified pathologist. Annotation of each sample was performed using a simplified scheme for classification of IHC outcome. Each tissue sample was examined for representativity and immunoreactivity.

Basic annotation parameters included an evaluation of i) subcellular localization (nuclear and/or cytoplasmic/membranous), ii) staining intensity (SI) and iii) fraction of stained cells (FSC). Staining intensity was subjectively evaluated in accordance to standards used in clinical histo-pathological diagnostics and outcome was classified as: absent=no immunoreactivity, weak—moderate=faint to medium immunoreactivity, or strong=distinct and strong immunoreactivity. Also fraction of stained cells was subjectively evaluated in accordance to standards used in clinical histo-pathological diagnostics and outcome was classified as: <2%, 2-25%, >25-75% or >75% immunoreactive cells of the relevant cell population. The skilled artisan will recognize that this annotation procedure is similar to a calculation of an Allred score, see e.g. Allred et al (1998) Mod Pathol 11(2), 155. Thus, tissue annotation was essentially done as described in section 3 above, with the exception that staining intensity and fraction of stained cells were not combined to yield a "staining score".

For statistical analyses, the nuclear fraction (NF), nuclear intensity (NI) level and cytoplasmic intensity (CI) level was evaluated. Based on the survival trends for individual strata, dichotomized variables were constructed for further statistical analyses. For analysis using the RBM3 antibody, a high nuclear fraction was defined either as 2-100% (NF>0) or >75% (NF=3) fraction of cells stained and a low nuclear fraction was defined as <2% (NF=0) or 0-75% (NF<3) of fraction of cells stained. Further, a high protein expression level was defined either as a weak—moderate and strong nuclear intensity (NI>0) or a strong nuclear intensity (NI=2) and a low protein expression level was defined either as an absent nuclear intensity (NI=0) or absent—weak and moderate nuclear intensity (NI<2). Also, a high protein expression level was defined either as a weak—moderate and strong cytoplasmic intensity (CI>0) or a strong cytoplasmic intensity (CI=2) and a low protein expression level was defined either as an absent cytoplasmic intensity (CI=0) or absent—weak and moderate cytoplasmic intensity (CI<2). The above classification of samples was used for overall survival (OS) and disease free survival (DFS) analysis according to the Kaplan-Meier method, and the log-rank test was used to compare survival in different strata. All statistical tests were two-sided, and p-values of <0.05% were considered significant. All calculations were made with the statistical package SPSS 17.0 (SPSS Inc. Illinois, USA).

b) Results

Figure 1B:
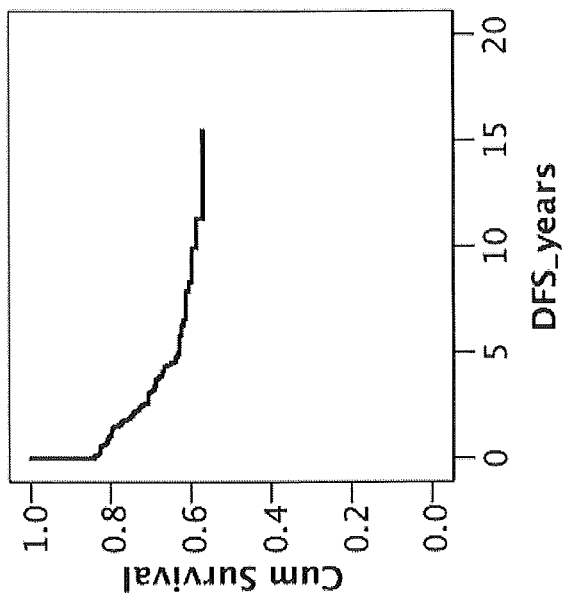

Initial analysis of the sigmoid cohort revealed that OS for all patients was approximately 55% and DFS was approximately 64%, as seen in FIGS. 1A and 1B respectively.

Immunohistochemical analysis of RBM3 expression could be performed on 274 tumor samples. The remaining cores either did not contain tumor cells or had been lost during histoprocessing. RBM3 expression analysis resulted in a nuclear and cytoplasmic staining but 145 subjects (59%) lacked expression (NF<2%).

Figure 2:
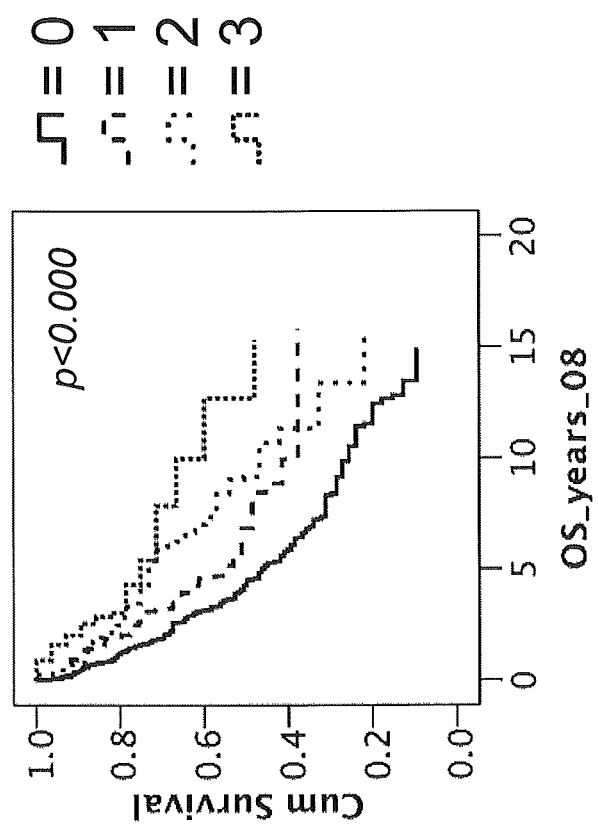
FIG. 2 shows the impact of RBM3 level on OS if splitting all 274 subjects into groups based on nuclear fraction (NF) staining. Briefly, all subjects were split into four groups based on NF status, i.e. <2%, 2-25%, >25-75% or >75%.
Figure 3B:
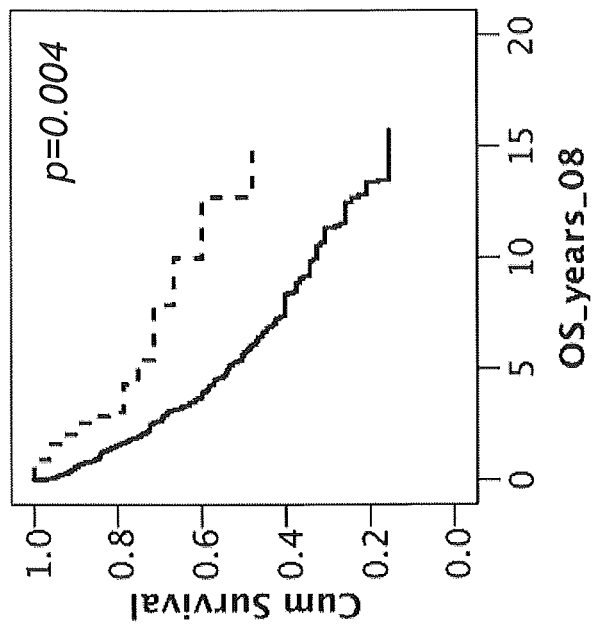
FIGS. 3A-3B show the results of OS analysis including all 274 subjects. RBM3 expression was dichotomized as high and low in two ways.
Figure 3A:
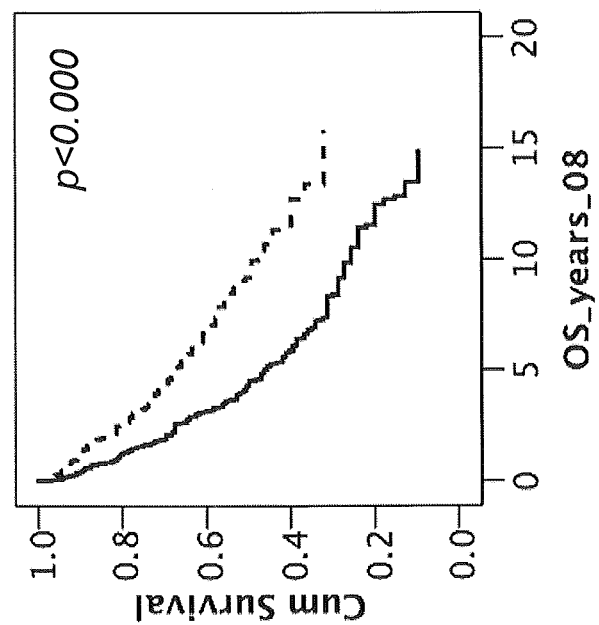
Figure 4:
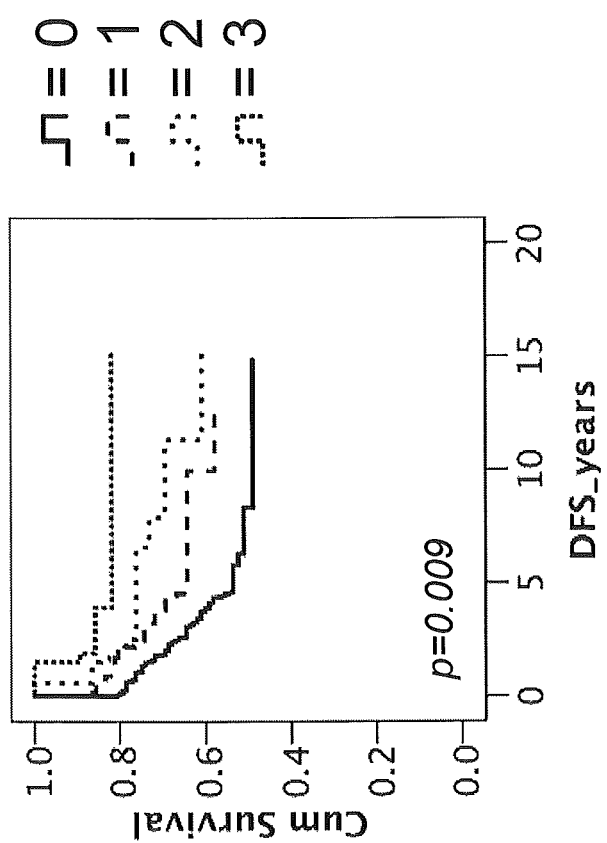
FIG. 4 shows the impact on DFS if splitting all 274 subjects into groups based on nuclear fraction (NF) staining. Briefly, all subjects were split into four groups based on NF status, i.e. <2%, 2-25%, >25-75% or >75%.
Figure 5A:
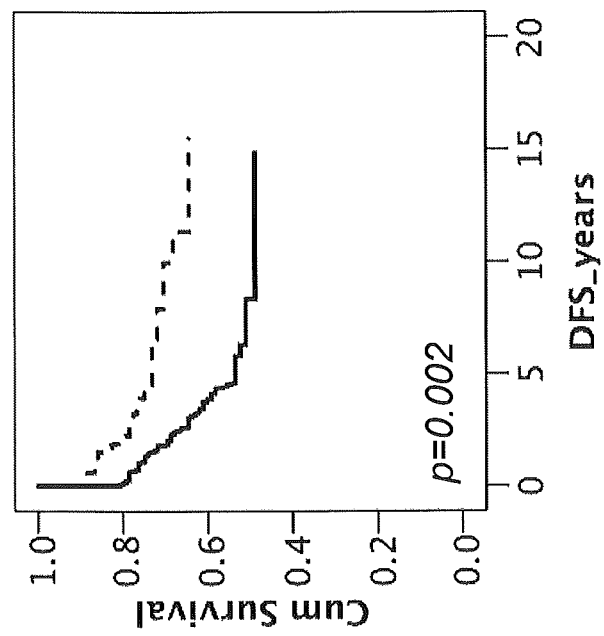
FIGS. 5A-5B show the results of a DFS analysis for all 274 subjects based on nuclear fraction (NF) levels of RBM3. RBM3 expression was dichotomized into high and low categories in two ways.
Figure 5B:
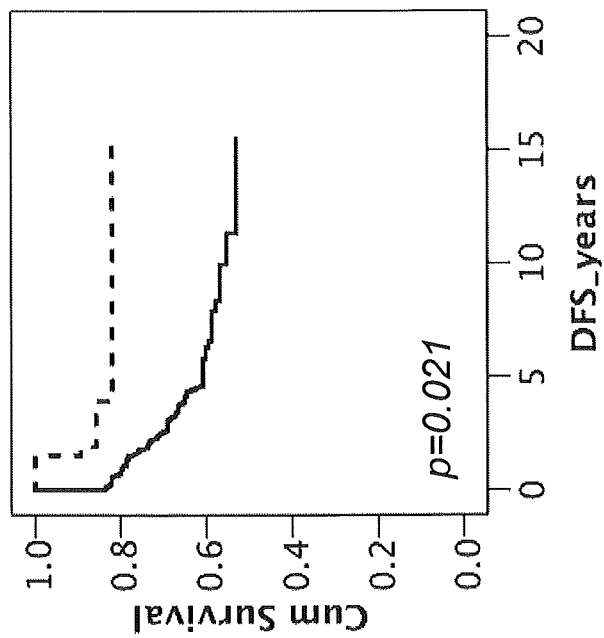
Figure 6B:
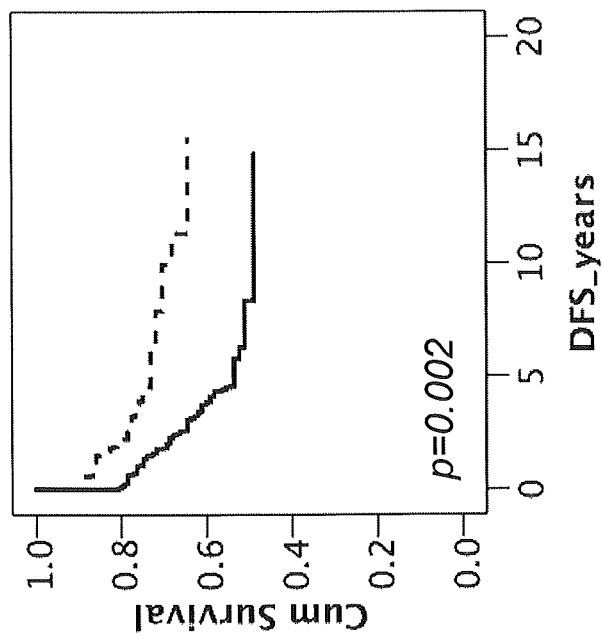
FIGS. 6A-6B show the results of survival analysis for all 274 subjects based on nuclear intensity (NI) levels of RBM3. RBM3 expression was dichotomized into high and low categories in two ways. A solid line represents a low RBM3 level (NI=0), and a dotted line represents a high RBM3 level (NI>0).
Figure 6A:
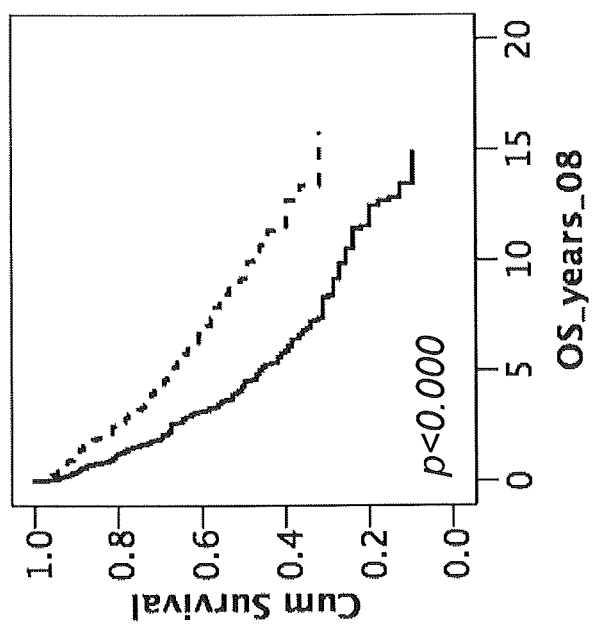
Figure 7B:
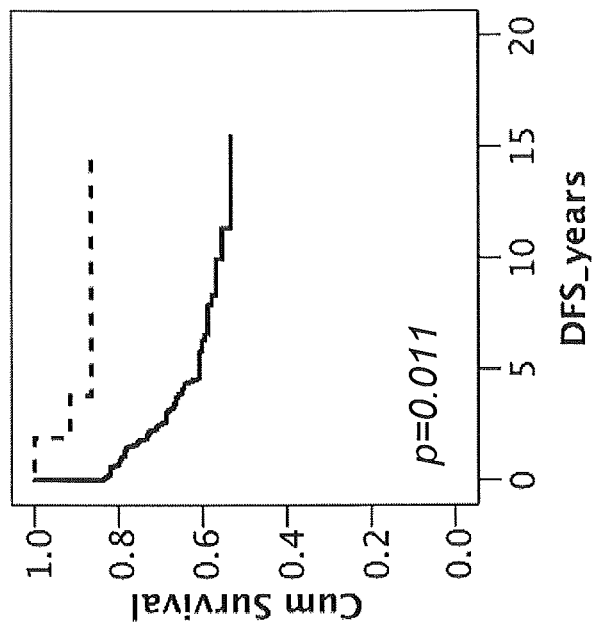
FIGS. 7A-7B show the results of DFS analysis for all 274 subjects based on cytoplasmic intensity (CI) levels of RBM3. RBM3 expression was dichotomized into high and low categories in two ways.
Figure 7A:
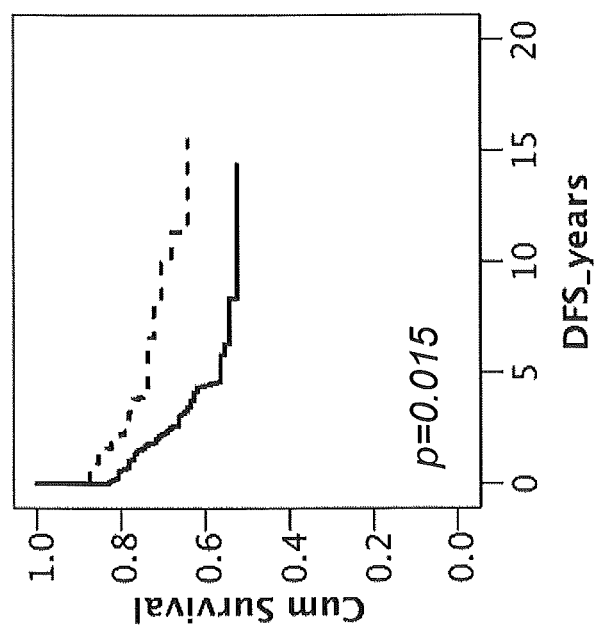
Figure 8B:
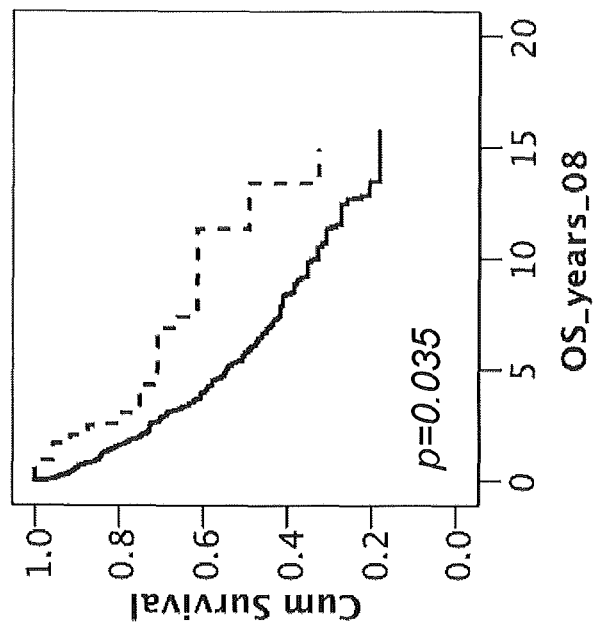
FIGS. 8A-8B show the results of OS analysis for all 274 subjects based on cytoplasmic intensity (CI) levels of RBM3. RBM3 expression was dichotomized into high and low categories in two ways.
Figure 8A:
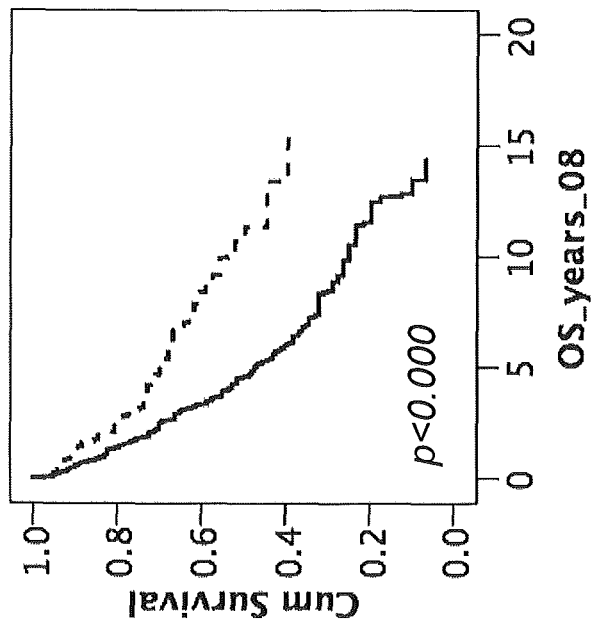

Survival analysis of the entire cohort revealed that expression of RBM3 in tumor tissues was significantly correlated with overall and disease free survival (OS and DFS) (FIGS. 2-8B). In FIGS. 2 and 4 the subjects were divided into four different categories based on the NF. For patients with a fraction value of NF>75%, five-year OS was approximately 75%, whereas patients lacking RMB3 expression had an OS of about 45% (FIG. 2). In FIG. 4, analysis of DFS reveled that patients with a high NF value had a five-year DFS of approximately 80%, whereas patients lacking RMB3 protein expression had a DFS of about 55%. Both FIGS. 2 and 4 clearly shows that the higher the fraction of cells staining positive for RBM3 the longer survival may be expected for the patient. Thus, a high NF indicates a relatively good prognosis whereas a low NF indicates a relatively poor prognosis. Analysis of OS and DFS with dichotomized variables further supports these findings (FIGS. 3A, 3B, 5A and 5B). Further, these figures show that OS and DFS analyses at both a relatively low and a relatively high cut-off yield significant results. Similar results were obtained when analyzing OS and DFS based on nuclear intensity and cytoplasmic intensity (FIGS. 6A-8B). That is, the stronger the intensity, the longer the survival.

Figure 12B:
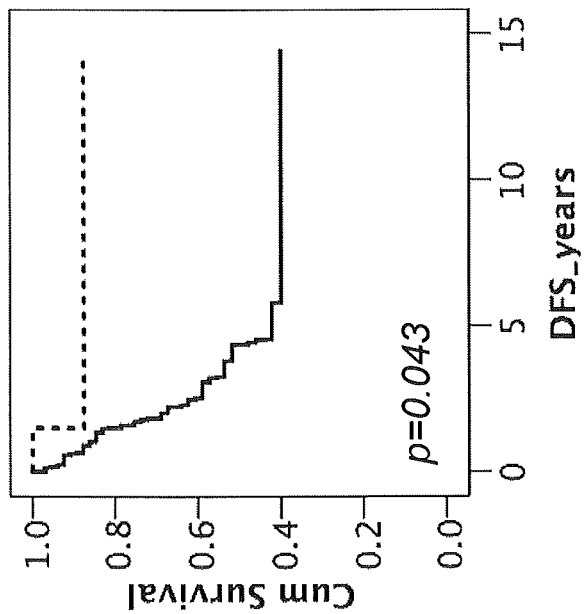
FIGS. 12A-12B show the results of DFS analysis for the 76 subjects diagnosed with Dukes stage C based on nuclear fraction (NF) levels of RBM3. RBM3 expression was dichotomized as high and low in two ways.
Figure 12A:
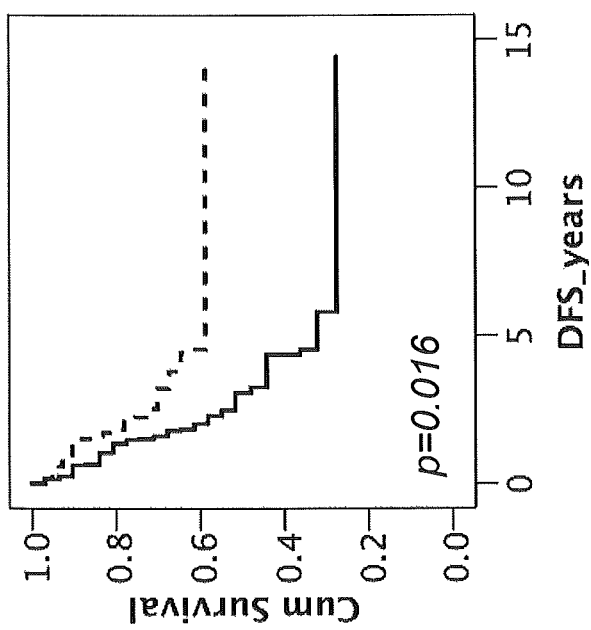
Figure 13B:
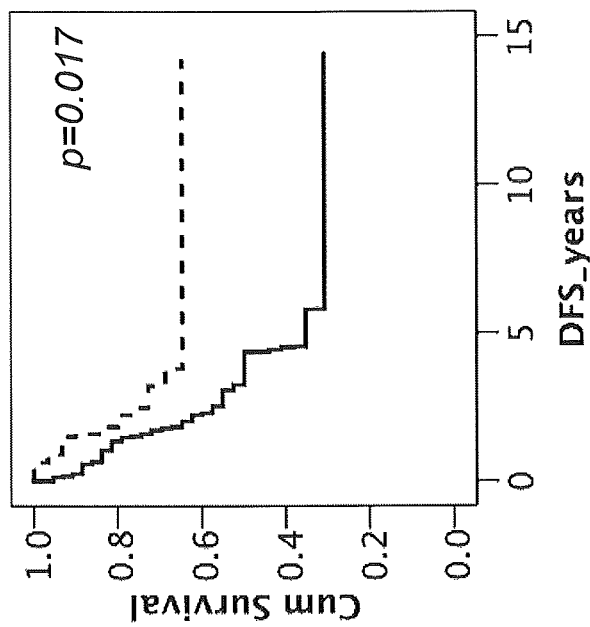
FIGS. 13A-13B show the results of survival analysis for the 76 subjects diagnosed with Dukes stage C based on cytoplasmic intensity (CI) levels of RBM3. Tissue cores were dichotomized by high and low RBM3 expression. A solid line represents a low RBM3 level (CI=0), and a dotted line represents a high RBM3 level (CI>0).
Figure 13A:
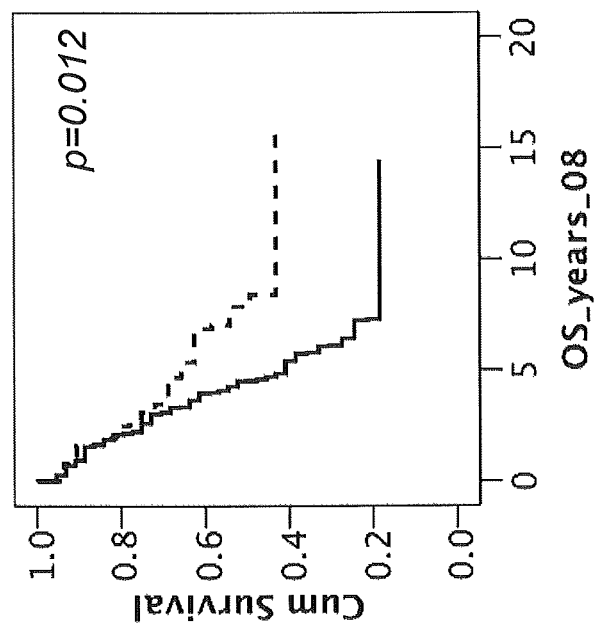

When studying subjects diagnosed with Dukes' stage A and B or stage B only, the significant difference in OS is still observed (FIGS. 9A-9B and 10A-10B). This finding shows that RBM3 has a value as a prognostic predictor already at early stages of the disease. Further, when studying subjects diagnosed with Dukes' stage C, the difference in expected survival may be considered even more pronounced. Regarding the patients with a high NF (i.e. >75%), about 88% of the patients were still alive after five years whereas only approximately 32% of the patients with low NF (i.e. NF<2%), were alive after the same time period, see FIG. 11. Analysis with dichotomized variables further supports these findings (FIGS. 12A-12B). Similar results were obtained when analyzing OS and DFS based on intensity as seen in FIGS. 13A-13B were OS and DFS analysis are shown for cytoplasmic intensity. The stronger the cytoplasmic intensity, the longer survival may be expected.

In conclusion, for a patient diagnosed with colorectal cancer, e.g. sigmoid carcinoma, the use of an anti-RBM3 protein antibody may be of significant value for establishing a prognosis for a patient, e.g. the probability of survival, such as five-year survival, as can be seen from FIGS. 1A to 13B.

Epitope Mapping

5. Epitope Mapping Using Bacterial Display I

RBM3 DNA corresponding to SEQ ID NO:1 (i.e. aa 18-151 of ENSP00000365946 or by 261-682 ENST00000376755) was amplified by PCR using vector pAff8c as template. The amplified DNA was fragmentized to various lengths (approximately 50-150 bp) by sonication, followed by ligation into the staphylococcal display vector (pSCEM2) and transformed into S. carnosus yielding around 100000 transformants. In-frame DNA fragments were displayed as peptides on the staphylococcal surface. After incubation with antibody (selective for SEQ ID NO:1, obtained as in Section 2 above) and fluorescently labeled secondary reagents, positive and negative cells were separately sorted using flow cytometry in order to isolate epitope and non-epitope presenting cells. Isolated cells were sequenced by pyrosequencing and sequences finally aligned to the RBM3 antigen for identification of epitopes.

A dual-labeling strategy with real-time monitoring of the surface expression level was used (Löfblom, J et al (2005) FEMS MicrobiolLett 248, 189-198). It allowed for normalization of the binding signal with the expression level, provided low cell-to-cell variations and made discrimination of different epitope populations possible. Further, it also allowed for a parallel assay to determine non-binding peptides displayed on the surface.

Two epitopes regions, SEQ ID NO:4 (RGFGFITFTNPEHASVAMRAMNGESLDGR) and SEQ ID NO:5 (RSYSRGGGDQGYGSGRYYDSRPGG), within SEQ ID NO:1 were identified.

6. Epitope mapping using Luminex a) Synthetic Peptide Preparation

A PEPscreen library consisting of 25 biotinylated peptides corresponding to the PrEST HPRR232631 (SEQ ID NO:1) on RBM3 was synthesized by Sigma-Genosys (Sigma-Aldrich). The peptides were 15 amino acids long with a 10 amino acid overlap, together covering the entire PrEST-sequence. The peptides were resolved in 80% DMSO to a final concentration of 10 mg/ml.

b) Bead Coupling

Neutravidin (Pierce, Rockford, Ill.) was immobilized on carboxylated beads (COOH Microspheres, Luminex-Corp., Austin, Tex.) in accordance to the manufacturer's protocol. Coupling of $10^6$ beads was performed using a filter membrane bottomed microtiter plate (MultiScreen-HTS, Millipore, Billerica, Mass.) as previously described (Larsson et at (2009) J Immunol Methods 15; 34(1-2):20-32, Schwenk et al (2007) Mol Cell Proteomics 6(1) 125:32). 25 distinct groups of beads with different color code IDs were activated using 1-Ethyl-3-(3-dimethylamino-propyl) carbodiimide and N-Hydroxysuccinimide. Neutravidin (100 μg/ml in MES) was added to the beads and incubated for 120 min on a shaker. The beads were finally washed, re-suspended, and transferred to microcentrifuge tubes for storage at 4° C. in a protein containing buffer (BRE, Blocking Reagent for ELISA, Roche, Basel, Switzerland) supplemented with NaN3. All coupled bead populations were treated with sonication in an ultrasonic cleaner (Branson Ultrasonic Corporation, Danbury, Conn.) for 5 min. The biotinylated peptides were diluted in BRE to a concentration of 20 μM, and 100 μl of each peptide was used in the coupling reaction, which was conducted for 60 min with shaking at RT. Finally, the beads were washed with 3×100 μl BRE buffer and stored at 4° C. until further use.

c) Determination of Binding Specificity

A bead mixture containing all 25 bead IDs was prepared and 45 μl of each antibody diluted to 50 ng/ml in PBS was mixed with 5 μl of the bead mix and incubated for 60 min at RT. A filter bottomed microtiter plate (Millipore) was utilized for washing and following each incubation all wells were washed with 3×100 μl PBST. 50 μl of R-Phycoerythrine labeled anti-rabbit IgG antibody (0.5 μg/ml, Jackson ImmunoResearch) or 50 μl of Alexa Fluor 555 goat anti-mouse IgG were added (0.4 ug/ml) for a final incubation of 60 min at RT.

Measurements were performed using the Luminex LX200 instrumentation with LuminexxPONENT software. For each experiment 50 events per bead ID were counted and the median fluorescence intensity (MFI) was used as a measurement of antibody binding to individual bead populations.

d) Results

The specificities of the monospecific polyclonal antibody (anti-RBM3, HPA003624) and the monoclonal antibody 6F11 were tested in an assay using beads coupled with synthetic biotinylated peptides. Anti-RBM3 showed strong binding to 8 of the peptides, namely 6, 7, 8, 14, 15, 16, 24 and 25, corresponding to three distinct regions on the PrEST sequence, consensus sequences SEQ ID NO: 6, 7, 8 and 9. In particular peptide 24 and 25, corresponding to SEQ ID NO:9 generated a strong signal. The monoclonal antibody 6F11 reacted with two peptides: 15 and 16, corresponding to one distinct region on the PrEST sequence, consensus sequence SEQ ID NO: 8. As both anti-RBM3 and 6F11 bound to peptides 15 and 16, this indicates that these antibodies share one or more epitope(s) within this region. It is notable that SEQ ID NO:6 is within SEQ ID NO:4 and that SEQ ID NO:8 to some extent overlaps with SEQ ID NO:5.

7. Epitope Mapping Using Bacterial Display II

RBM3 DNA corresponding to SEQ ID NO:1 (i.e. aa 18-151 of ENSP00000365946 or by 261-682 ENST00000376755) was amplified by PCR using vector pAff8c as template. The amplified DNA was fragmentized to various lengths (approximately 50-150 bp) by sonication, followed by ligation into the staphylococcal display vector (pSCEM2) and transformed into S. Carnosus yielding around 100000 transformants. In-frame DNA fragments were displayed as peptides on the staphylococcal surface. After incubation with antibody (anti-RBM3 obtained in Section 2 and monoclonal antibodies obtained in Section 3) and fluorescently labeled secondary reagents, positive and negative cells were separately sorted using flow cytometry in order to isolate epitope and non-epitope presenting cells. Plasmid DNA from isolated cells was sequenced by Sanger sequencing and sequences were aligned to the RBM3 antigen for identification of epitopes.

A dual-labeling strategy with real-time monitoring of the surface expression level was used (Löfblom J et al (2005) FEMS MicrobiolLett 248, 189-198). It allowed for normalization of the binding signal with the expression level, provided low cell-to-cell variations and made discrimination of different epitope populations possible. Further, it also allowed for a parallel assay to determine non-binding peptides displayed on the surface.

For the polyclonal antibody, the regions SEQ ID NO:10-15 within SEQ ID NO:1, were identified. In particular, the regions SEQ ID NO:11 and SEQ ID NO:12 were of interest, since they were found within the earlier identified region SEQ ID NO:4. Further, the regions SEQ ID NO:13 and 14 were particularly interesting, since they to a large extent overlapped with previously identified SEQ ID NO:6 and 7, respectively.

For the monoclonal antibody 6F11, the region SEQ ID NO:16 within SEQ ID NO:1 was identified, and this region (SEQ ID NO:16) is within the earlier identified region SEQ ID NO:5. The epitope region of 6F11 identified here in Section 7 has a one-amino acid overlap with the 6F11 epitope region identified in Section 6. The results of Sections 6 and 7 are, however, not in contrast; one of the peptides found to bind 6F11 in Section 6 (peptide 16) comprises SEQ ID NO:16 (and SEQ ID NO:19). The results of Sections 6 and 7 may thus be considered complementary.

For the monoclonal antibody 1B5, the region SEQ ID NO:17 within SEQ ID NO:1 was identified, and this region (SEQ ID NO:17) was also found within the earlier identified region SEQ ID NO:5. For the monoclonal antibody 7G3, the region SEQ ID NO:18 within SEQ ID NO:1 was identified. This region (SEQ ID NO:18) was also found within the earlier identified region SEQ ID NO:5. This region (SEQ ID NO:18) overlaps with the epitope for the 6F11 antibody (SEQ ID NO:16). For the monoclonal antibody 9B11, the region SEQ ID NO:19 within SEQ ID NO:1 was identified.

8. Evaluation of Antibody Specificity a) Material and Methods

The specificity of the polyclonal antibody (anti-RBM3), and two of the monoclonal antibodies (6F11 and 1B5) were analyzed by Western Blot. Western blot was performed by separation of total protein extracts from selected human cell lines on 17% SDS-PAGE gels under reducing conditions, followed by electro-transfer to PVDF membranes (Bio-Rad Laboratories) according to the manufacturer's recommendations. The membranes were blocked (5% BSA in 1×PBS with 0.1% Tween20) for 1 h at room temperature, incubated with the primary affinity purified antibody (diluted 1:1000 in blocking buffer) and washed in PBST. The secondary HRP-conjugated antibody (sheep anti-mouse immunoglobulin/HRP, GE) was diluted 1:10000 in blocking buffer and chemiluminescence detection was carried out using a Chemidoc™ CCD camera (Bio-Rad Laboratories) and Western Blotting Luminol Reagent (Santa Cruz Biotechnologies, Inc), according to the manufacturer's protocol.

b) Results

The results of the Western blot analysis shows that the antibodies specifically detect a band of approximately 16 kDa in the cell lines. The theoretical molecular weight of RBM3 is 16 kDa (as calculated from the RBM3 amino acid sequence SEQ ID NO:2), corresponding well to the result obtained. Additional bands were observed for anti-RBM3 and 6F11. Overall, the results show that the monoclonal antibodies were more specific than the polyclonal antibody, and that the 1B5 antibody was even more specific than the 6F11 antibody (see FIG. 14).

9. Fractionation of a Polyclonal Anti-RBM3 Antibody a) Materials and Methods

Peptide specific antibodies were obtained by affinity purification of anti-RMB3 against peptides to which the polyclonal anti-RBM3 antibody was shown to bind in Examples, section 6. Among the peptides chosen was peptide 6 (SEQ ID NO:20), and 600 nmol of biotinylated peptide were diluted with HiTrap™ Streptavidin binding buffer to a final volume of 1100 µl and applied to 1 ml HiTrap™ Streptavidin HP columns (GE Healthcare Bio-Sciences AB, Uppsala, Sweden) for binding. After coupling, columns were washed with HiTrap™ Streptavidin binding buffer to remove unbound peptides (and a blank run was performed on all columns prior to sample loading.)

Serum obtained from a New Zeeland white rabbit immunized with the recombinant RBM3 fragment SEQ ID NO: 1 fused to a $His_6$-ABP tag, was purified on a ÄKTAxpress™ (GE Healthcare) liquid chromatography system on eight columns in a serial mode as follows: two 5 ml $His_6$-ABP columns followed by 5 epitope specific peptide columns and at the end a $His_6$-ABP-RBM3 fusion protein column. After sample loading, the columns were washed and eluted in parallel to obtain separate antibody fractions. The eluted antibody fractions were epitope mapped using BioPlex, as described above. To further improve the epitope resolution for the antibody fraction that bound peptide 6, alanine scanning of the peptide was performed using the following method: Twenty biotinylated synthetic peptides of the sequence TQRSRGF-GFITFTNPEHASV (SEQ ID NO: 21), each with a single alanine mutation introduced at every residue (Sigma-Aldrich) were dissolved in DMSO and diluted to 4 µmoles peptide in 100 µL PBS 7.4 supplemented with 1 mg/mL BSA. The peptides were coupled to 20 Bioplex neutravidin coated beads with 20 unique reporter dyes as described above. The antibody fraction binding to peptide 6 was incubated for one hour in PBST with a cocktail of the different beads consisting of around 15,000 beads per ID. The antibodies were subsequently labeled with PE-conjugated secondary reagent (Moss Inc., USA) and analyzed using Bioplex 200 Suspension Array instrumentation with Bio-Plex Manager 5.0 software.

b) Results

When the antibody fraction was epitope mapped, the fractionated antibody bound its expected peptide. The antibody fraction that bound to peptide 6 was confirmed to bind the full-length RBM3 protein (SEQ ID NO:2) by IHC and Western Blot analysis. Preserved antibody binding for the fraction that bound peptide 6 was observed for all amino acid positions except the alanine-substitutions Phe12Ala, Thr13Ala, and Asn14Ala of the epitope. The epitope for the antibody fraction was thus determined to include the sequence FTN (SEQ ID NO:22) within SEQ ID NO:4 (see FIG. 23).

10. Generation of Monoclonal Antibodies II a) Materials and Methods

A synthetic peptide (SEQ ID NO: 23), including peptide 6 (SEQ ID NO: 20) and peptide 7 (SEQ ID NO:24) in Section 6 and having a cystein residue added at its N-terminal to which BSA was coupled according to standard procedure, was used as antigen for production of monoclonal antibodies. The antigen was injected subcutaneously into BALB/c mice (4-6 weeks old, female) at three week intervals. The antigen was mixed with complete Freund's adjuvant for the first injection and incomplete Freund's adjuvant for the following injections. Three days before fusion, the mouse was last challenged with antigen intravenously. Hybridomas were generated by fusion of mouse splenocytes with the Sp2/0 myeloma cell line. By screening several cell lines using ELISA, cells that secreted antibodies specific for the antigen (SEQ ID NO:1) were identified. Cell lines that showed positive results in ELISA, Western blot (WB) and immunohistochemistry (IHC) were selected for subcloning.

In addition, the immunohistochemical staining patterns of the monoclonal antibodies were compared to that of anti-RBM3.

b) Results

Cell-lines were screened by ELISA to identify lines that produce monoclonal antibodies (mAbs) that recognize the antigen (SEQ ID NO:1), but not the fusion tag, BSA. There were 37 cell-lines showing specific binding to the antigen SEQ ID NO:1 in ELISA and these were selected for further testing. For each of the selected 37 clones 150-300 µl supernatant was collected and azide was added. The supernatants were stored at +4° C. Further testing of the cell lines showed that clones denoted 7F5, 10F1, 12A10, 12C9, and 14D9 gave positive results in both Western blot and IHC analysis. These clones were selected for subcloning and expansion.

11. Evaluation of Antibody Specificity II a) Material and Methods

The specificity of the polyclonal antibody (anti-RBM3), obtained as previously described, and the monoclonal antibodies (7F5, 10F1, 12A10, 12C9, and 14D9), obtained as described in Section 10 above, were analyzed by Western Blot. Western blot was performed by separation of total protein extracts from the human cell line RT4 on 4-20% criterion TGX prep well gels under reducing conditions, followed by electro-transfer to PVDF membranes (Millipore) according to the manufacturer's recommendations. The membranes were blocked (5% milk in 1×TBST (0.1% Tween20)) for 1 h at room temperature, incubated with the primary monoclonal antibody (diluted 1:10 in 1% BSA, 1×TBST) and washed in PBST. The secondary HRP-conjugated antibody (polyclonal goat anti-mouse or polyclonal swine anti-rabbit, both Dako) was diluted 1:3000 in blocking buffer and chemiluminescence detection was carried out using a CCD camera (Syngene) and Immobilon Western Chemiluminescent HRP Substrate (Millipore), according to the manufacturer's protocol.

b) Results

The results of the Western blot analysis shows that the antibodies specifically detect a band of approximately 16 kDa in the RT4 cell line. The theoretical molecular weight of RBM3 is 16 kDa (as calculated from the RBM3 amino acid sequence SEQ ID NO:2), corresponding well to the result obtained. Additional bands were observed for anti-RBM3. Overall, the results show that the monoclonal antibodies were more specific than the polyclonal antibody, (see FIG. 22).

12. Epitope Mapping of Monoclonal Antibodies Using Bioplex a) Material and Methods The monoclonal antibodies obtained as described in Section 10, were epitope mapped using Bioplex. Synthetic peptide preparation and bead coupling was performed as described in Section 6. A bead mixture containing all 25 bead IDs was prepared and 10 µl of the monoclonal antibodies, diluted 1:10 in PBS-BN (1% BSA), was mixed with 5 µl of the bead mix and incubated for 60 min at RT. A filter bottomed microtiter plate (Millipore) was utilized for washing and following each incubation all wells were washed with 3×100 µl PBST. 25 µl of PE-conjugated goat anti-mouse IgG (Jackson ImmunoResearch) were added (4 µg/ml) for a final incubation of 60 min at RT.

Measurements were performed using BioPlex 200 Suspension Array instrumentation with Bio-Plex Manager 5.0 software. For each experiment 50 events per bead ID were counted and the median fluorescence intensity (MFI) was used as a measurement of antibody binding to individual bead populations.

b) Results

The specificities of the monoclonal antibodies were tested in an assay using beads coupled with synthetic biotinylated peptides. All monoclonals tested showed strong binding to 2 of the peptides, namely peptide 7 (SEQ ID NO: 24) and 8, SEQ ID NO: 25 (see FIG. 23) corresponding to the consensus sequence SEQ ID NO: 26 within SEQ ID NO:4.

TMA Analysis

13. Colon Carcinoma TMA (Sigmoid Cohort)—1B5 Antibody a) Material and Methods

Archival formalin-fixed paraffin-embedded tissue from 305 patients (148 women and 157 men) surgically treated for sigmoid cancer between 1993 and 2003 was collected from the Department of Pathology, Malmö University Hospital, Sweden. The median age of patients was 74 (39-97) years. 47 tumors were Dukes' stage A, 129 Dukes' stage B, 84 Dukes' stage C and 45 with Dukes' stage D. Information regarding the date of death was obtained from the regional cause-of-death registries for all patients. Ethical permission was obtained from the Local Ethics Committee.

All 305 cases were histopathologically re-evaluated on slides stained with hematoxylin and eosin. TMA:s were then constructed by sampling 2×1.0 mm cores per case from areas representative of sigmoid colon carcinoma.

Automated immunohistochemistry was performed as previously described (Kampf C et al (2004) Clin. Proteomics 1:285-300). In brief, the glass slides were incubated for 45 min in 60° C., de-paraffinized in xylene (2×15 min) and hydrated in graded alcohols. For antigen retrieval, slides were immersed in TRS (Target Retrieval Solution, pH 6.0, Dako, Copenhagen, Denmark) and boiled for 4 min at 125° C. in a Decloaking Chamber® (Biocare Medical). Slides were placed in the Autostainer® (Dako) and endogenous peroxidase was initially blocked with $H_2O_2$ (Dako). The slides were incubated for 30 min at room temperature with the primary RBM3 monoclonal antibody 1B5 obtained as in Examples, Section 3 followed by incubation for 30 min at room temperature with goat anti-mouse peroxidase conjugated Envision®. Between all steps, slides were rinsed in wash buffer (Dako). Finally, diaminobenzidine (Dako) was used as chromogen and Harris hematoxylin (Sigma-Aldrich) was used for counterstaining. The slides were mounted with Pertex® (Histolab).

All samples of immunohistochemically stained tissue were manually evaluated under the microscope and annotated by a certified pathologist. Annotation of each sample was performed using a simplified scheme for classification of IHC outcome. Each tissue sample was examined for representativity and immunoreactivity.

Basic annotation parameters included an evaluation of i) subcellular localization (nuclear and/or cytoplasmic/membranous), ii) staining intensity (SI) and iii) fraction of stained cells (FSC). Staining intensity was subjectively evaluated in accordance to standards used in clinical histo-pathological diagnostics and outcome was classified as: absent=no immunoreactivity, weak—moderate=faint to medium immunoreactivity, or strong=distinct and strong immunoreactivity. Also fraction of stained cells was subjectively evaluated in accordance to standards used in clinical histo-pathological diagnostics and outcome was classified as: <2%, 2-25%, >25-75% or >75% immunoreactive cells of the relevant cell population. The skilled artisan will recognize that this annotation procedure is similar to a calculation of an Allred score, see e.g. Allred et al (1998) Mod Pathol 11(2), 155. Thus, tissue annotation was essentially done as described in Examples, Section 3 above, with the exception that staining intensity and fraction of stained cells were not combined to yield a "staining score".

For statistical analyses, the nuclear fraction (NF), nuclear intensity (NI) level and cytoplasmic intensity (CI) level was evaluated. Based on the survival trends for individual strata, dichotomized variables were constructed for further statistical analyses. For analysis using the 1B5 antibody, a high nuclear fraction was defined either as >25-100% (NF>1) or >75% (NF=3) fraction of cells stained and a low nuclear fraction was defined as ≤25% (NF=0) or 0-75% (NF<3) of fraction of cells stained. Further, a high protein expression level was defined as a strong nuclear intensity (NI>0) and a low protein expression level was defined as an absent—weak or moderate nuclear intensity (NI<2). Also, a high protein expression level was defined either as a strong cytoplasmic intensity (CI=2) and a low protein expression level was defined as an absent—weak or moderate cytoplasmic intensity (CI<2). The above classification of samples was used for overall survival (OS) and disease free survival (DFS) analysis according to the Kaplan-Meier method, and the log-rank test was used to compare survival in different strata. All statistical tests were two-sided, and p-values of <0.05% were considered significant. All calculations were made with the statistical package SPSS 17.0 (SPSS Inc. Illinois, USA).

b) Results

Immunohistochemical analysis of RBM3 expression with the 1B5 antibody could be performed on 245 tumor samples. The remaining cores either did not contain tumor cells or had been lost during histoprocessing. RBM3 expression analysis resulted in a nuclear and cytoplasmic staining in 159 of the analyzed subjects, thus 65% subjects lacked expression (NF<2%).

Figures 15A, 15B:
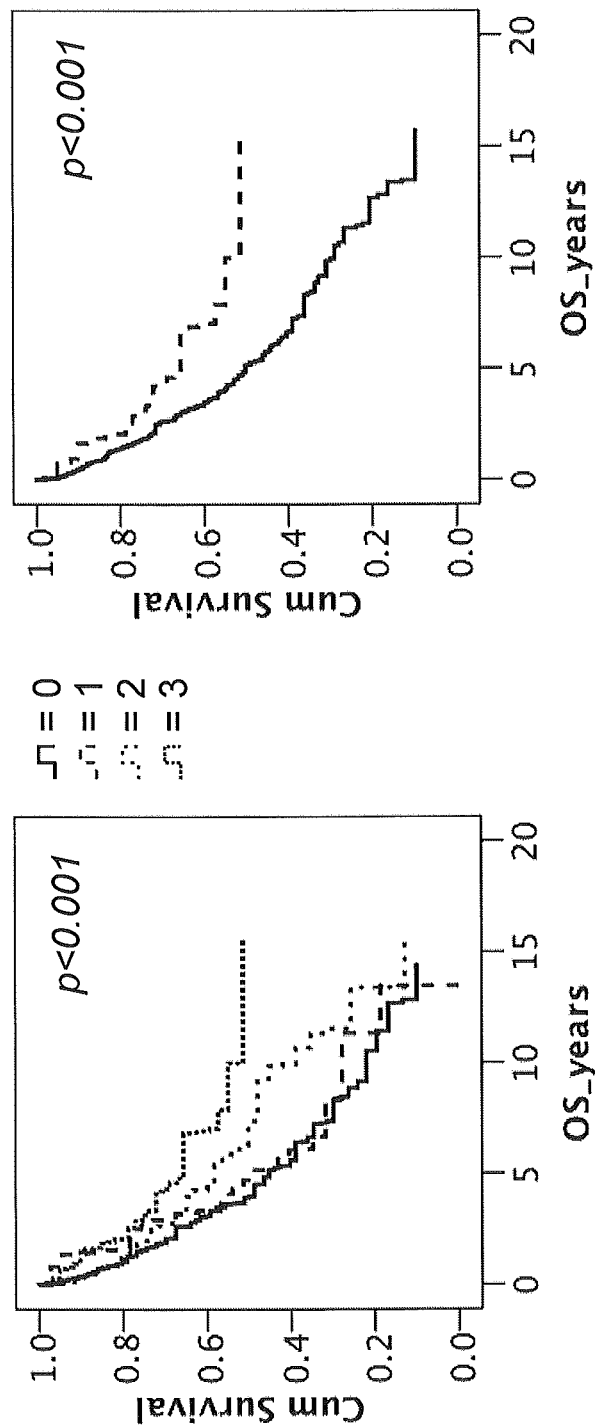
FIGS. 15A-15B show the impact of RBM3 level, using the monoclonal antibody 1B5, on OS if splitting all 245 subjects into groups based on nuclear fraction (NF) staining.
Figure 16A:
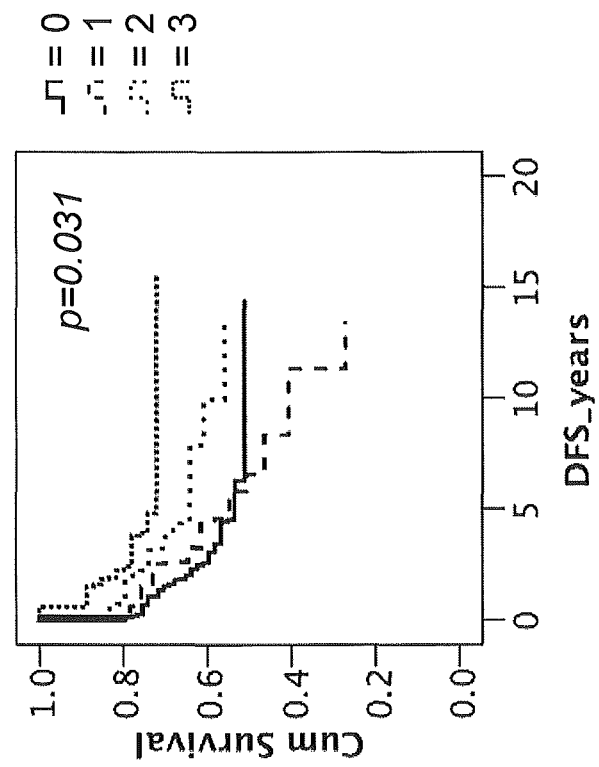
FIGS. 16A-16B show the impact of RBM3 level, using the monoclonal antibody 1B5, on DES if splitting all 245 subjects into groups based on nuclear fraction (NF) staining.
Figure 16B:
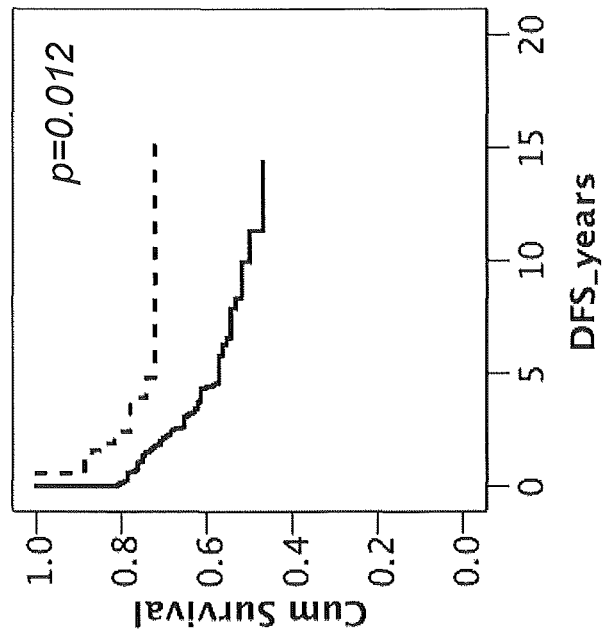
Figure 17B:
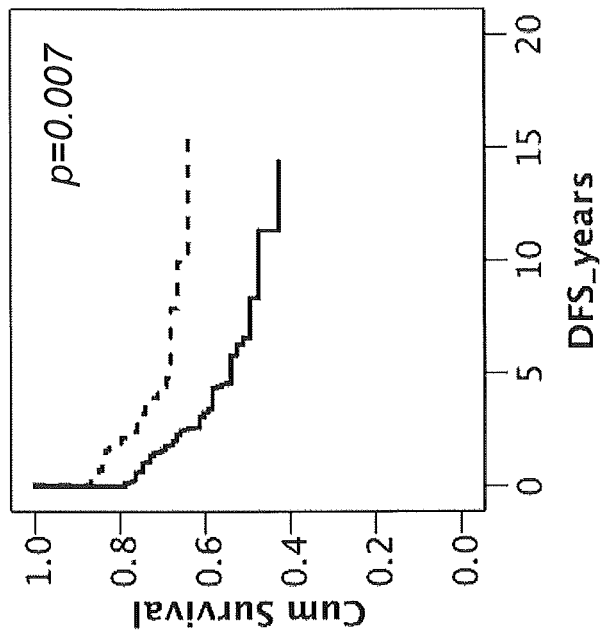
FIGS. 17A-17B show the results of survival analysis for all 245 subjects based on nuclear fraction (NF) levels of RBM3. Tissue cores were dichotomized by high and low RBM3 expression. A solid line represents a low RBM3 level (NF<25%), and a dotted line represents a high RBM3 level (NF≥25%).
Figure 17A:
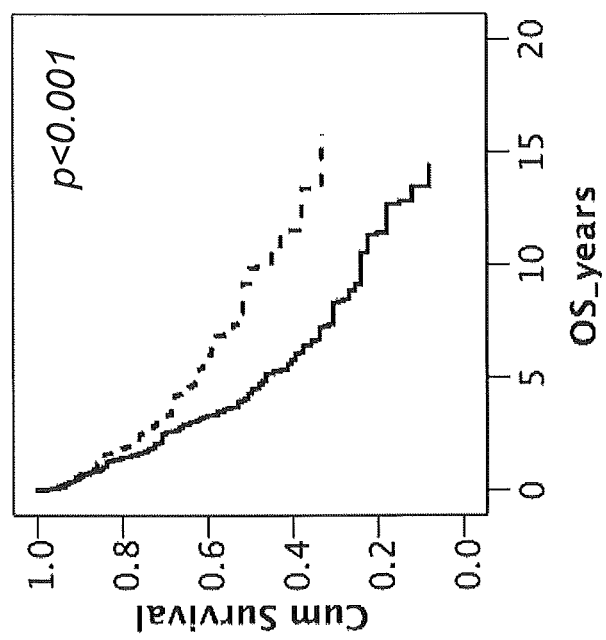
Figure 18B:
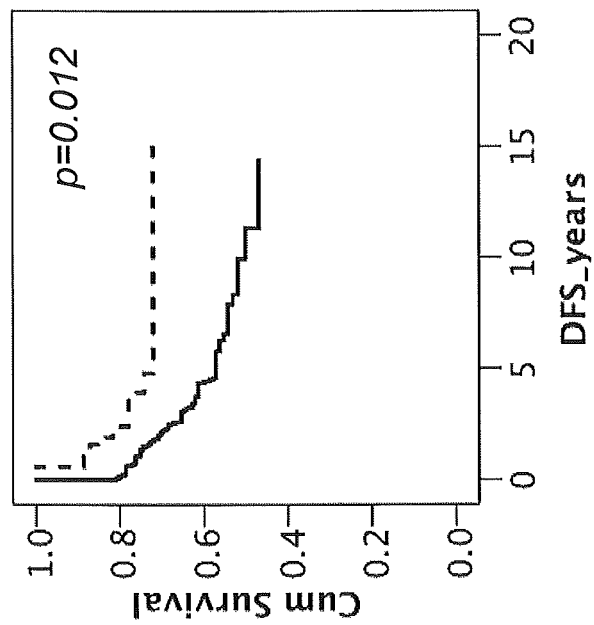
FIGS. 18A-18B show the results of survival analysis for all 245 subjects based on nuclear intensity (NI) levels of RBM3. Tissue cores were dichotomized by high and low RBM3 expression. A solid line represents a low RBM3 level (NI<2), and a dotted line represents a high RBM3 level (NI=2).
Figure 18A:
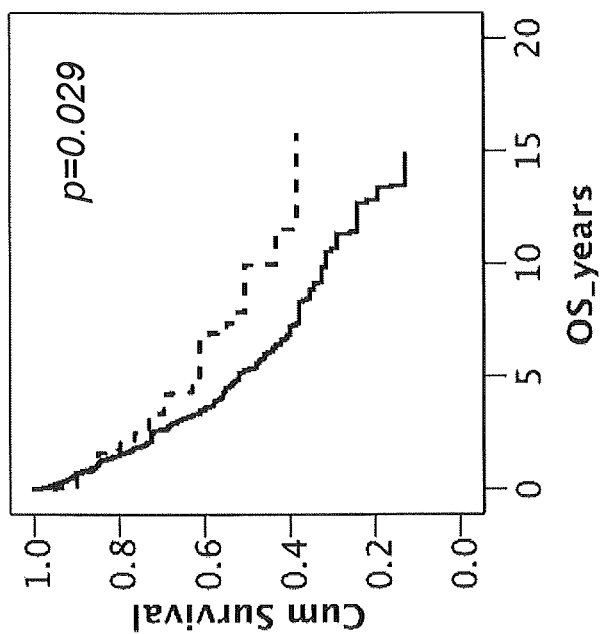
Figure 19B:
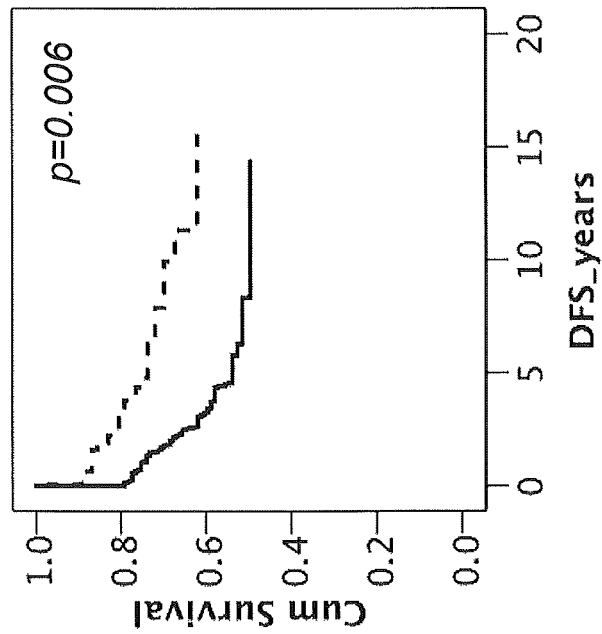
FIGS. 19A-19B show the DFS for all 245 subjects based on cytoplasmic intensity (CI) levels of RBM3. Tissue cores were dichotomized by high and low RBM3 expression.
Figure 19A:
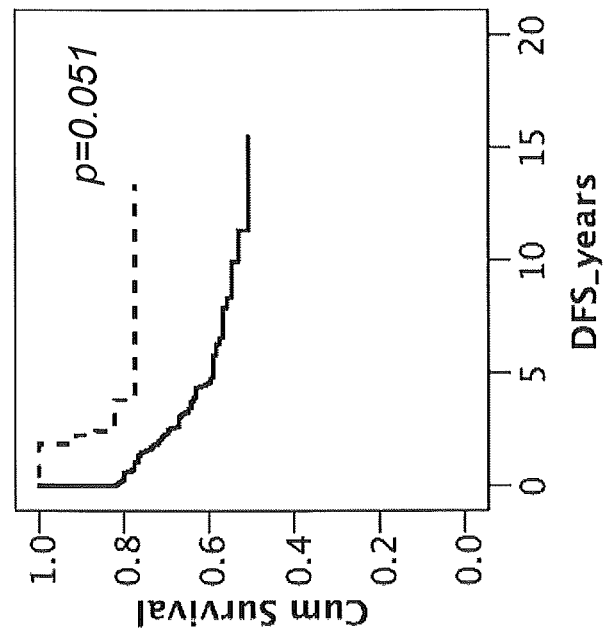

Survival analysis of the entire cohort revealed that NF expression level of RBM3 in tumor tissues was significantly correlated with overall and disease free survival (OS and DFS) (FIGS. 15A-17B). In FIGS. 15A and 16A the subjects were divided into four different categories based on the NF. For patients with a fraction value of NF>75%, five-year OS was approximately 65%, whereas patients lacking RMB3 expression had an OS of about 44% (FIG. 15A-15B). In FIG. 16A-16B, analysis of DFS reveled that patients with a high NF value had a five-year DFS of approximately 73%, whereas patients lacking RMB3 protein expression had a DFS of about 53%. Both FIGS. 15A-15B and 16A-16B clearly shows that the higher the fraction of cells staining positive for RBM3 the longer survival may be expected for the patient. Thus, a high NF indicates a relatively good prognosis whereas a low NF indicates a relatively poor prognosis. Analysis of OS and DFS with dichotomized variables further supports these findings (FIGS. 15B, 16B, 17A and 17B). Further, these figures show that OS and DFS analyses at both a relatively low and a relatively high cut-off yield significant results. Similar results were obtained when analyzing OS and DFS based on nuclear intensity and cytoplasmic intensity (FIGS. 18A-19B). That is, a strong intensity predicts a longer survival.

Figures 20A, 20B, 20C:
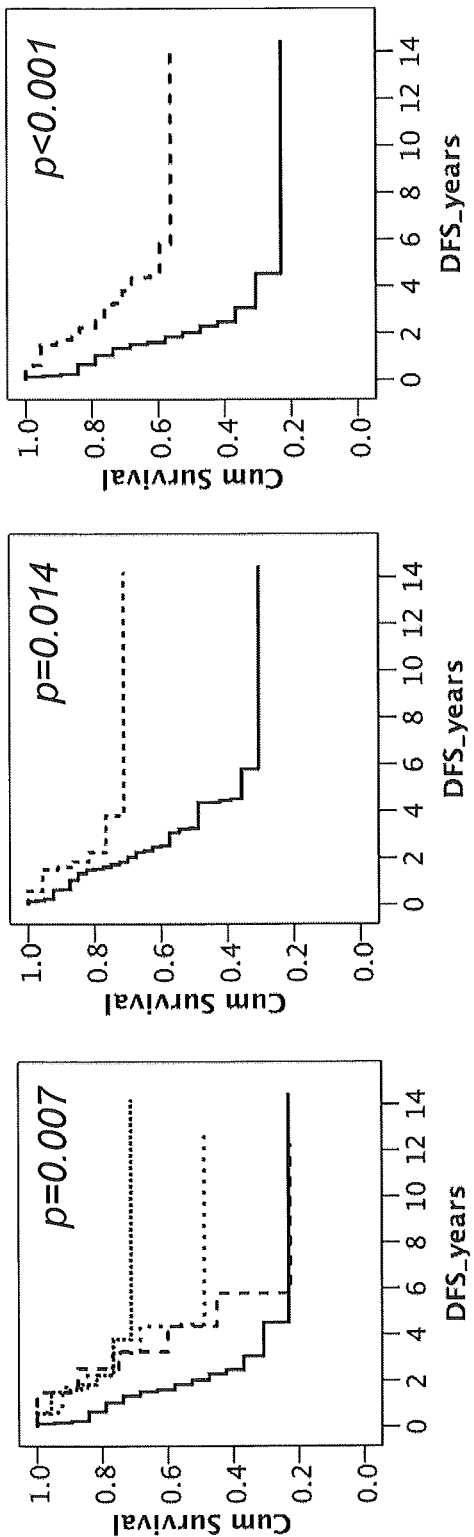
FIGS. 20A-20C show the results of DFS analysis for the 66 subjects diagnosed with Dukes stage C based on nuclear fraction (NF) analysis of RBM3 expression.
Figure 21B:
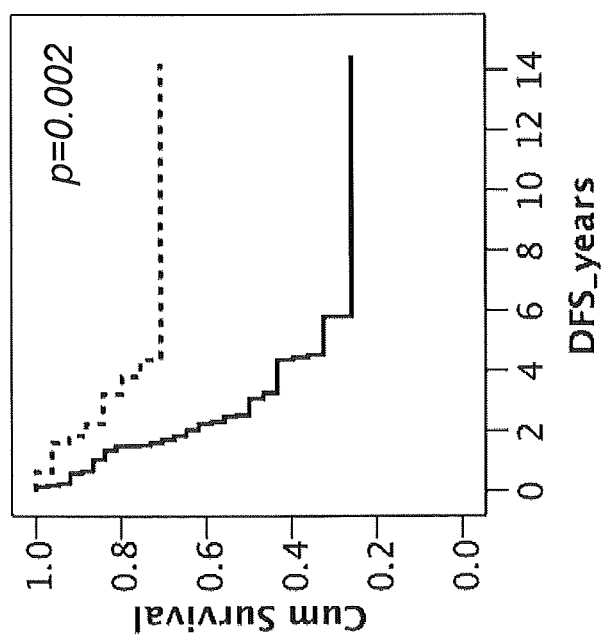
FIGS. 21A-21B show the results of DFS analysis for the 66 subjects diagnosed with Dukes stage C bases on intensity of the RBM3 expression. Tissue cores were dichotomized by high and low RBM3 expression.
Figure 21A:
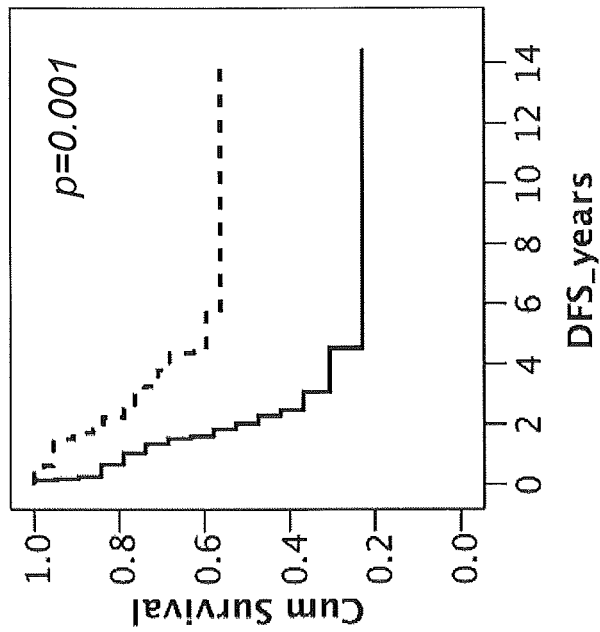

When studying the 66 subjects diagnosed with Dukes' stage C, the difference in survival may be considered even more pronounced. Regarding the patients with a high NF (i.e. >75%), about 71% of the patients were still alive after five years whereas only approximately 22% of the patients with low NF (i.e. NF<2%), were alive after the same time period, see FIG. 20A. Analysis with dichotomized variables further supports these findings (FIGS. 20B-20C). Similar results were obtained when analyzing OS and DFS based on intensity as seen in FIGS. 21A-21B were DFS analysis are shown for cytoplasmic and nuclear intensity, respectively. The stronger the intensity, the longer survival may be expected.

In conclusion, for a patient diagnosed with colorectal cancer, e.g. sigmoid carcinoma, the use of the 1B5 antibody may be of significant value for establishing a prognosis for a patient, e.g. the probability of survival, such as five-year survival, as can be seen from FIGS. 15A to 21B.

Establishment of a Prognosis for a Colon Cancer Patient

14. A Non-Limiting Example

A cancer patient can present with symptoms or signs from tumor growth, focal symptoms including pain and distress from the region where the tumor grows or more general symptoms such as weight loss and fatigue. Signs from growth of a colorectal tumor can also become evident through blood in feces and/or dysfunction, e.g. diarrhea/constipation.

Following the establishment of a colorectal cancer diagnosis in a patient, a tumor tissue sample is obtained. The tumor tissue sample may be obtained from a biopsy performed earlier during the diagnosis of the cancer or from a specimen from an earlier surgical removal of the tumor. Further, for the provision of a "negative reference", a sample is taken from archival material comprising tissue having low, or essentially lacking, RBM3 protein expression. Such archival tissue may for example be colorectal cancer tissue having a pre-established low RBM3 protein expression level or an appropriate tissue having a staining score of 0 in Table 2. Further, for the provision of a "positive reference", a sample is taken from archival material comprising tissue having high RBM3 protein expression, such as colorectal cancer tissue having a pre-established high RBM3 protein expression level.

The sample material is fixated in buffered formalin and histo-processed in order to obtain thin sections (4 µm) of the of the sample material.

Immunohistochemistry is performed as described in Examples, Section 4. One or more sample sections from each sample is/are mounted on glass slides that are incubated for 45 min in 60° C., de-paraffinized (if the sample in question was paraffinized) in xylene (2×15 min) and hydrated in graded alcohols. For antigen retrieval, slides are immersed in TRS (Target Retrieval Solution, pH 6.0, DakoCytomation) and boiled for 4 min at 125° C. in a Decloaking Chamber® (Biocare Medical). Slides are placed in the Autostainer® (DakoCytomation) and endogenous peroxidase is initially blocked with $H_2O_2$ (DakoCytomation). The reason for mounting multiple sample sections is to increase the accuracy of the results.

A primary RBM3 protein specific antibody is added to the slides and incubated for 30 min in room temperature, followed by 30 min of incubation in room temperature with a labeled secondary antibody; e.g. goat-anti-rabbit peroxidase conjugated Envision®. The primary antibody may for example be produced as described in Examples, section 2 or 3 above. To detect the secondary antibody, diaminobenzidine (DakoCytomation) is used as chromogen, contrasted with a Harris hematoxylin (Sigma-Aldrich) counterstaining. Between all steps, slides are rinsed in wash buffer (DakoCytomation). The slides are then mounted with Pertex® (Histolab) mounting media.

As a tool to validate the staining procedure, two control cell-lines may be used; e.g. one slide with cells expressing RBM3 protein (positive cell line) and one slide having cells with indistinct weak or no RBM3 protein expression (negative cell line). The skilled artisan understands how to provide such cell lines, for example guided by the disclosure of Rhodes et al. (2006) The biomedical scientist, p 515-520. The control-line slides may be simultaneously stained in the same procedure as the colorectal cancer slides, i.e. incubated with the same primary and secondary antibodies.

For example, the colorectal cancer tumor slides, the staining reference slides, and optionally, the slides with control cell-lines, may be scanned in a light microscope using a ScanScope T2 automated slide scanning system (Aperio Technologies) at ×20 magnification. However, this scanning step is not necessary, but may make the procedure easier if, for example, the preparation and staining of the slides and the evaluation of the stained slides (see below) are performed at different locations or by different persons.

If control cell-lines are used, these are inspected to validate the staining procedure. If the cell-lines display staining results outside acceptable criteria, e.g. staining artifacts recognized by the skilled artisan, the staining of the biopsy samples is considered invalid and the whole staining procedure is repeated with new slides. If the positive and negative cell-lines display strong staining intensity and indistinct weak or no staining intensity, respectively, the staining is considered as valid.

The stained sample slide(s) from the tumor tissue is/are evaluated manually by visual inspection in accordance to standards used in clinical histo-pathological diagnostics, and the immunoreactivity of the colorectal cancer slide(s) is/are graded as described in Examples, Section 3.

That is, the cytoplasmic intensity (CI), the nuclear intensity (NI) and/or the nuclear fraction (NF) is/are determined.

In the determination of the CI, NI and/or NF, the person performing the evaluation and grading is aided by visual inspection of the stained reference slides, i.e. the "positive reference" and the "negative reference".

The sample value(s), i.e. the CI(s) and/or the CF(s), of the sample slide(s) from the tumor tissue biopsy are then compared to a reference value.

If the sample value(s) or a sample value average is/are equal to or lower than the reference value, a conclusion is drawn that the prognosis is worse than or equal to a reference prognosis being associated with the reference value. In such case, if the reference value is NF<2%, which may be associated with a probability of disease free five-year survival of about 53%, the conclusion may be that the prognosis for the patient is a probability of disease free five-year survival of about 53% (see FIG. 1B).

If the sample value(s) or a sample value average is/are higher than the reference value, a conclusion is drawn that the prognosis is better than a reference prognosis being associated with the reference value. In such case, if the reference value is NF<2%, the conclusion may be that the prognosis for the patient is a probability of disease free five-year survival of higher than about 53% (see FIG. 1B).

The invention claimed is:

1. An affinity ligand that selectively binds an RBM3 protein fragment which
consists of an amino acid sequence selected from SEQ ID NO:4 and 5 or
consists of 20 amino acids or less and comprises an amino acid sequence selected from SEQ ID NO:8, 16 and 17.

2. The affinity ligand according to claim 1, that selectively binds an RBM3 protein fragment which consists of 15 amino acids or less and comprises an amino acid sequence selected from SEQ ID NO:6, 8, 16 and 17.

3. The affinity ligand according to claim 1, which is an antibody, a Fab fragment, a Fv fragment or a single chain Fv (scFv) fragment.

4. The affinity ligand according to claim 3, which is a monoclonal antibody.

5. A kit comprising:
a) an affinity ligand according to claim 1; and
b) a secondary affinity ligand that recognizes the affinity ligand of a).

6. An affinity ligand, which is obtainable by a process comprising a step of immunizing an animal with
a peptide whose amino acid sequence consists of sequence SEQ ID NO:4 or 5 or
an RBM3 protein fragment which consists of 20 amino acids or less and comprises an amino acid selected from the group consisting of SEQ ID NO:6, 8, 16 and 17.

7. The affinity ligand according to claim 6, which is obtainable by a process comprising a step of immunizing an animal with an RBM3 protein fragment which consists of 15 amino acids or less and comprises an amino acid selected from the group consisting of SEQ ID NO:6, 8, 16 and 17.

8. The affinity ligand according to claim 6, which is an antibody, a Fab fragment, a Fv fragment or a single chain Fv (scFv) fragment.

9. The affinity ligand according to claim 8, which is a monoclonal antibody.

10. A kit comprising:
a) an affinity ligand according to claim 6; and
b) a secondary affinity ligand that recognizes the affinity ligand of a).

* * * * *

SEQUENCE LISTING

```
<160> NUMBER OF SEQ ID NOS: 28

<210> SEQ ID NO 1
<211> LENGTH: 134
<212> TYPE: PRT
<213> ORGANISM: Homo sapiens

<400> SEQUENCE: 1

Asp Glu Gln Ala Leu Glu Asp His Phe Ser Ser Phe Gly Pro Ile Ser
1               5                   10                  15

Glu Val Val Val Lys Asp Arg Glu Thr Gln Arg Ser Arg Gly Phe
            20                  25                  30

Gly Phe Ile Thr Phe Thr Asn Pro Glu His Ala Ser Val Ala Met Arg
        35                  40                  45

Ala Met Asn Gly Glu Ser Leu Asp Gly Arg Gln Ile Arg Val Asp His
    50                  55                  60

Ala Gly Lys Ser Ala Arg Gly Thr Arg Gly Gly Phe Gly Ala His
65                  70                  75                  80

Gly Arg Gly Arg Ser Tyr Ser Arg Gly Gly Gly Asp Gln Gly Tyr Gly
                85                  90                  95

Ser Gly Arg Tyr Tyr Asp Ser Arg Pro Gly Gly Tyr Gly Tyr Gly Tyr
            100                 105                 110

Gly Arg Ser Arg Asp Tyr Asn Gly Arg Asn Gln Gly Gly Tyr Asp Arg
        115                 120                 125

Tyr Ser Gly Gly Asn Tyr
    130
```

<210> SEQ ID NO 2
<211> LENGTH: 157
<212> TYPE: PRT
<213> ORGANISM: Homo sapiens

<400> SEQUENCE: 2

Met Ser Ser Glu Glu Gly Lys Leu Phe Val Gly Gly Leu Asn Phe Asn
1               5                   10                  15

Thr Asp Glu Gln Ala Leu Glu Asp His Phe Ser Ser Phe Gly Pro Ile
            20                  25                  30

Ser Glu Val Val Val Lys Asp Arg Glu Thr Gln Arg Ser Arg Gly
        35                  40                  45

Phe Gly Phe Ile Thr Phe Thr Asn Pro Glu His Ala Ser Val Ala Met
    50                  55                  60

Arg Ala Met Asn Gly Glu Ser Leu Asp Gly Arg Gln Ile Arg Val Asp
65                  70                  75                  80

His Ala Gly Lys Ser Ala Arg Gly Thr Arg Gly Gly Phe Gly Ala
                85                  90                  95

His Gly Arg Gly Arg Ser Tyr Ser Arg Gly Gly Gly Asp Gln Gly Tyr
            100                 105                 110

Gly Ser Gly Arg Tyr Tyr Asp Ser Arg Pro Gly Gly Tyr Gly Tyr Gly
            115                 120                 125

Tyr Gly Arg Ser Arg Asp Tyr Asn Gly Arg Asn Gln Gly Gly Tyr Asp
        130                 135                 140

Arg Tyr Ser Gly Gly Asn Tyr Arg Asp Asn Tyr Asp Asn
145                 150                 155

<210> SEQ ID NO 3
<211> LENGTH: 1130
<212> TYPE: DNA
<213> ORGANISM: Homo sapiens

<400> SEQUENCE: 3

```
atgcgcaatg tggccccta  atggtggctg cgctgagcca gctcctcaga ttaccacctt      60
attggccgcc tttctcagct tttctgtagt tacccatatt ttgttcctct ttcttgtcta     120
ttttctgtgc tttttctctg ctttccgtct cgctattttc tcacatctcc attttctttc     180
tccttcctgc caccattctt catgttcttc ccacaggact tgaactgcca tgtcctctga     240
agaaggaaag ctcttcgtgg agggctcaa  ctttaacacc gacagcagg  cactggaaga     300
ccacttcagc agtttcggac ctatctctga ggtggtcgtt gtcaaggacc gggagactca     360
gcggtccagg ggttttggtt tcatcacctt caccaaccca gagcatgctt cagttgccat     420
gagagccatg aacggagagt ctctggatgg tcgtcagatc cgtgtggatc atgcaggcaa     480
gtctgctcgg ggaaccagag gaggtggctt tggggcccat gggcgtggtc gcagctactc     540
tagaggtggt ggggaccagg gctatgggag tggcaggtat tatgacagtc gacctggagg     600
gtatggatat ggatatggac gttccagaga ctataatggc agaaaccagg gtggttatga     660
ccgctactca ggaggaaatt acagagacaa ttatgacaac tgaaatgaga catgcacata     720
atatagatac acaaggaata atttctgatc caggatcgtc cttccaaatg gctgtattta     780
taaaggtttt tggagctgca ccgaagcatc ttatttata  gtatatcaac cttttgtttt     840
taaattgacc tgccaaggta gctgaagacc tttagacag  ttccatcttt ttttttaaat     900
tttttctgcc tatttaaaga caaattatgg gacgtttgta gaacctgagt attttctttt     960
ttaccagttt tttagtttga gctcttaggt ttattggagc tagcaataat tggttctggc    1020
```

```
aagtttggcc agactgactt caaaaaatta atgtgtatcc agggacattt taaaaacctg    1080
tacacagtgt ttattgtggt taggaagcaa tttcccaatg tacctataag              1130
```

<210> SEQ ID NO 4
<211> LENGTH: 29
<212> TYPE: PRT
<213> ORGANISM: Homo sapiens

<400> SEQUENCE: 4

```
Arg Gly Phe Gly Phe Ile Thr Phe Thr Asn Pro Glu His Ala Ser Val
1               5                   10                  15

Ala Met Arg Ala Met Asn Gly Glu Ser Leu Asp Gly Arg
            20                  25
```

<210> SEQ ID NO 5
<211> LENGTH: 24
<212> TYPE: PRT
<213> ORGANISM: Homo sapiens

<400> SEQUENCE: 5

```
Arg Ser Tyr Ser Arg Gly Gly Gly Asp Gln Gly Tyr Gly Ser Gly Arg
1               5                   10                  15

Tyr Tyr Asp Ser Arg Pro Gly Gly
            20
```

<210> SEQ ID NO 6
<211> LENGTH: 5
<212> TYPE: PRT
<213> ORGANISM: Homo sapiens

<400> SEQUENCE: 6

```
Thr Phe Thr Asn Pro
1               5
```

<210> SEQ ID NO 7
<211> LENGTH: 10
<212> TYPE: PRT
<213> ORGANISM: Homo sapiens

<400> SEQUENCE: 7

```
Gly Thr Arg Gly Gly Gly Phe Gly Ala His
1               5                   10
```

<210> SEQ ID NO 8
<211> LENGTH: 10
<212> TYPE: PRT
<213> ORGANISM: Homo sapiens

<400> SEQUENCE: 8

```
Gly Phe Gly Ala His Gly Arg Gly Arg Ser
1               5                   10
```

<210> SEQ ID NO 9
<211> LENGTH: 5
<212> TYPE: PRT
<213> ORGANISM: Homo sapiens

<400> SEQUENCE: 9

```
Tyr Asp Arg Tyr Ser
1               5
```

<210> SEQ ID NO 10
<211> LENGTH: 9

```
<212> TYPE: PRT
<213> ORGANISM: Homo sapiens

<400> SEQUENCE: 10

Asp Glu Gln Ala Leu Glu Asp His Phe
1               5

<210> SEQ ID NO 11
<211> LENGTH: 7
<212> TYPE: PRT
<213> ORGANISM: Homo sapiens

<400> SEQUENCE: 11

Thr Asn Pro Glu His Ala Ser
1               5

<210> SEQ ID NO 12
<211> LENGTH: 10
<212> TYPE: PRT
<213> ORGANISM: Homo sapiens

<400> SEQUENCE: 12

Glu His Ala Ser Val Ala Met Arg Ala Met
1               5                   10

<210> SEQ ID NO 13
<211> LENGTH: 10
<212> TYPE: PRT
<213> ORGANISM: Homo sapiens

<400> SEQUENCE: 13

Arg Gly Gly Gly Phe Gly Ala His Gly Arg
1               5                   10

<210> SEQ ID NO 14
<211> LENGTH: 8
<212> TYPE: PRT
<213> ORGANISM: Homo sapiens

<400> SEQUENCE: 14

Gly Phe Gly Ala His Gly Arg Gly
1               5

<210> SEQ ID NO 15
<211> LENGTH: 9
<212> TYPE: PRT
<213> ORGANISM: Homo sapiens

<400> SEQUENCE: 15

Asp Tyr Asn Gly Arg Asn Gln Gly Gly
1               5

<210> SEQ ID NO 16
<211> LENGTH: 10
<212> TYPE: PRT
<213> ORGANISM: Homo sapiens

<400> SEQUENCE: 16

His Gly Arg Gly Arg Ser Tyr Ser Arg Gly
1               5                   10

<210> SEQ ID NO 17
<211> LENGTH: 7
<212> TYPE: PRT
<213> ORGANISM: Homo sapiens
```

<400> SEQUENCE: 17

Gly Ser Gly Arg Tyr Tyr Asp
1               5

<210> SEQ ID NO 18
<211> LENGTH: 6
<212> TYPE: PRT
<213> ORGANISM: Homo sapiens

<400> SEQUENCE: 18

Ser Gly Arg Tyr Tyr Asp
1               5

<210> SEQ ID NO 19
<211> LENGTH: 3
<212> TYPE: PRT
<213> ORGANISM: Homo sapiens

<400> SEQUENCE: 19

Asp Glu Gln
1

<210> SEQ ID NO 20
<211> LENGTH: 15
<212> TYPE: PRT
<213> ORGANISM: Homo sapiens

<400> SEQUENCE: 20

Thr Gln Arg Ser Arg Gly Phe Gly Phe Ile Thr Phe Thr Asn Pro
1               5                   10                  15

<210> SEQ ID NO 21
<211> LENGTH: 20
<212> TYPE: PRT
<213> ORGANISM: Homo sapiens

<400> SEQUENCE: 21

Thr Gln Arg Ser Arg Gly Phe Gly Phe Ile Thr Phe Thr Asn Pro Glu
1               5                   10                  15

His Ala Ser Val
            20

<210> SEQ ID NO 22
<211> LENGTH: 3
<212> TYPE: PRT
<213> ORGANISM: Homo sapiens

<400> SEQUENCE: 22

Phe Thr Asn
1

<210> SEQ ID NO 23
<211> LENGTH: 21
<212> TYPE: PRT
<213> ORGANISM: Homo sapiens

<400> SEQUENCE: 23

Cys Thr Gln Arg Ser Arg Gly Phe Gly Phe Ile Thr Phe Thr Asn Pro
1               5                   10                  15

Glu His Ala Ser Val
            20

```
<210> SEQ ID NO 24
<211> LENGTH: 15
<212> TYPE: PRT
<213> ORGANISM: Homo sapiens

<400> SEQUENCE: 24

Gly Phe Gly Phe Ile Thr Phe Thr Asn Pro Glu His Ala Ser Val
1               5                   10                  15

<210> SEQ ID NO 25
<211> LENGTH: 15
<212> TYPE: PRT
<213> ORGANISM: Homo sapiens

<400> SEQUENCE: 25

Thr Phe Thr Asn Pro Glu His Ala Ser Val Ala Met Arg Ala Met
1               5                   10                  15

<210> SEQ ID NO 26
<211> LENGTH: 10
<212> TYPE: PRT
<213> ORGANISM: Homo sapiens

<400> SEQUENCE: 26

Thr Phe Thr Asn Pro Glu His Ala Ser Val
1               5                   10

<210> SEQ ID NO 27
<211> LENGTH: 19
<212> TYPE: DNA
<213> ORGANISM: Homo sapiens

<400> SEQUENCE: 27
gacgagcagg cactggaag                                            19

<210> SEQ ID NO 28
<211> LENGTH: 20
<212> TYPE: DNA
<213> ORGANISM: Homo sapiens

<400> SEQUENCE: 28
gtaatttcct cctgagtagc                                           20
```